US012708887B2

(12) United States Patent
Ghonge et al.

(10) Patent No.: US 12,708,887 B2
(45) Date of Patent: Aug. 18, 2026

(54) FLOW CELL SURFACE PATTERNING

(71) Applicant: ILLUMINA, INC., San Diego, CA (US)

(72) Inventors: Tanmay Ghonge, San Diego, CA (US); Brian D. Mather, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 824 days.

(21) Appl. No.: 18/145,843

(22) Filed: Dec. 22, 2022

(65) Prior Publication Data

US 2023/0330617 A1 Oct. 19, 2023

Related U.S. Application Data

(60) Provisional application No. 63/293,959, filed on Dec. 27, 2021.

(51) Int. Cl.
*B01J 19/00* (2006.01)
*C12Q 1/6806* (2018.01)

(52) U.S. Cl.
CPC ........ *B01J 19/0046* (2013.01); *C12Q 1/6806* (2013.01); *B01J 2219/00722* (2013.01)

(58) Field of Classification Search
CPC ........ B01J 19/0046; B01J 2219/00722; C12Q 1/6806; C12Q 1/6869; C12Q 2521/301; C12Q 2523/319; C12Q 2525/117; C12Q 2525/137; C12Q 2527/156; C12Q 2521/319
See application file for complete search history.

(56) References Cited

U.S. PATENT DOCUMENTS

2012/0316086 A1* 12/2012 Lin ...................... C12Q 1/6837 506/26
2022/0379305 A1* 12/2022 Kodira Cariappa ........................ B01J 19/0046

FOREIGN PATENT DOCUMENTS

WO WO-2020005503 A1 * 1/2020 ........... G03F 7/0002
WO 2020167447 A1 8/2020
WO 2021194640 A1 9/2021
WO 2021214037 A1 10/2021

* cited by examiner

*Primary Examiner* — Robert T. Crow
*Assistant Examiner* — Allison E Schloop
(74) *Attorney, Agent, or Firm* — Dierker & Kavanaugh, P.C.

(57) ABSTRACT

A polymeric hydrogel is applied to a surface of a substrate including depressions separated by interstitial regions. Each depression includes a UV blocking layer positioned at a first region, and a second region that is transparent to UV and adjacent to the first region. Before or after the hydrogel is applied, a primer set is grafted to the hydrogel. The primer set includes 3' blocked uncleavable first and second pre-primers. The hydrogel or grafted layer is removed from the interstitial regions. At a first predetermined region of the grafted layer within the second region: the first pre-primers are altered to introduce cleavable first primers; and the second pre-primers are altered to introduce uncleavable second primers. At a second predetermined region of the grafted layer within the first region: the first pre-primers are altered to introduce uncleavable first primers; and the second pre-primers are blocked to introduce cleavable second primers.

10 Claims, 12 Drawing Sheets

Specification includes a Sequence Listing.

14
12
60
58
16
10A
18A
20

10B
18B

60"
58"
16'
10C
18C
22

58'
60'
12'
24
26
10D
18D
$t_1$
$t_2$
$t_3$ 10B
18B
28
30
32
34
36
38
40
42
50A
52A
58
60
62, 62'
62, 62"
62'
28, 64
12
14
16

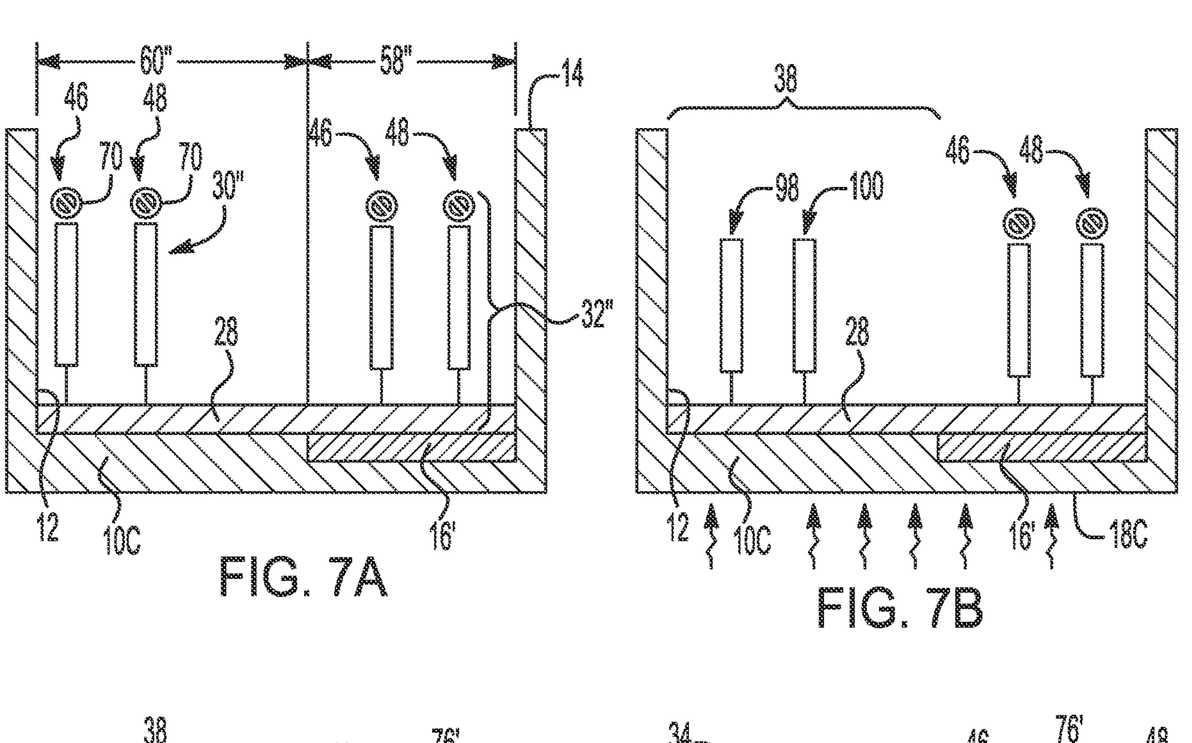
FIG. 7A
FIG. 7B
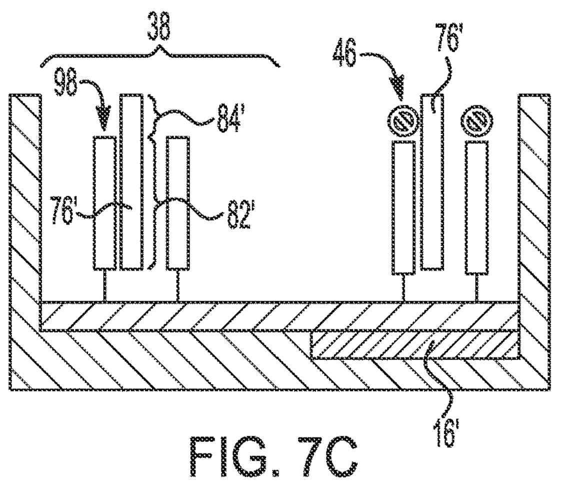
FIG. 7C
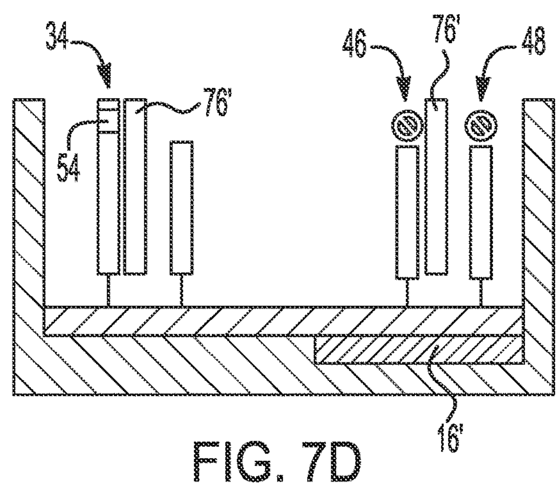
FIG. 7D
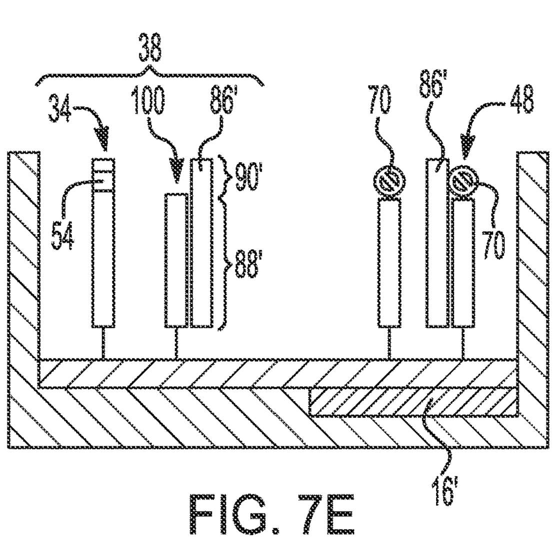
FIG. 7E
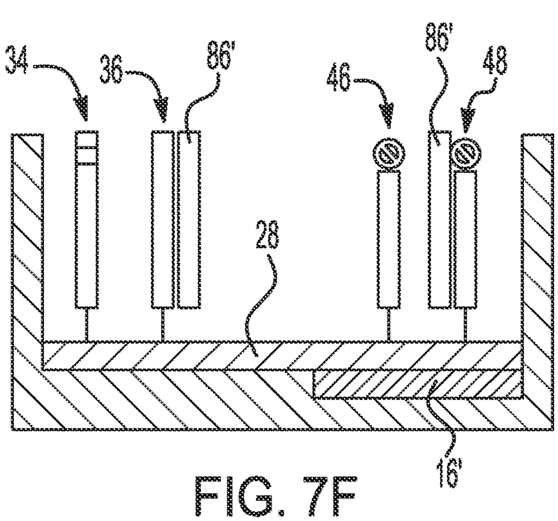
FIG. 7F

FLOW CELL SURFACE PATTERNING

CROSS REFERENCE TO RELATED APPLICATION

This application claims the benefit of U.S. Provisional Application Ser. No. 63/293,959, filed Dec. 27, 2021, the contents of which is incorporated by reference herein in its entirety.

REFERENCE TO SEQUENCE LISTING

The Replacement Sequence Listing submitted May 30, 2023 is hereby incorporated by reference in its entirety. The name of the file is ILI236B_IP-2237-US2_Sequence_Listing_2.xml, the size of the file is 20,069 bytes, and the date of creation of the file is May 8, 2023.

BACKGROUND

Some available platforms for sequencing nucleic acids utilize a sequencing-by-synthesis approach. With this approach, a nascent strand is synthesized, and the addition of each monomer (e.g., nucleotide) to the growing strand is detected optically and/or electronically. Because a template strand directs synthesis of the nascent strand, one can infer the sequence of the template DNA from the series of nucleotide monomers that were added to the growing strand during the synthesis. In some examples, sequential paired-end sequencing may be used, where forward strands are sequenced and removed, and then reverse strands are constructed and sequenced. In other examples, simultaneous paired-end sequencing may be used, where forward strands and reverse strands are sequenced at the same time.

SUMMARY

For some examples of simultaneous paired-end sequencing, different primer sets are attached to different regions within each depression of a flow cell surface. The methods described herein begin with a single primer set (also referred to herein as the initial primer set) attached to a polymeric hydrogel in each of the depressions, and then the primer set is altered at one or more regions to generate the different primer sets within the depressions. In these examples, the alteration of the single primer set takes place after the polymeric hydrogel and the single primer set are introduced into the depressions. As such, the same polymeric hydrogel is applied in each of the depressions. Thus, the polymeric hydrogel is not exposed to physical patterning, which can be challenging, sometimes irreproducible, and result in imbalanced cluster intensities from the different primer sets.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 3A depicts an ultraviolet (UV) light blocking layer applied to a first region of a depression defined in a substrate, and a grafted layer (including the single primer set) applied over the UV light blocking layer and over exposed regions of the substrate, FIG. 3B depicts a negative photoresist applied over the grafted layer of FIG. 3A, FIG. 3C depicts an insoluble negative photoresist formed from the negative photoresist of FIG. 3B so that a portion of the grafted layer is exposed, FIG. 3D depicts a primer depleted portion of a polymeric hydrogel after the grafted layer is exposed to a nuclease to remove some of the primers of the single primer set, FIG. 3E depicts different primers (than those in the single primer set) grafted to the primer depleted portion of FIG. 3D, FIG. 3F depicts the insoluble negative photoresist removed, and FIG. 3G depicts the depression with different primers in different regions, and interstitial regions that are free of the polymeric hydrogel and of the different primers;

FIG. 4A depicts a substrate with a multi-depth depression, FIG. 4B depicts a grafted primer layer (including the single primer set) on the substrate of FIG. 4A, FIG. 4C depicts a negative photoresist applied over the grafted layer of FIG. 4B, FIG. 4D depicts an insoluble negative photoresist formed from the negative photoresist of FIG. 4C so that a portion of the grafted layer is exposed, FIG. 4E depicts a primer depleted portion of a polymeric hydrogel after the grafted layer is exposed to a nuclease to remove some of the primers of the single primer set, FIG. 4F depicts different primers (than those in the single primer set) grafted to the primer depleted portion of FIG. 4E, FIG. 4G depicts the insoluble negative photoresist removed, and FIG. 4H depicts the multi-depth depression with different primers in different regions, and interstitial regions that are free of the polymeric hydrogel and of the different primers;

FIG. 5A depicts a substrate with a multi-depth depression, FIG. 5B depicts a grafted primer layer (including the single primer set) on the substrate of FIG. 5A, FIG. 5C depicts a positive photoresist applied over the grafted layer of FIG. 5B, FIG. 5D depicts an insoluble positive photoresist formed from the positive photoresist of FIG. 5C so that a portion of the grafted layer is exposed, FIG. 5E depicts a primer depleted portion of a polymeric hydrogel after the grafted layer is exposed to a nuclease to remove some of the primers of the single primer set, FIG. 5F depicts different primers (than those in the single primer set) grafted to the primer depleted portion of FIG. 5E, FIG. 5G depicts the insoluble positive photoresist removed, and FIG. 5H depicts the multi-depth depression with different primers in different regions, and interstitial regions that are free of the polymeric hydrogel and of the different primers;

FIG. 6A depicts an ultraviolet (UV) light blocking layer embedded in a portion of a depression defined in a substrate, and a grafted layer (including the single primer set, where each primer includes a nuclease resistant modification and a photocleavable blocking group) applied over the UV light blocking layer and over exposed regions of the depression, FIG. 6B depicts the removal of the photocleavable blocking groups from primers that do not overlie the UV light blocking layer, FIG. 6C depicts the digestion of portions of the primers that do not overlie the UV light blocking layer, FIG. 6D depicts first primer regeneration templates hybridized to some of the remaining portions of the primers and some of the primers overlying the UV light blocking layer, FIG. 6E depicts polymerase extension along the first primer regeneration templates, FIG. 6F depicts second primer regeneration templates hybridized to some other of the remaining portions of the primers and some other of the primers overlying the UV light blocking layer, FIG. 6G depicts polymerase extension along the second primer regeneration templates, FIG. 6H depicts the depression of FIG. 6G after the second primer regeneration templates are dehybridized, and FIG. 6I depicts the removal of photocleavable blocking groups from the primers that overlie the UV light blocking layer;

FIG. 7A through FIG. 7M are schematic views that together illustrate a further example of a method to alter at least some of the primers in a single primer set, where FIG. 7A depicts an ultraviolet (UV) light blocking layer embedded in a portion of a depression defined in a substrate, and a grafted layer (including the single primer set, where each primer includes a photocleavable blocking group) applied over the UV light blocking layer and over exposed regions of the depression, FIG. 7B depicts the removal of the photocleavable blocking groups from primers that do not overlie the UV light blocking layer, FIG. 7C depicts first primer regeneration templates hybridized to some of the unblocked primers and some of the blocked primers, FIG. 7D depicts polymerase extension along the first primer regeneration templates hybridized to the unblocked primers, FIG. 7E depicts second primer regeneration templates hybridized to some other of the unblocked primers and some other of the blocked primers, FIG. 7F depicts polymerase extension along the second primer regeneration templates, FIG. 7G depicts the primers after the second primer regeneration templates are dehybridized, FIG. 7H depicts UV light exposure to remove the photocleavable blocking group from the primers that overlie the UV light blocking layer, FIG. 7I depicts first primer regeneration templates hybridized to some of the unblocked primers, FIG. 7J depicts polymerase extension along the first primer regeneration templates hybridized to the unblocked primers that overlie the UV light blocking layer, FIG. 7K depicts second primer regeneration templates hybridized to some of the unblocked primers, FIG. 7L depicts polymerase extension along the second primer regeneration templates hybridized to the unblocked primers that overlie the UV light blocking layer, and FIG. 7M depicts two different primers sets in the depression;

DETAILED DESCRIPTION

Figures 1A, 1B, 1C, 1D:
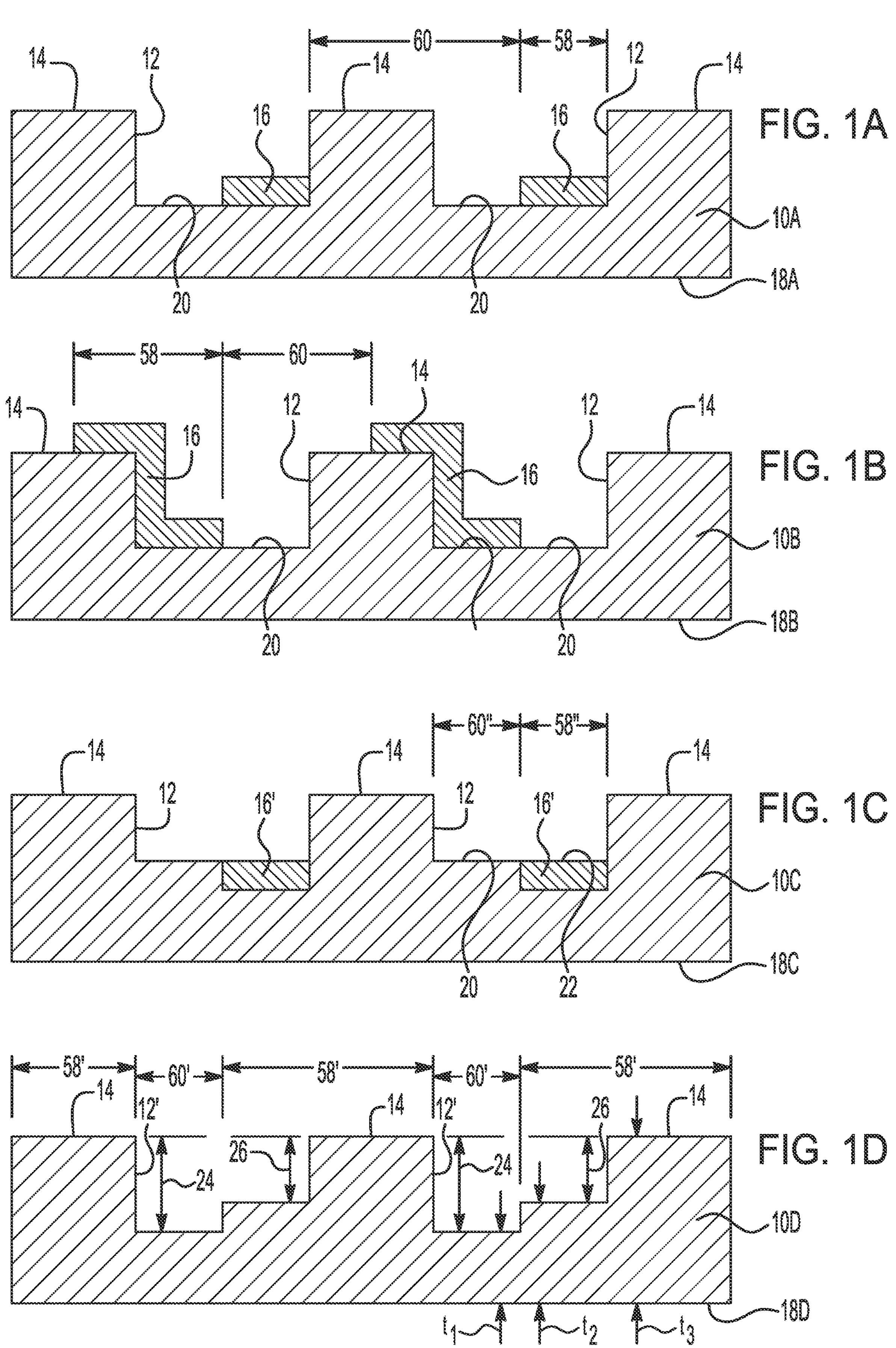
FIG. 1A is a cross-sectional view of one example substrate configuration that may be used in example(s) of the method disclosed herein.
FIG. 1B is a cross-sectional view of another example substrate configuration that may be used in example(s) of the method disclosed herein.
FIG. 1C is a cross-sectional view of still another example substrate configuration that may be used in example(s) of the method disclosed herein.
FIG. 1D is a cross-sectional view of yet another example substrate configuration that may be used in example(s) of the method disclosed herein.

The methods disclosed herein generate flow cells that are suitable for use in simultaneous paired-end sequencing. Each method utilizes a polymeric hydrogel having a single (initial) primer set attached thereto, and involves the alteration of at least some of the primers in the single primer set. The alteration of at least some of the primers results in different primer sets being located at different regions of the polymeric hydrogel. The primer sets at the different regions have orthogonal cleaving (linearization) chemistry. The orthogonal cleaving chemistry may be realized through identical or different cleavage sites that are attached to different primers in the different sets. The orthogonal cleaving chemistry enables a cluster of forward amplicon strands to be generated in one region and a cluster of reverse amplicon strands to be generated in another region. The forward and reverse strands are spatially separate, which separates the fluorescence signals from both reads while allowing for simultaneous base calling of each read.

Definitions

It is to be understood that terms used herein will take on their ordinary meaning in the relevant art unless specified otherwise. Several terms used herein and their meanings are set forth below.

The singular forms “a”, “an”, and “the” include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

It is to be understood that the ranges provided herein include the stated range and any value or sub-range within the stated range, as if such values or sub-ranges were explicitly recited. For example, a range of about 400 nm to about 1 μm (1000 nm), should be interpreted to include not only the explicitly recited limits of about 400 nm to about 1 μm, but also to include individual values, such as about 708 nm, about 945.5 nm, etc., and sub-ranges, such as from about 425 nm to about 825 nm, from about 550 nm to about 940 nm, etc.

Furthermore, when “about” and/or “substantially” are/is utilized to describe a value, they are meant to encompass minor variations (up to +/−10%) from the stated value.

An “acrylamide monomer” is a monomer with the structure

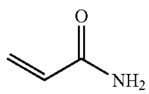

or a monomer including an acrylamide group. Examples of the monomer including an acrylamide group include azido acetamido pentyl acrylamide:

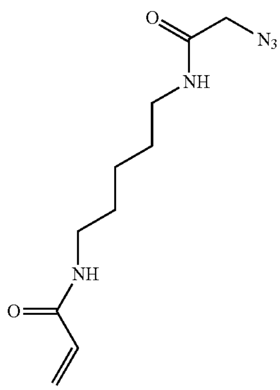 [SMILES: C=CC(=O)NCCCCCNC(=O)CN=[N+]=[N-]]

and N-isopropylacrylamide:

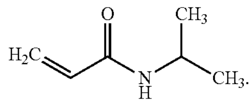

Other acrylamide monomers may be used.

The term "activation," as used herein, refers to a process that generates reactive groups at the surface of a substrate, e.g., a base support or an outermost layer of a multi-layered structure. Activation may be accomplished using silanization or plasma ashing. While the figures do not depict a separate silanized layer or —OH groups from plasma ashing, it is to be understood that activation generates a silanized layer or —OH groups at the surface of the activated support or layer to covalently attach the polymeric hydrogel to the underlying support or layer.

An aldehyde, as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

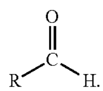

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

The term "altering" when used in conjunction with a single primer set (initial primer set) means that some of the primers within the single primer set are exposed to processing that changes the primers so that they are different from the primers within the single primer set. In one example, some of the primers within the single primer set are removed and replaced with primers having orthogonal cleaving chemistry to the primers in the single primer set. In another example, some of the primers within the single primer set are exposed to a 3' end unblocking/deblocking treatment, followed by an exonuclease treatment, followed by extension activity in order to introduce cleaving chemistry that is orthogonal to the cleaving chemistry of the primers in the single primer set. In still another example, the primers in the single primer set do not have any linearization chemistry, and these different sections of the single primer set are sequentially exposed to extension activity in order to introduce the orthogonal cleaving chemistry.

An "amine" or "amino" functional group refers to an —$NR_aR_b$ group, where $R_a$ and $R_b$ are each independently selected from hydrogen (e.g.,

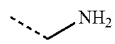

C1-6 alkyl, C2-6 alkenyl, C2-6 alkynyl, C3-7 carbocyclyl, C6-10 aryl, 5-10 membered heteroaryl, and 5-10 membered heterocycle, as defined herein.

As used herein, the term "attached" refers to the state of two things being joined, fastened, adhered, connected or bound to each other, either directly or indirectly. For example, a nucleic acid can be attached to a functionalized polymer by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —$N_3$.

As used herein, a "bonding region" refers to an area of a patterned structure that is to be bonded to another material, which may be, as examples, a spacer layer, a lid, another patterned structure, etc., or combinations thereof (e.g., a spacer layer and a lid, or a spacer layer and another patterned structure). The bond that is formed at the bonding region may be a chemical bond (as described above), or a mechanical bond (e.g., using a fastener, etc.).

As used herein, "carbocycle" means a non-aromatic cyclic ring or ring system containing only carbon atoms in the ring system backbone. When the carbocycle is a ring system, two or more rings may be joined together in a fused, bridged or spiro-connected fashion. Carbocycles may have any degree of saturation, provided that at least one ring in a ring system is not aromatic. Thus, carbocycles include cycloalkyls, cycloalkenyls, and cycloalkynyls. The carbocycle group may have 3 to 20 carbon atoms. Examples of carbocycle rings include cyclopropyl, cyclobutyl, cyclopentyl, cyclohexyl, cyclohexenyl, 2,3-dihydro-indene, bicyclo [2.2.2]octanyl, adamantyl, and spiro[4.4]nonanyl.

As used herein, the term "carboxylic acid" or "carboxyl" as used herein refers to —COOH.

As used herein, "cycloalkylene" means a fully saturated carbocycle ring or ring system that is attached to the rest of the molecule via two points of attachment.

As used herein, "cycloalkenyl" or "cycloalkene" means a carbocycle ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocycle ring or ring system with at least one heteroatom in ring backbone, having at least one double bond, wherein no ring in the ring system is aromatic.

As used herein, "cycloalkynyl" or "cycloalkyne" means a carbocycle ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocycle ring or ring system with at least one heteroatom in ring backbone, having at least one triple bond, wherein no ring in the ring system is aromatic.

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a base support or a layer of a multi-layer stack having a surface opening that is at least partially surrounded by interstitial region(s) of the base support or a layer of a multi-layer stack. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. The depression may also have more complex architectures, such as ridges, step features, etc.

The term "each," when used in reference to a collection of items, is intended to identify an individual item in the collection, but does not necessarily refer to every item in the collection. Exceptions can occur if explicit disclosure or context clearly dictates otherwise.

The term "epoxy" (also referred to as a glycidyl or oxirane group) as used herein refers to

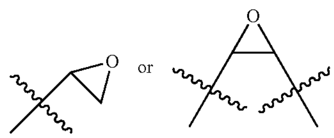

As used herein, the term "flow cell" is intended to mean a vessel having a flow channel where a reaction can be carried out, an inlet for delivering reagent(s) to the flow channel, and an outlet for removing reagent(s) from the flow channel. In some examples, the flow cell accommodates the detection of the reaction that occurs in the flow cell. For example, the flow cell can include one or more transparent surfaces allowing for the optical detection of arrays, optically labeled molecules, or the like.

As used herein, a "flow channel" or "channel" may be an area defined between two bonded components, which can selectively receive a liquid sample. In some examples, the flow channel may be defined between two patterned structures, and thus may be in fluid communication with surface chemistry of the patterned structures. In other examples, the flow channel may be defined between a patterned structure and a lid, and thus may be in fluid communication with surface chemistry of the patterned structures.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocycle" means a non-aromatic cyclic ring or ring system containing at least one heteroatom in the ring backbone. Heterocycles may be joined together in a fused, bridged or spiro-connected fashion. Heterocycles may have any degree of saturation provided that at least one ring in the ring system is not aromatic. In the ring system, the heteroatom(s) may be present in either a non-aromatic or aromatic ring. The heterocycle group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a $—NHNH_2$ group.

As used herein, the term "hydrazone" or "hydrazonyl" as used herein refers to a

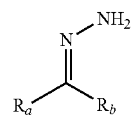

group in which $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocycle, as defined herein.

As used herein, "hydroxy" or "hydroxyl" refers to an —OH group.

As used herein, the term "interstitial region" refers to an area, e.g., of a base support or a layer of a multi-layer stack that separates depressions (concave regions). For example, an interstitial region can separate one depression of an array from another depression of the array. The two depressions that are separated from each other can be discrete, i.e., lacking physical contact with each other. In many examples, the interstitial region is continuous, whereas the depressions are discrete, for example, as is the case for a plurality of depressions defined in an otherwise continuous surface. In other examples, the interstitial regions and the features are discrete, for example, as is the case for a plurality of depressions in the shape of trenches, which are separated by respective interstitial regions. The separation provided by an interstitial region can be partial or full separation. Interstitial regions may have a surface material that differs from the surface material of the depressions. For example, depressions can have a polymer and primer set(s) therein, and the interstitial regions can be free of polymer and primer set(s).

As used herein, a "negative photoresist" refers to a light sensitive material in which a portion that is exposed to light of particular wavelength(s) becomes insoluble to a developer. In these examples, the insoluble negative photoresist has less than 5% solubility in the developer. With the negative photoresist, the light exposure changes the chemical structure so that the exposed portions of the material becomes less soluble (than non-exposed portions) in the developer. While not soluble in the developer, the insoluble negative photoresist may be at least 99% soluble in a remover that is different from the developer. The remover may be a solvent or solvent mixture used, e.g., in a lift-off process.

In contrast to the insoluble negative photoresist, any portion of the negative photoresist that is not exposed to light is at least 95% soluble in the developer. In some examples, the portion of the negative photoresist not exposed to light is at least 98%, e.g., 99%, 99.5%, 100%, soluble in the developer.

"Nitrile oxide," as used herein, means a "$R_aC{\equiv}N^+O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a

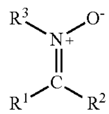

group in which $R^1$, $R^2$, and $R^3$ may be any of the $R_a$ and $R_b$ groups defined herein, except that $R^3$ is not hydrogen (H).

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

In some examples, the term "over" may mean that one component or material is positioned directly on another component or material. When one is directly on another, the two are in contact with each other. In other examples, the term "over" may mean that one component or material is positioned indirectly on another component or material. By indirectly on, it is meant that a gap or an additional component or material may be positioned between the two components or materials.

A "patterned resin" refers to any polymer that can have depressions defined therein. In some of the examples disclosed herein, the patterned resin may have portions that are ultraviolet light absorbing and other portions that are ultraviolet light transmissive depending, in part, upon the thickness. Specific examples of resins and techniques for patterning the resins will be described further below.

A "patterned structure" refers to a single layer base support that includes, or a multi-layer stack with a layer that includes, surface chemistry in a pattern, e.g., in depressions. The surface chemistry may include a polymeric hydrogel and the primer sets disclosed herein, which may, e.g., be used for library template capture and amplification.

As used herein, the term "polyhedral oligomeric silsesquioxane" refers to a chemical composition that is a hybrid intermediate (e.g., $RSiO_{1.5}$) between that of silica ($SiO_2$) and silicone ($R_2SiO$). An example of polyhedral oligomeric silsesquioxane may be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for a polyhedral oligomeric silsesquioxane include epoxy, azide/azido, a thiol, a poly(ethylene glycol), a norbornene, a tetrazine, acrylates, and/or methacrylates, or further, for example, alkyl, aryl, alkoxy, and/or haloalkyl groups.

As used herein, a "positive photoresist" refers to a light sensitive material in which a portion that is exposed to light of particular wavelength(s) becomes soluble to a developer. In these examples, any portion of the positive photoresist exposed to light is at least 95% soluble in the developer. In some examples, the portion of the positive photoresist exposed to light is at least 98%, e.g., 99%, 99.5%, 100%, soluble in the developer. With the positive photoresist, the light exposure changes the chemical structure so that the exposed portions of the material become more soluble (than non-exposed portions) in the developer.

In contrast to the soluble positive photoresist, any portion of the positive photoresist not exposed to light is insoluble (less than 5% soluble) in the developer. While not soluble in the developer, the insoluble positive photoresist may be at least 99% soluble in a remover that is different from the developer. In some examples, the insoluble positive photoresist is at least 98%, e.g., 99%, 99.5%, 100%, soluble in the remover. The remover may be a solvent or solvent mixture used in a lift-off process.

As used herein, the "primer" is defined as a single stranded nucleic acid sequence (e.g., single strand DNA). Some primers, referred to herein as amplification primers, serve as a starting point for template amplification and cluster generation. Other primers, referred to herein as sequencing primers, serve as a starting point for DNA synthesis. The 5' terminus of the primer may be modified to allow a coupling reaction with a functional group of a polymer. The primer length can be any number of bases long and can include a variety of non-natural nucleotides. In an example, the sequencing primer is a short strand, ranging from 10 to 60 bases, or from 20 to 40 bases. The term "pre-primer" is used herein to describe i) a truncated primer that is exposed to additional processing to generate the full primer, or ii) a primer having a photocleavable blocking group positioned from 5 bases to 10 bases from 3' end so that a truncated primer is generated during processing and is subsequently used to generate the full primer. Additionally, a cleavable primer includes a cleavage site while an uncleavable primer does not include a cleavage site.

The phrase "single primer set" refers to a plurality of primers that includes two different single stranded nucleic acid sequences or to a plurality of pre-primers that includes two different truncated single stranded nucleic acid sequences or to a plurality of pre-primers that includes two different primers having a photocleavable blocking group positioned from 5 bases to 10 bases from 3' end.

A "spacer layer," as used herein, refers to a material that bonds two components together. In some examples, the spacer layer can be a radiation absorbing material that aids in bonding, or can be put into contact with a radiation absorbing material that aids in bonding.

The term "substrate" refers to the single layer base support or a multi-layer structure upon which surface chemistry is introduced.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

The term "transparent" refers to a material, e.g., in the form of a base support or layer, that is capable of transmitting a particular wavelength or range of wavelengths. For example, the material may be transparent to wavelength(s) that are used to chemically change a positive or negative photoresist and/or to remove a 3' blocking group. Transparency may be quantified using transmittance, i.e., the ratio of light energy falling on a body to that transmitted through the body. The transmittance of a transparent base support or a transparent layer will depend upon the thickness of the base support or layer, the wavelength of light, and the dosage of the light to which it is exposed. In the examples disclosed herein, the transmittance of the transparent base support or the transparent layer may range from 0.25 (25%) to 1 (100%). As an example, tantalum pentoxide (the inorganic compound with the formula $Ta_2O_5$) is considered transparent, as it has a transmittance ranging from about 0.25 (25%) to 1 (100%) to wavelengths ranging from about 0.35 μm (350 nm) to at least 1.8 μm (1800 nm). The material of the base support or layer may be a pure material, a material with some impurities, or a mixture of materials, as long as the resulting base support or layer is capable of the desired transmittance. Additionally, depending upon the transmittance of the base support or layer, the time for light exposure and/or the output power of the light source may be increased or decreased to deliver a suitable dose of light energy through the transparent base support and/or layer to achieve the desired effect (e.g., generating a soluble or insoluble photoresist, removing a 3' blocking group, etc.).

Substrate Configurations

In each of the methods disclosed herein, the substrate functions, either alone or in combination with a separate UV light blocking layer, as a patterning tool that enables the selective alteration of the single primer set attached to the polymeric hydrogel within depressions of the substrate. Different examples are shown in FIG. 1A through FIG. 1D.

In the examples of FIG. 1A, FIG. 1B, and FIG. 1C, the substrates 10A, 10B, 10C are single layer base supports that include depressions 12 separated by interstitial regions 14. In these examples, the substrate 10A, 10B, 10C may be any material that is capable of transmitting the ultraviolet light that is to be used in the alteration of the single primer set. In one example, the substrate 10A, 10B, 10C is capable of transmitting ultraviolet light that can remove a 3' end blocking group from exposed primers of the single primer set. In another example, the substrate 10A, 10B, 10C is capable of transmitting ultraviolet light that can pattern a photoresist that overlies the substrate 10A, 10B, 10C. In some instances, the substrate material may also be capable of transmitting visible light that is to be used in nucleic acid sequencing.

In these particular examples, suitable materials for the substrate 10A, 10B, 10C include siloxanes, glass, modified or functionalized glass, plastics (including acrylics, polyethylene terephthalate (PET), polycarbonate, cyclic olefin copolymer (COC), and some polyamides), silica or silicon oxide ($SiO_2$), fused silica, silica-based materials, silicon nitride ($Si_3N_4$), inorganic glasses, resins, or the like. Examples of resins that can transmit UV light include inorganic oxides, such as tantalum pentoxide (e.g., $Ta_2O_5$) or other tantalum oxide(s) ($TaO_x$), aluminum oxide (e.g., $Al_2O_3$), silicon oxide (e.g., $SiO_2$), hafnium oxide (e.g., $HfO_2$), etc., or polymeric resins, such as a polyhedral oligomeric silsesquioxane based resin (e.g., POSS® from Hybrid Plastics), a non-polyhedral oligomeric silsesquioxane epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof. In some examples, the resin used has a UV transmittance (at the predetermined UV dosage being used) that ranges from about 0.5 to about 1, e.g., from about 0.75 to about 1, from about 0.9 to about 0.99. The thickness of the resin can be adjusted so that the entire resin exhibits the desired UV transmittance for the UV dosage being used. In some instances, the resin thickness is 150 nm or less.

Some of the example substrate materials (e.g., inorganic oxides) can be selectively applied via vapor deposition, aerosol printing, or inkjet printing and the depressions 12 can be formed during this process. Other example materials, e.g., the polymeric resins, may be applied and then patterned to form the depressions 12. For example, the polymeric resins may be deposited using a suitable technique, such as chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, etc.

While two depressions 12 are shown in FIG. 1A, FIG. 1B, and FIG. 1C, it is to be understood that many different layouts of the depressions 12 are envisaged, including regular, repeating, and non-regular patterns. In an example, the depressions 12 are disposed in a hexagonal grid for close packing and improved density. Other layouts may include, for example, rectangular layouts, triangular layouts, and so forth. In some examples, the layout or pattern can be an x-y format in rows and columns. In some other examples, the layout or pattern can be a repeating arrangement of the depressions 12 and the interstitial regions 14. In still other examples, the layout or pattern can be a random arrangement of the depressions 12 and the interstitial regions 14.

The layout or pattern may be characterized with respect to the density (number) of the depressions 12 in a defined area. For example, the depressions 12 may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density can be between one of the lower values and one of the upper values selected from the ranges above, or that other densities (outside of the given ranges) may be used. As examples, a high density array may be characterized as having the depressions 12 separated by less than about 100 nm, a medium density array may be characterized as having the depressions 12 separated by about 400 nm to about 1 μm, and a low density array may be characterized as having the depressions 12 separated by greater than about 1 μm.

The layout or pattern of the depressions 12 may also or alternatively be characterized in terms of the average pitch, or the spacing from the center of one depression 12 to the center of an adjacent depression 12 (center-to-center spacing) or from the right edge of one depression 12 to the left edge of an adjacent depression 12 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.15 μm, about 0.5 μm, about 1 μm, about 5 μm, about 10 μm, about 100 μm, or more or less. The average pitch for a particular pattern of can be between one of the lower values and one of the upper values selected from the ranges above. In an example, the depressions 12 have a pitch (center-to-center spacing) of about 1.5 μm. While example average pitch values have been provided, it is to be understood that other average pitch values may be used.

The size of each depression 12 may be characterized by its volume, opening area, depth, and/or diameter. For example, the volume can range from about $1\times10^{-3}$ $\mu m^3$ to about 100 $\mu m^3$, e.g., about $1\times10^{-2}$ $\mu m^3$, about 0.1 $\mu m^3$, about 1 $\mu m^3$, about 10 $\mu m^3$, or more, or less. For another example, the opening area can range from about $1\times10^{-3}$ $\mu m^2$ to about 100 $\mu m^2$, e.g., about $1\times10^{-2}$ $\mu m^2$, about 0.1 $\mu m^2$, about 1 $\mu m^2$, at least about 10 $\mu m^2$, or more, or less. For still another example, the depth can range from about 0.1 μm to about 100 μm, e.g., about 0.5 μm, about 1 μm, about 10 μm, or more, or less. For another example, the depth can range from about 0.1 μm to about 100 μm, e.g., about 0.5 μm, about 1 μm, about 10 μm, or more, or less. For yet another example, the diameter or length and width can range from about 0.1 μm to about 100 μm, e.g., about 0.5 μm, about 1 μm, about 10 μm, or more, or less.

Each of the examples shown in FIG. 1A, FIG. 1B, and FIG. 1C includes the separate UV light blocking layer 16 or 16' positioned over or embedded in a portion of the depression 12. In any of these examples, the UV light blocking layer 16, 16' may be any material that is capable of absorbing the ultraviolet light that is to be used in the alteration of the single primer set. In some instances, the UV light blocking layer 16, 16' may also be capable of transmitting visible light that is to be used in nucleic acid sequencing. In these instances, the UV light blocking layer 16, 16' may remain as a component of the flow cell as opposed to being removed from the flow cell.

The material and/or the thickness of the material of the UV light blocking layer 16, 16' is selected so that the layer 16, 16' blocks at least 75% of UV light that is transmitted through the substrate 10A, 10B, 10C (e.g., introduced from the side 18A, 18B, 18C) from reaching an overlying material that is positioned directly in line with the UV light blocking layer 16, 16'. The material used to form the UV light blocking layer 16, 16' may be titanium, chromium, aluminum, gold, or copper. In some examples, the metal material may be at least substantially pure (<99% pure). In other examples, molecules or compounds of the listed elements or other elements may be used as long as the UV light blocking layer 16, 16' is opaque (non-transparent or having transmittance less than 0.25) to the UV light being used in the alteration of the single primer set. For example, oxides of any of the listed metals (e.g., titanium dioxide, copper oxide, iron oxide, cobalt oxide, etc.) may be used, alone or in combination with the listed metal. Other oxides, such as zinc oxide or cerium oxide may also be used, depending upon the UV wavelength that is to be used (and thus blocked by the material). Titanium dioxide, zinc oxide, and cerium oxide are examples of materials that are capable of UV light absorption and visible light transmission. Still other UV opaque materials include polymer resins that contain UV absorbents, such as organic small molecules (e.g., pyrene), dyes (e.g., ATTO™ 390 from ATTO-tec), selected to absorb the wavelength of UV to be used in the process. In an example, the thickness of the UV light blocking layer 16, 16' is at least 15 nm thick (e.g., 20 nm, 25 nm, 40 nm, etc.). Some metal UV light blocking layers 16, 16' may be thicker, e.g., having a thickness ranging from about 100 nm to about 1000 nm, in order to minimize plasmonic effects through the metal.

Plasmonic effects could unintentionally deblock the primers that overlie the UV light blocking layer 16, 16'. Thus, with the metal UV light blocking layer 16, 16', it may be desirable to include a coating layer that helps to prevent deblocking during backside UV expose (i.e., UV light directed through the substrate 10A, 10B, or 10C from the side 18A, 18B, or 18C). Examples of the coating layer include an organic polymer or metal oxide material having a thickness ranging from about 10 nm to about 300 nm.

In the examples shown in FIG. 1A and FIG. 1B, the separate UV light blocking layer 16 is positioned over a portion of each depression 12. As depicted in each of these figures, the UV light blocking layer 16 is in contact with a portion of the bottom surface 20 of the depression 12. The UV light blocking layer 16 defines a pattern for some of the primers in the single primer set to be altered, and thus the UV light blocking layer 16 may be applied so that it covers a portion of the depression 12, including some of the sidewalls and some of the bottom 20, while leaving another portion of the depression 12 exposed. As shown in FIG. 1B, the UV light blocking layer 16 may also be applied over the interstitial region(s) 14 that is/are adjacent to the depression sidewall(s) being coated. In both FIG. 1A and FIG. 1B, the portion of the substrate 10A, 10B covered by the UV light blocking layer 16 is referred to herein as the first region 58 and the portion of the substrate 10B free of the UV light blocking layer 16 is referred to herein as the second region 60. As will be discussed in reference to some of the methods, the first region 58 corresponds with a predetermined region of a grafted layer where at least some of the primers will be altered.

In the examples shown in FIG. 1A and FIG. 1B, the UV light blocking layer 16 may be fabricated using a photolithography process combined with either a lift-off technique or an etching technique. In other examples, selective deposition techniques, such as chemical vapor deposition (CVD) and variations thereof (e.g., low-pressure CVD or LPCVD), atomic layer deposition (ALD), and masking techniques, may be used to deposit the UV light blocking layer 16 in the desirable areas. Alternatively, the UV light blocking layer 16 may be applied across the substrate 10A, 10B (including over all of the depressions 12), and then selectively removed (e.g., via masking and etching) from the desired portions.

In the example of FIG. 1C, the separate UV light blocking layer 16' is embedded within a portion of each depression 12. By "embedded," it is meant that at least a portion of the UV light blocking layer 16' extends below the bottom surface 20 of the depression 12. In one example, as depicted in FIG. 1C, a surface 22 of the UV light blocking layer 16' is substantially coplanar with the bottom surface 20 of the depression 12, and the rest of the UV light blocking layer 16' extends into the depth of the substrate 10C. In another example (not depicted in the figures), the UV light blocking layer 16' may be completely embedded in the substrate 10C such that all sides of the UV light blocking layer 16', including the surface 22, are covered by the substrate 10C or by additional material layer(s) that separate the UV light blocking layer 16' from the polymeric hydrogel.

The UV light blocking layer 16' defines a pattern for some of the primers in the single primer set to be altered, and thus the UV light blocking layer 16' may be embedded so that it aligns with a portion of the depression 12, while leaving another portion of the depression 12 exposed. In other words, the UV light blocking layer 16' is embedded in a first region 58" of the substrate 10C (in particular, in the depression 12) that corresponds with the predetermined region (of the grafted layer that is to be altered), whereby a second region 60 of the substrate 10C (in particular, in the depression 12) is free of the embedded UV light blocking layer 16'.

In the example shown in FIG. 1C, the area of the substrate 10C where the UV light blocking layer 16' is to be fabricated may be imprinted or otherwise defined when the depression 12 is formed. A selective deposition technique, such as chemical vapor deposition (CVD) and variations thereof (e.g., low-pressure CVD or LPCVD), atomic layer deposition (ALD), and masking techniques, may be used to deposit the UV light blocking layer 16' in the desirable area. If the UV light blocking layer 16' is to be completely embedded, additional substrate 10C material or additional material layer(s) may be applied over the UV light blocking layer 16'.

Because the UV light blocking layer 16' is embedded within the substrate 10C, it may be desirable to select a material that can block the UV light used in primer set alteration and that can transmit visible light used in sequencing. As noted above, some examples of these materials include titanium dioxide, zinc oxide, and cerium oxide. It is to be understood that these materials may be used for the UV light blocking layer 16 (shown in FIG. 1A and FIG. 1B), and thus these examples of the UV light blocking layer 16 may remain in the final flow cell without deleteriously affecting sequencing.

In any examples where it is desirable to keep the UV light blocking layer 16, 16' in the final flow cell, the UV light blocking layer 16, 16' may be coated with silicon dioxide, tantalum pentoxide, or any of the polymeric resins, each of which can be activated to enable covalent attachment to the polymeric hydrogel. One or more of these materials may be used as the additional material layer(s) to embed the UV light blocking layer 16' in the substrate 10C. These additional material layer(s) may have a total thickness ranging from about 10 nm to about 300 nm.

The example of the substrate 10D shown in FIG. 1D does not include the UV light blocking layer 16, 16'. Rather, the substrate 10D has varying thicknesses $t_1$, $t_2$, $t_3$, some of which (e.g., $t_1$) are capable of transmitting the ultraviolet light that is to be used in the alteration of the single primer set and others of which (e.g., $t_2$, $t_3$) are capable of absorbing, and thus blocking, the ultraviolet light that is to be used in the alteration of the single primer set. The ultraviolet light transparent portions of the substrate 10D are shown at reference numeral 60' and the ultraviolet light blocking portions of the substrate 10D are shown at reference numeral 58'.

In this example, the substrate 10D may be any resin material whose UV absorbance, when exposed to a particular UV light dosage, can be altered by adjusting its thickness. Any of the previously listed resins may be used so long as thicker portions (e.g., those having thicknesses $t_2$ and $t_3$) absorb the UV light and thinner portions (e.g., those having thickness $t_1$) transmit a desirable amount of UV light for primer set alteration when the resin is exposed to a predetermined UV light dosage through the side 18D. In one example, a polyhedral oligomeric silsesquioxane based resin having thicker portions of about 500 nm and thinner portions of about 150 nm will respectively and effectively absorb and transmit UV light when exposed to a dosage ranging from about 30 mJ/cm$^2$ to about 60 mJ/cm$^2$. Other thicknesses may be used, and the UV dosage may be adjusted accordingly to achieve the desired absorption in thicker areas and transmittance in thinner areas.

The correlation between UV dose, UV absorption constant, and substrate 10C thickness can be expressed as:

$$D_0 = D \times \exp(-kd)$$

where $D_0$ is the required UV dose to alter the single primer set, D is the actual UV dose which has to be applied to the substrate 10D, k is the absorption constant, and d is the thickness of thinner portion of the substrate 10D. Thus, the actual UV dose (D) can be expressed as:

$$D = D_0/\exp(-kd)$$

The varying thicknesses $t_1$, $t_2$ respectively align with different portions 24, 26 of a multi-depth depression 12' defined in the substrate 10D, and the thickness $t_3$ aligns with the interstitial regions 14 that are adjacent to the multi-depth depression 12'. The portion 24 is a deep portion of the multi-depth depression 12' and the portion 26 is a shallow portion of the multi-depth depression 12'. As used herein, the terms "deep portion" and "shallow portion" refer to three-dimensional (3D) spaces within the multi-depth depression 12'. The deep portion 24 has a greater depth than the shallow portion 26, as measured, e.g., from an opening of the multi-depth depression 12'.

The substrates 10A, 10B, 10C, 10D shown in FIG. 1A through FIG. 1D are depicted as single layer base supports. In other examples, the substrates 10A, 10B, 10C, 10D (having the depressions 12 or 12' defined therein) may be the top layer of a multi-layer structure. In these instances, the substrates 10A, 10B, 10C, 10D may be positioned on an underlying base support that is capable of transmitting the ultraviolet light that is to be used in the alteration of the single primer set. In some instances, this underlying base support is also capable of transmitting the visible light that is to be used in nucleic acid sequencing. In one example of such a multi-layer structure, the substrate 10A, 10B, 10B, 10D is a patterned resin supported by glass.

Polymeric Hydrogel

The substrates 10A, 10B, 10C with the UV light blocking layer 16, 16' and the substrate 10D with the varying thicknesses $t_1$, $t_2$, $t_3$ may be used in different examples of the method, each of which uses a single polymeric hydrogel.

The polymeric hydrogel (shown, for example, at reference numeral 28 in FIG. 2A) may be any gel material that can swell when liquid is taken up and can contract when liquid is removed, e.g., by drying. In an example, the polymeric hydrogel includes an acrylamide copolymer. Some examples of the acrylamide copolymer are represented by the following structure (I):

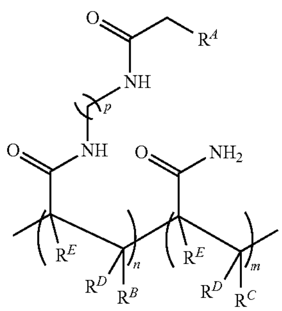

wherein:

- $R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;
- $R^B$ is H or optionally substituted alkyl;
- $R^C$, $R^D$, and $R^E$ are each independently selected from the group consisting of H and optionally substituted alkyl;
- each of the $—(CH_2)_p—$ can be optionally substituted;
- p is an integer in the range of 1 to 50;
- n is an integer in the range of 1 to 50,000; and
- m is an integer in the range of 1 to 100,000.

One specific example of the acrylamide copolymer represented by structure (I) is poly(N-(5-azidoacetamidylpentyl) acrylamide-co-acrylamide, PAZAM.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the acrylamide copolymer may range from about 5 kDa to about 1500 kDa or from about 10 kDa to about 1000 kDa, or may be, in a specific example, about 312 kDa.

In some examples, the acrylamide copolymer is a linear polymer. In some other examples, the acrylamide copolymer is a lightly cross-linked polymer.

In other examples, the gel material may be a variation of structure (I). In one example, the acrylamide unit may be replaced with N,N-dimethylacrylamide ( 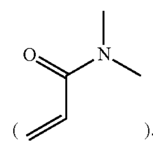 ).

In this example, the acrylamide unit in structure (I) may be replaced with,

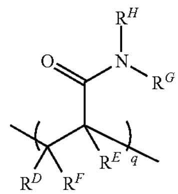

where $R^D$, $R^E$, and RF are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

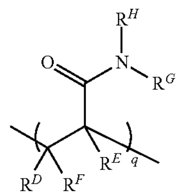

in addition to the recurring "n" and "m" features, where $R^D$, $R^E$, and RF are each H or a C1-C6 alkyl, and $R^G$ and $R^H$ are each a C1-C6 alkyl. In this example, q may be an integer in the range of 1 to 100,000.

As another example of the polymeric hydrogel, the recurring "n" feature in structure (I) may be replaced with a monomer including a heterocyclic azido group having structure (II):

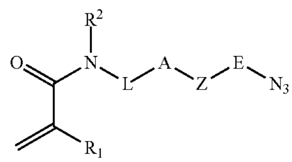

wherein $R_1$ is H or a C1-C6 alkyl; $R^2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 carbon-containing ring members present as a single cyclic structure or a fused structure. Some specific examples of Z include pyrrolidinyl, pyridinyl, or pyrimidinyl. As still another example, the gel material may include a recurring unit of each of structure (III) and (IV):

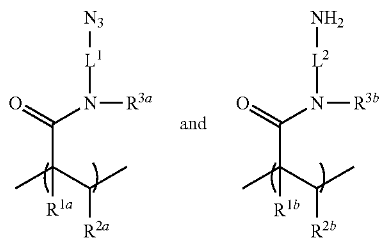

and wherein each of $R^{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

In still another example, the acrylamide copolymer is formed using nitroxide mediated polymerization, and thus at least some of the copolymer chains have an alkoxyamine end group. In the copolymer chain, the term "alkoxyamine end group" refers to the dormant species —$ONR_1R_2$, where each of $R_1$ and $R_2$ may be the same or different, and may independently be a linear or branched alkyl, or a ring structure, and where the oxygen atom is attached to the rest of the copolymer chain. In some examples, the alkoxyamine may also be introduced into some of the recurring acrylamide monomers, e.g., at position $R^A$ in structure (I). As such, in one example, structure (I) includes an alkoxyamine end group; and in another example, structure (I) includes an alkoxyamine end group and alkoxyamine groups in at least some of the side chains.

It is to be understood that other molecules may be used to form the polymeric hydrogel, as long as they are capable of being functionalized with the desired chemistry, e.g., the single primer set. Some examples of suitable materials for the polymeric hydrogel include functionalized silanes, such as norbornene silane, azido silane, alkyne functionalized silane, amine functionalized silane, maleimide silane, or any other silane having functional groups that can respectively attach the desired chemistry. Still other examples of suitable materials for polymeric hydrogel include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable materials for the polymeric hydrogel include mixed copolymers of acrylamides and acrylates. A variety of polymer architectures containing acrylic monomers (e.g., acrylamides, acrylates etc.) may be utilized in the examples disclosed herein, such as branched polymers, including dendrimers (e.g., multi-arm or star polymers), star-shaped or star-block polymers, and the like. For example, the monomers (e.g., acrylamide, acrylamide containing the catalyst, etc.) may be incorporated, either randomly or in block, into the branches (arms) of a dendrimer.

The gel material for the polymeric hydrogel may be formed using any suitable copolymerization process, such as nitroxide mediated polymerization (NMP), reversible addition-fragmentation chain-transfer (RAFT) polymerization, etc.

The attachment of the polymeric hydrogel to the underlying substrate 10A, 10B, 10C, 10D may be through covalent bonding. In some instances, the underlying substrate 10A, 10B, 10C, 10D may first be activated, e.g., through silanization or plasma ashing. Covalent linking is helpful for maintaining the primers in the desired regions throughout the lifetime of the flow cell during a variety of uses.

Methods

The substrates 10A, 10B, 10C with the UV light blocking layer 16, 16' and the substrate 10D with the varying thicknesses $t_1$, $t_2$, $t_3$ may be used in different examples of the method, each of which involves the alteration of a single primer set. Different examples of the method are shown in the series of figures set forth in FIG. 3 through FIG. 7.

The methods shown in the series of figures set forth in FIG. 3 through FIG. 6 generally include applying a polymeric hydrogel 28 to a surface of a substrate 10A, 10B, 10C, or 10D including depressions 12 or 12' separated by interstitial regions 14; before or after the polymeric hydrogel 28 is applied, grafting a primer set 30 or 30' to the polymeric hydrogel 28 to form a grafted layer 32 or 32', the primer set 30 or 30' including cleavable first primers 34 or 34" and uncleavable second primers 36 or 36"; and at a predetermined region 38 of the grafted layer 32 or 32' within a portion of at least some of the depressions 12 or 12', altering some of the cleavable first primers 34 or 34" and some of the uncleavable second primers 36 or 36" to respectively introduce cleavable second primers 40 or 40" and uncleavable first primers 42 or 42".

The method shown in the series of figures set forth in FIG. 7 generally includes applying a polymeric hydrogel 28 to a surface of a substrate 10A, 10B, or 10C including depressions 12 separated by interstitial regions 14, each depression 12 including an ultraviolet light blocking layer 16' positioned at a first region and a second region that is transparent to ultraviolet light and that is adjacent to the first region; before or after applying the polymeric hydrogel 28, grafting a primer set 30" to the polymeric hydrogel 28 to form a grafted layer 32", the primer set 30" including 3' blocked uncleavable first pre-primers 46 and 3' blocked uncleavable second pre-primers 48; removing the polymeric hydrogel 28 or the grafted layer 32" from the interstitial regions 14; at a first predetermined region 38 of the grafted layer 32" within the second region of at least some of the depressions 12: altering 3' blocked uncleavable first pre-primers 46 to introduce cleavable first primers 34; and altering the 3' blocked uncleavable second pre-primers 48 to introduce uncleavable second primers 36; and at a second predetermined region 38' of the grafted layer 32" within the first region of at least some of the depressions 12: altering 3' blocked uncleavable first pre-primers 46 to introduce uncleavable first primers 42; and altering the 3' blocked uncleavable second pre-primers 48 to introduce cleavable second primers 40.

Any example of the pre-primers 46, 48 disclosed herein may be used in this example method.

Figure 2A:
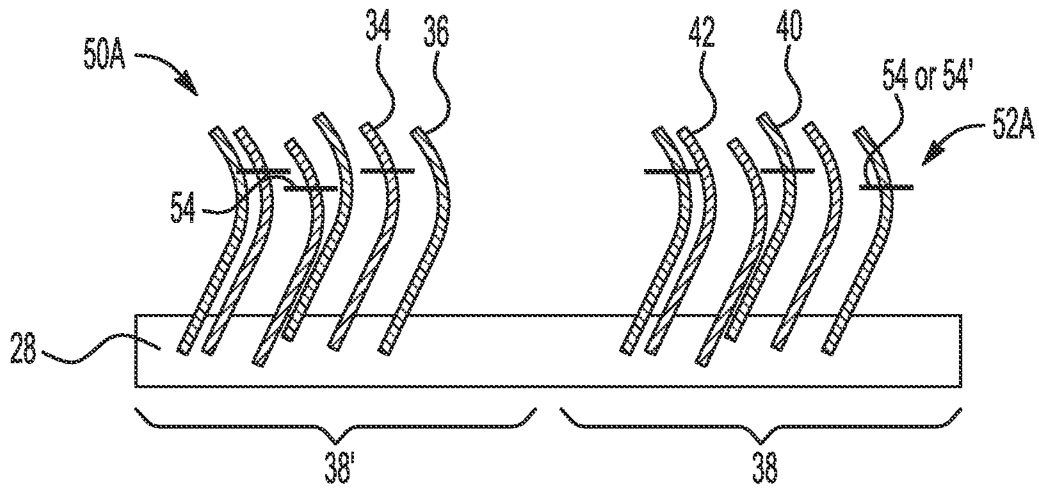
FIG. 2A is a schematic view of an example primer set that is used in some examples of the flow cells disclosed herein.
Figure 2B:
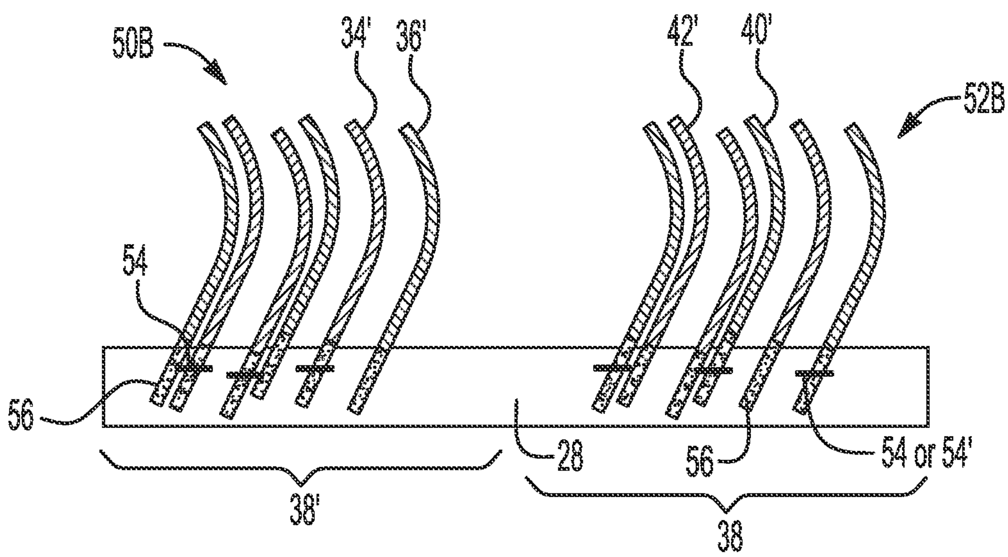
FIG. 2B is a schematic view of another example primer set that is used in some examples of the flow cells disclosed herein.

Before each of the methods is described in more detail in reference to the individual series of figures, the cleavable and uncleavable primers are generally described in reference to FIG. 2A and FIG. 2B. At the outset of each method, a single primer set, e.g., 30 or 30' (not shown in FIG. 2A or FIG. 2B) is attached to the polymeric hydrogel 28. At one or more regions of the grafted layer 32, 32', the initial primer set 30, 30' is altered using the methods disclosed herein. The result of the alteration(s) is two primer sets 50A, 52A (FIG. 2A) or 50B, 52B (FIG. 2B).

The primers sets 50A, 52A or 50B, 52B (i.e., those altered by one of the methods disclosed herein) are related in that one set 50A, 50B includes a cleavable first primer 34, 34' and an uncleavable second primer 36, 36' and the other set 52A, 52B includes an uncleavable first primer 42, 42' and a cleavable second primer 40, 40'. These primer sets 50A, 52A or 50B, 52B allow a single template strand to be amplified and clustered across both primer sets 50A, 52A or 50B, 52B, and also enable the generation of forward and reverse strands on adjacent regions 38, 38' of the polymeric hydrogel 28 (or grafted layer 32, 32') due to the cleavage groups 54 (FIG. 2A) or 54, 54' (FIG. 2B) being present on the opposite primers of the sets 50A, 52A or 50B, 52B. It is to be understood that the prime (') designations for the primers 34', 36', 40', 42' do not refer to complementary sequences to the primers 34, 36, 40, 42, but rather are additional examples of the type of primer.

Each of the first primer sets 50A, 50B includes a cleavable first primer 34 or 34' and an uncleavable second primer 36 or 36'; and each of the second primer sets 52A, 52B includes an uncleavable first primer 42 or 42' and a cleavable second primer 40 or 40'.

The uncleavable second primer 36 or 36' and the cleavable first primer 34 or 34' are oligonucleotide pairs, e.g., where the uncleavable second primer 36 or 36' is a forward amplification primer and the cleavable first primer 34 or 34' is a reverse amplification primer or where the uncleavable second primer 36 or 36' is the forward amplification primer and the cleavable first primer 34 or 34' is the reverse amplification primer. In each example of the primer set 50A, 50B, the cleavable first primer 34 or 34' includes a cleavage site 54, while the uncleavable second primer 36 or 36' does not include a cleavage site 54.

The cleavable second primer 40 or 40' and the uncleavable first primer 42 or 42' are also oligonucleotide pairs, e.g., where the cleavable second primer 40 or 40' is a forward amplification primer and the uncleavable first primer 42 or 42' is a reverse amplification primer or where the uncleavable first primer 42 or 42' is the forward amplification primer and the cleavable second primer 40 or 40' is the reverse amplification primer. In each example of the second primer set 52A, 52B, the cleavable second primer 40 or 40' includes a cleavage site 54 or 54', while the uncleavable first primer 42 or 42' does not include a cleavage site 54 or 54'.

It is to be understood that the uncleavable second primer 36 or 36' of the first primer set 50A, 50B and the cleavable second primer 40 or 40' of the second primer set 52A, 52B, have the same nucleotide sequence (e.g., both are forward amplification primers), except that the cleavable second primer 40 or 40' includes the cleavage site 54 or 54' integrated into the nucleotide sequence or into a linker 56 attached to the nucleotide sequence. Similarly, the cleavable first primer 34 or 34' of the first primer set 50A, 50B and the uncleavable first primer 42 or 42' of the second primer set 52A, 52B have the same nucleotide sequence (e.g., both are reverse amplification primers), except that the cleavable first primer 34 or 34' includes the cleavage site 54 integrated into the nucleotide sequence or into a linker 56 attached to the nucleotide sequence.

It is to be understood that when the first primers 34 and 42 or 34' and 42' are forward amplification primers, the second primers 36 and 40 or 36' and 40' are reverse primers, and vice versa.

The uncleavable primers 36, 42 or 36', 42' may be any primers with a universal sequence for capture and/or amplification purposes, such as P5 and P7 primers, or any combination of PA, PB, PC, and PD primers (e.g., PA and PB or PA and PD, etc.).

Examples of the P5 and P7 primers are used on the surface of commercial flow cells sold by Illumina Inc. for sequencing, for example, on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms. The uncleavable P5 primer is:

uncleavable P5: 5'→3'

(SEQ. ID. NO. 1)
AATGATACGGCGACCACCGAGACTACAC

The uncleavable P7 primer may be any of the following:

uncleavable P7 #1: 5'→3'

(SEQ. ID. NO. 2)
CAAGCAGAAGACGGCATACGAAT uncleavable P7 #2: 5'→3'

(SEQ. ID. NO. 3)
CAAGCAGAAGACGGCATACAGAT

The other uncleavable primers (PA-PD) mentioned above include:

uncleavable PA 5'→3'

(SEQ. ID. NO. 4)
GCTGGCACGTCCGAACGCTTCGTTAATCCGTTGAG cPA (PA') 5'→3'

(SEQ. ID. NO. 5)
CTCAACGGATTAACGAAGCGTTCGGACGTGCCAGC uncleavable PB 5'→3'

(SEQ. ID. NO. 6)
CGTCGTCTGCCATGGCGCTTCGGTGGATATGAACT cPB (PB') 5'→3'

(SEQ. ID. NO. 7)
AGTTCATATCCACCGAAGCGCCATGGCAGACGACG uncleavable PC 5'→3'

(SEQ. ID. NO. 8)
ACGGCCGCTAATATCAACGCGTCGAATCCGCAACT cPC (PC') 5'→3'

(SEQ. ID. NO. 9)
AGTTGCGGATTCGACGCGTTGATATTAGCGGCCGT uncleavable PD 5'→3'

(SEQ. ID. NO. 10)
GCCGCGTTACGTTAGCCGGACTATTCGATGCAGC cPD (PD') 5'→3'

(SEQ. ID. NO. 11)
GCTGCATCGAATAGTCCGGCTAACGTAACGCGGC

These primers are uncleavable primers 36, 42 or 36', 42' because they do not include a cleavage site 54, 54'. It is to be understood that any suitable universal sequence can be used as the uncleavable primers 36, 42 or 36', 42'.

Examples of cleavable primers 34, 40 or 34', 40' include the P5 and P7 primers or other universal sequence primers (e.g., the PA, PB, PC, PD primers) with the respective cleavage sites 54, 54', incorporated into the respective nucleic acid sequences (FIG. 2A), or into the linker 56 that attaches the cleavable primers 34, 40 or 34', 40' to the polymeric hydrogel 28 (FIG. 2B). Examples of suitable cleavage sites 54, 54' include enzymatically cleavable nucleobases or chemically cleavable nucleobases, modified nucleobases, or linkers (e.g., between nucleobases), as described herein. Some specific examples of the cleavage sites 54, 54' include uracil, 8-oxoguanine, allyl-T (a thymine nucleotide analog having an allyl functionality). The cleavage sites 54, 54' may be incorporated at any point in the strand.

One specific example of the cleavable primers 34, 40 or 34', 40' is shown below, where the cleavage site is shown at "n":

cleavable P5: 5'→3'

(SEQ. ID. NO. 12)
AATGATACGGCGACCACCGAGAnCTACAC wherein "n" is allyl T.

The cleavable P7 primer may be any of the following:

P7 #1: 5'→3'

(SEQ. ID. NO. 13)
CAAGCAGAAGACGGCATACGAnAT

P7 #2: 5'→3'

(SEQ. ID. NO. 14)
CAAGCAGAAGACGGCATACnAGAT

P7 #3: 5'→3'

(SEQ. ID. NO. 15)
CAAGCAGAAGACGGCATACnAnAT where "n" is 8-oxoguanine in each of the sequences. Still another example of cleavable P5 is:

cleavable P5: 5'→3'

(SEQ. ID. NO. 16)
AATGATACGGCGACCACCGAGAUCTACAC where uracil is the cleavage site.

In any of the examples disclosed herein, the initial primer set 30, 30' may also include a PX primer for capturing a library template seeding molecule. The density of the PX motifs should be relatively low in order to minimize polyclonality within each depression 12, 12'. The PX capture primers may be:

PX 5'→3'

(SEQ. ID. NO. 17)
AGGAGGAGGAGGAGGAGGAGGAGG cPX (PX') 5'→3'

(SEQ. ID. NO. 18)
CCTCCTCCTCCTCCTCCTCCTCCT

FIG. 2A and FIG. 2B depict different configurations of the primer sets 50A, 52A, 50B, 52B attached to the polymeric hydrogel 28. More specifically, FIG. 2A and FIG. 2B depict different configurations of the primers 34, 36 or 34', 36' and 40, 42 or 40', 42' that may be used.

In the example shown in FIG. 2A, the primers 34, 36 and 40, 42 of the primer sets 50A and 52A are directly attached to the polymeric hydrogel 28, for example, without a linker 56. The polymeric hydrogel 28 has surface functional groups that can immobilize the terminal groups at the 5' end of the primers of the initial primer set 30, 30', and thus of the primers 34, 36 and 40, 42 generated using the methods disclosed herein.

Also, in the example shown in FIG. 2A, the cleavage site 54, 54' of each of the cleavable primers 34, 40 is incorporated into the sequence of the primer. It is to be understood that the same type of cleavage site 54 or different types of cleavage sites 54, 54' may be used in the cleavable primers 34, 40 of the respective primer sets 50A, 52A. As an example, the cleavage sites 54 are uracil bases, and the cleavable primers 34, 40 are P5U and P7U, respectively. It is to be understood that any other cleavable nucleotide that can be incorporated by a polymerase may be used as the cleavage site 54. The uracil bases or other cleavage sites may also be incorporated into any of the PA, PB, PC, and PD primers to generate the cleavable primers 34, 40. In this example, the uncleavable primer 36 of the oligonucleotide pair 34, 36 may be P7, and the uncleavable primer 42 of the oligonucleotide pair 40, 42 may be P5. Thus, in this example, the first primer set 50A includes P7, P5U and the second primer set 52A includes P5, P7U. The primer sets 50A, 52A have opposite linearization chemistries, which, after amplification, cluster generation, and linearization, allows forward template strands to be formed in one region 38 of the polymeric hydrogel 28 and reverse strands to be formed on the other region 38' of the polymeric hydrogel 28.

In the example shown in FIG. 2B, the primers 34', 36' and 40', 42' of the primer sets 50B and 52B are attached to the polymeric hydrogel 28 through linkers 56. The polymeric hydrogel 28 has surface functional groups that can immobilize the terminal groups of the linkers 56 at the 5' end of the primers of the initial primer set 30, 30', and thus of the primers 34', 36' and 40', 42' generated using the methods disclosed herein.

Examples of suitable linkers 46 may include nucleic acid linkers (e.g., 10 nucleotides or less) or non-nucleic acid linkers, such as a polyethylene glycol chain, an alkyl group or a carbon chain, an aliphatic linker with vicinal diols, a peptide linker, etc. An example of a nucleic acid linker is a polyT spacer, although other nucleotides can also be used. In one example, the spacer is a 6T to 10T spacer. The following are some examples of nucleotides including non-nucleic acid linkers with terminal alkyne groups (where B is the nucleobase and "oligo" is the primer sequence):

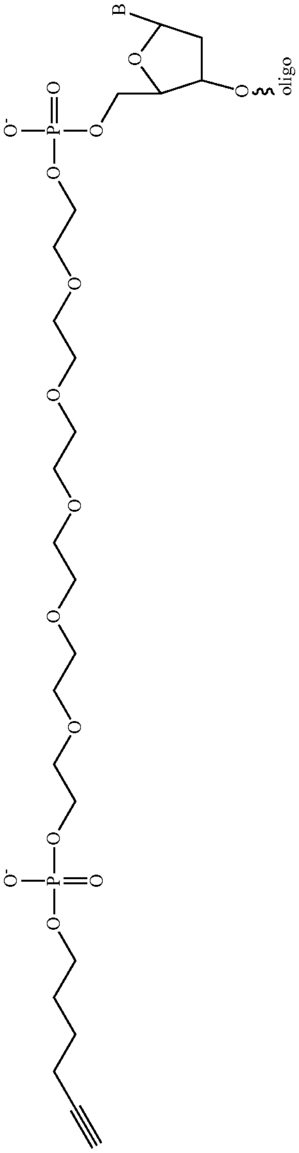
5′ Hexynyl-HEG-oligo
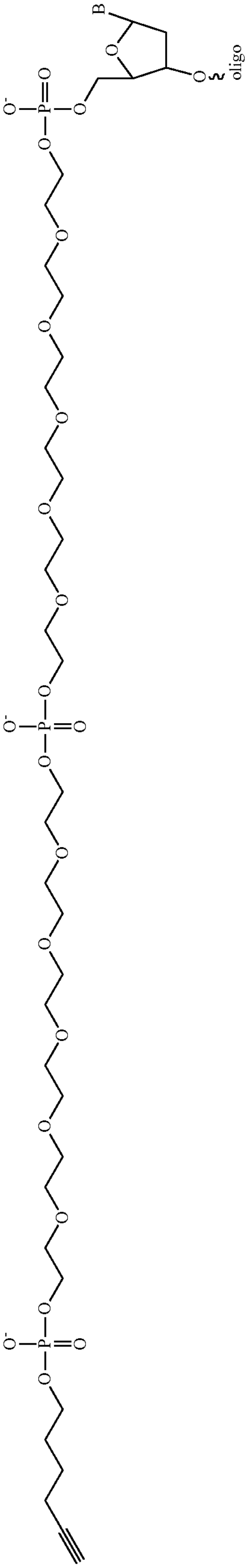
5′ Hexynyl-HEG-HEG-oligo
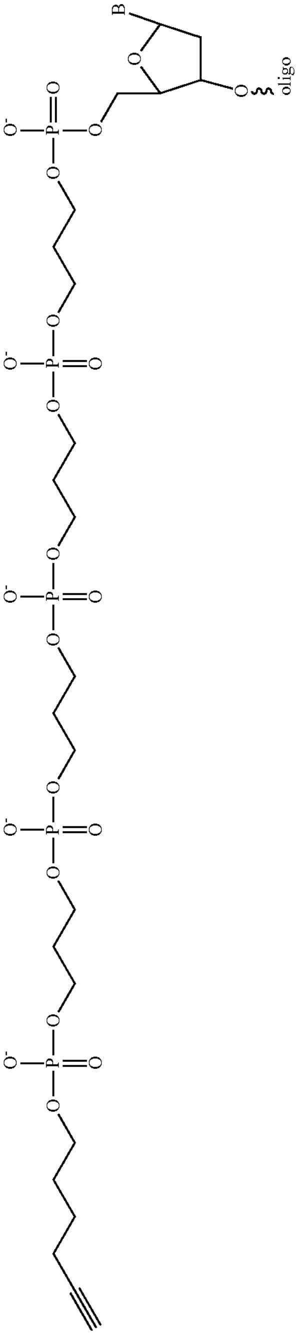
5′ Hexynyl-C3 spacer-C3 spacer-C3 spacer-C3 spacer-oligo In the example shown in FIG. 2B, the primers 34', 42' have the same sequence (e.g., P5) and the same or different linkers 56. The primer 42' is uncleavable, whereas the primer 34' includes the cleavage site 54 incorporated into the linker 56. Also in this example, the primers 36', 40' have the same sequence (e.g., P7) and the same or different linkers 56. The primer 36' is uncleavable, and the primer 40' includes the cleavage site 54 or 54' incorporated into the linker 56. The same type of cleavage site 54 or different types of cleavage sites 54, 54' may be used in the linkers 56 of the cleavable primers 34', 40'. The primer sets 50B, 52B have opposite linearization chemistries, which, after amplification, cluster generation, and linearization, allows forward template strands to be formed in one region 38 of the polymeric hydrogel 28 and reverse strands to be formed on the other region 38' of the polymeric hydrogel 28.

While the cleavage sites 54 or 54, 54' are shown as part of the linkers 56 in FIG. 2B, it is to be understood that the cleavage sites 54 or 54, 54' of the primers 34', 40' may be incorporated into the primer sequence rather than into the linkers 56.

In the examples shown in FIG. 2A and FIG. 2B, the attachment of the primers 34, 36 and 40, 42 or 34', 36' and 40', 42' to the polymeric hydrogel 28 leaves a template-specific portion of the primers 34, 36 and 40, 42 or 34', 36' and 40', 42' free to anneal to its cognate template and the 3' hydroxyl group free for primer extension.

Figures 6A, 6B, 6C, 6D, 6E:
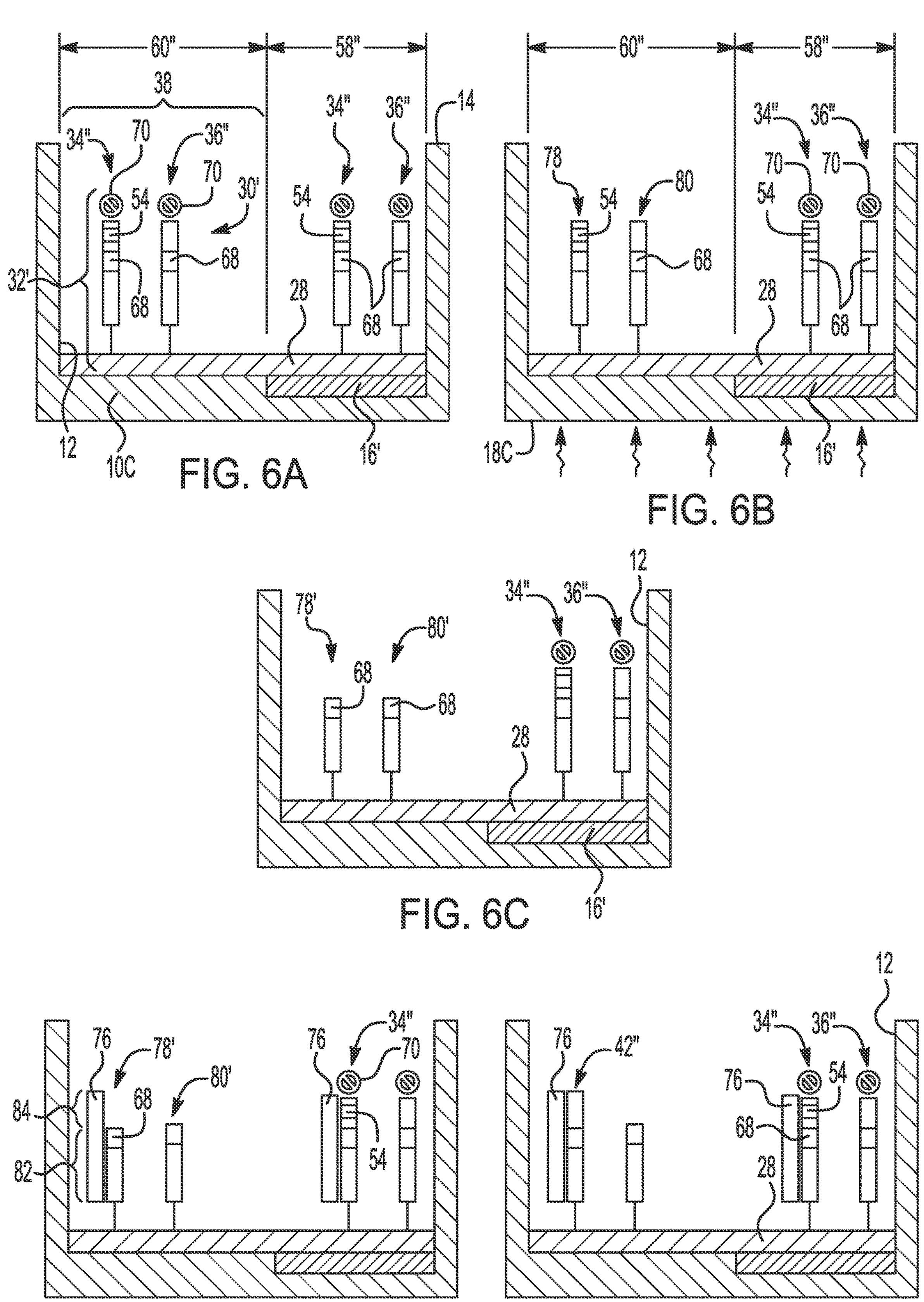
FIG. 6A through FIG. 6I are schematic views that together illustrate still another example of a method to alter at least some of the primers in a single primer set, where

While not shown in FIG. 2A or FIG. 2B, the cleavable first primer 34 and the uncleavable second primer 36 may include a nuclease resistant modification. Examples of these example primers are shown in FIG. 6A at reference numerals 34" and 36". The nuclease resistant modification (reference numeral 68 in FIG. 6A) is a bond, a nucleotide analog, or some other alteration to the nucleic acid sequence that renders the nuclease resistant primers 34" and 36" resistant to 3'→5' enzymatic activity of an exonuclease and/or an endonuclease. Examples of suitable nuclease resistant modifications 68 include a phosphorothioate bond, methyl phosphonate, a peptide nucleic acid, a morpholino, 2'-O-methyl, and a nucleotide including a phosphoramidite C3 spacer.

In some examples of the cleavable first nuclease resistant primer 34", the nuclease resistant modification 68 is positioned 5' with respect to the cleavage site 54, which is positioned 5' relative to a 3' photocleavable blocking group (reference numeral 70 in FIG. 6A). In instances where 3' photocleavable blocking group 70 does not confer nuclease resistance on its own, the cleavable first nuclease resistant primer 34" may also include a second nuclease resistant modification (not shown) that is positioned 3' with respect to the photocleavable blocking group 70. In some examples of the uncleavable second nuclease resistant primer 36", the nuclease resistant modification 68 is positioned 5' with respect to the 3' end. In instances where the 3' photocleavable blocking group 70 does not confer nuclease resistance on its own, the uncleavable second nuclease resistant primer 36" may also include a second nuclease resistant modification (not shown) that is positioned 3' with respect to the photocleavable blocking group 70. In any of these instances, the position of the nuclease resistant modification(s) 68 should leave, after nuclease digestion/cleavage, enough of the primer sequence for hybridization and extension. As noted, a single nuclease resistant modification 68 or multiple nuclease resistant modifications 68 may be incorporated into the respective primers 34", 36". As one example of the cleavable first nuclease resistant primer 34", three or more phosphorothioate bonds may be incorporated in a row beginning at a position that is 5' with respect to the position of the cleavage site 54. This number of phosphorothioate bonds may increase the nuclease resistance of the cleavable first nuclease resistant primer 34".

Each of the cleavable first nuclease resistant primer 34" and the uncleavable second nuclease resistant primer 36" includes 3' photocleavable blocking group 70. The 3' photocleavable blocking group 70 may be linked to 3' oxygen atom of the sugar molecule in the nucleotide at 3' terminal end of the primer 34", 36". Any blocking group may be used that is removable via exposure to ultraviolet light. Examples of different 3' photocleavable blocking groups include a (

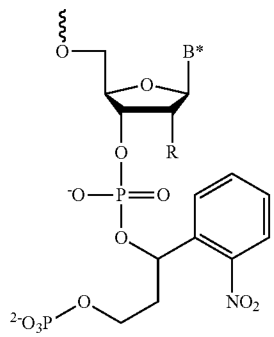

(where B is the base) and

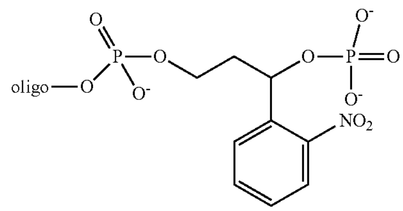

(each of which is photocleavable at wavelengths ranging from about 300 nm to about 365 nm). The 3' photocleavable blocking group 70 is removable, as described in reference to the method shown in FIG. 6A through FIG. 6I.

The methods used to generate the primer sets 50A, 52A or 50B, 52B will now be described.

FIG. 3A through FIG. 3G depicts one example of the method. This example is depicted with an example of the substrate 10B, although it is to be understood that the substrate 10A could be used.

As described in reference to FIG. 1B, the substrate 10B is an ultraviolet light transparent substrate, and the UV light blocking layer 16 is an ultraviolet light absorbing material. Prior to applying the polymeric hydrogel 28, some examples of the method shown in FIG. 3A through FIG. 3G involve selectively applying the ultraviolet light blocking layer 16 to a first region 58 the substrate 10B that corresponds with the predetermined region (of the grafted layer 32 that is to be altered), whereby a second region 60 of the substrate 10B, including a second portion of the at least some of the depressions 12, is free of the UV light blocking layer 16. Alternatively, the UV light blocking layer 16 may be generated using any of the methods described in reference to FIG. 1B. In the example shown in FIG. 1B and FIG. 3A, about one half of the depression 12 and the interstitial region 14 adjacent to that half is coated with the ultraviolet light blocking layer 16 and the other half of the depression 12 and the interstitial region 14 adjacent to that half is free of the UV light blocking layer 16.

In this example method, the polymeric hydrogel 28 is applied over the substrate 10B and the UV light blocking layer 16, and before or after the polymeric hydrogel 28 is applied, the initial primer set 30 is grafted to the polymeric hydrogel 28. Any example of the polymeric hydrogel 28 disclosed herein may be used, and the initial primer set 30 includes the cleavable first primers 34 or 34' and the uncleavable second primers 36 or 36'. Primers 34, 36 are shown in FIG. 3A through FIG. 3G.

In one example, the polymeric hydrogel 28 is applied, and then the initial primer set 30 is grafted thereto. The polymeric hydrogel 28 may be present in a mixture (e.g., with water or with ethanol and water). The mixture may then be applied to the substrate 10B and the UV light blocking layer 16 using spin coating, or dipping or dip coating, or flow of the material under positive or negative pressure, or another suitable deposition technique. These types of techniques blanketly deposit the polymeric hydrogel 28. Depending upon the chemistry of the polymeric hydrogel 28, the applied mixture may be exposed to a curing process. In an example, curing may take place at a temperature ranging from room temperature (e.g., about 25° C.) to about 95° C. for a time ranging from about 1 millisecond to about several days.

While not shown in FIG. 3A through FIG. 3G, in some examples of the method, the polymeric hydrogel 28 may be removed from the interstitial regions 14 prior to primer 34, 36 grafting.

The polishing process may be performed with a chemical slurry (including, e.g., an abrasive, a buffer, a chelating agent, a surfactant, and/or a dispersant) which can remove the polymeric hydrogel 28 from the interstitial regions 14 without deleteriously affecting the underlying substrate 10B at the regions 14. Alternatively, polishing may be performed with a solution that does not include the abrasive particles.

The chemical slurry may be used in a chemical mechanical polishing system to polish the surface of the interstitial regions 14. The polishing head(s)/pad(s) or other polishing tool(s) is/are capable of polishing the polymeric hydrogel 28 that may be present over the interstitial regions 14 while leaving the polymeric hydrogel 28 in the depression(s) 12 at least substantially intact. As an example, the polishing head may be a Strasbaugh ViPRR II polishing head.

Cleaning and drying processes may be performed after polishing. The cleaning process may utilize a water bath and sonication. The water bath may be maintained at a relatively low temperature ranging from about 22° C. to about 30° C. The drying process may involve spin drying, or drying via another suitable technique.

In this example, the primers 34, 36 of the initial primer set 30 may then be grafted to the polymeric hydrogel 28. As examples, grafting may be accomplished by flow through deposition (e.g., using a temporarily bound lid), dunk coating, spray coating, puddle dispensing, or by another suitable method. Each of these example techniques may utilize a primer solution or mixture, which may include the primer(s) 34, 36, water, a buffer, and a catalyst. With any of the grafting methods, the primers 34, 36 attach to the reactive groups of the polymeric hydrogel 28.

In another example, the primers 34, 36 are grafted to the polymeric hydrogel 28, and then the pre-grafted polymeric hydrogel is applied and cured. In these examples, additional primer grafting is not performed. In these examples of the method, the pre-grafted polymeric hydrogel 28 may be removed from the interstitial regions 14 prior to proceeding with primer alteration.

Figures 3A, 3B, 3C, 3D, 3E, 3F, 3G:
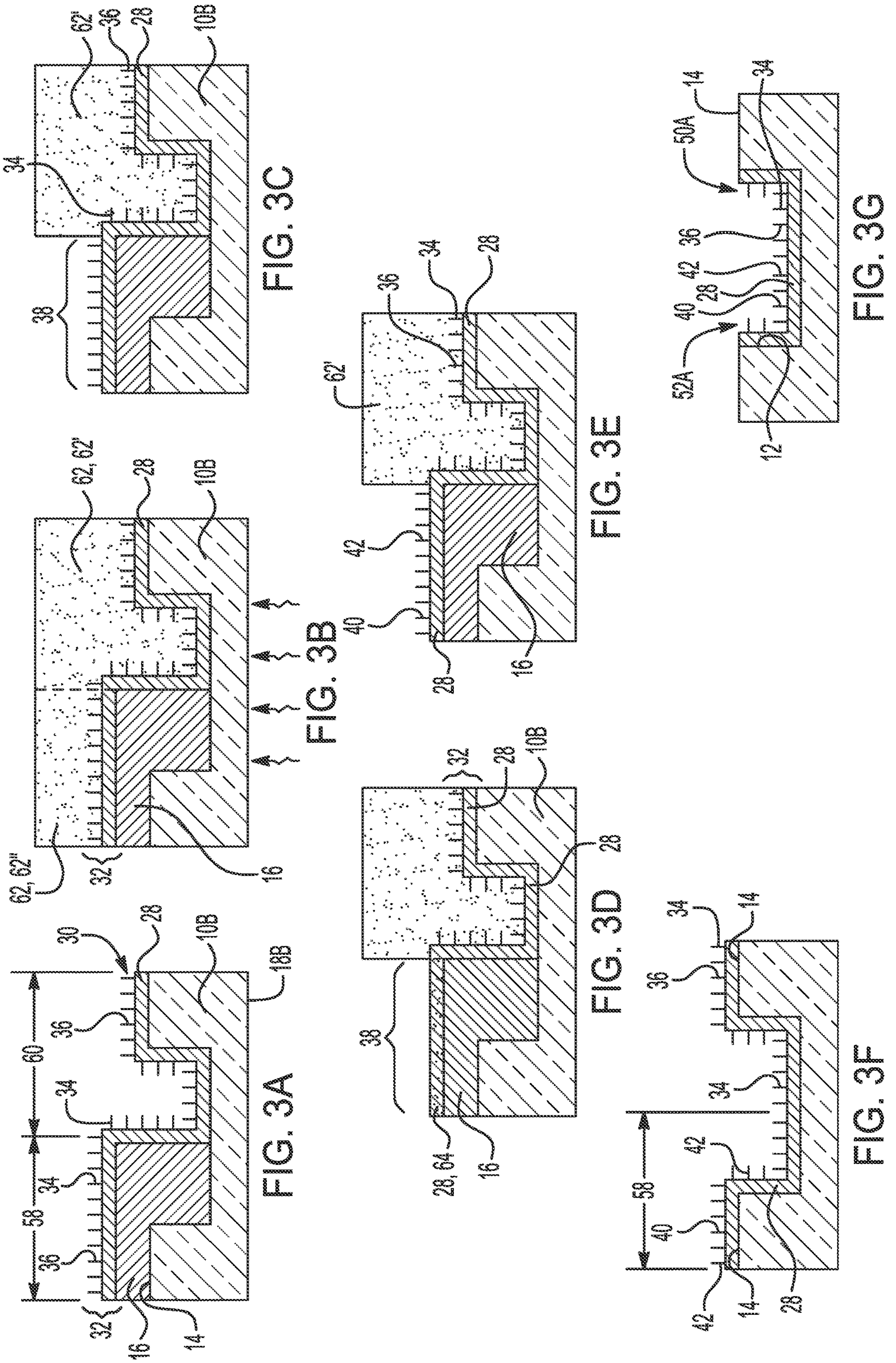
FIG. 3A through FIG. 3G are schematic views that together illustrate an example of a method to alter at least some of the primers in a single primer set, where

FIG. 3A depicts the grafted layer 32 applied over exposed surfaces of the substrate 10B and over the UV light blocking layer 16. The grafted layer 32 may be covalently bound to the substrate 10B, e.g., when the substrate 10B has been activated as described herein (e.g., using silanization or plasma ashing).

In the method of FIG. 3A through FIG. 3G, altering some of the cleavable first primers 34 and some of the uncleavable second primers 36 to introduce the cleavable second primers 40 and the uncleavable first primers 42 involves: depositing a negative photoresist 62 over the grafted layer 32 (FIG. 3B); directing ultraviolet light through the substrate 10B (from the side 18B), whereby portions of the negative photoresist 62 overlying the second region 60 become an insoluble negative photoresist 62' that overlies the grafted layer 32 at the second region 60, and portions (e.g., 62") of the negative photoresist 62 overlying the first region 58 remain soluble (FIG. 3B); removing the soluble portions 62" of the negative photoresist, thereby exposing the predetermined region 38 of the grafted layer 32 (FIG. 3C); exposing the predetermined region 38 of the grafted layer 32 to a nuclease to digest the some of the cleavable first primers 34 and the some of the uncleavable second primers 36 and generate a primer depleted portion 64 of the grafted layer 32 (FIG. 3D); and grafting the cleavable second primers 40 and the uncleavable first primers 42 to the primer depleted portion 64 (FIG. 3E).

As shown in FIG. 3B, the negative photoresist 62 is deposited over the grafted layer 32. Any of the deposition techniques set forth herein may be used. An example of a suitable negative photoresist 62 includes the NR® series photoresist (available from Futurrex). Other suitable negative photoresists 62 include the SU-8 Series and the KMPR® Series (both of which are available from Kayaku Advanced Materials, Inc.), or the UVN™ Series (available from DuPont).

The negative photoresist 62 is then exposed to an ultraviolet light dosage through the substrate 10B, where the light is introduced from the side 18B. The UV light blocking layer 16 blocks the light from reaching the negative photoresist 62 overlying the UV light blocking layer 16, and thus this portion remains soluble. Thus, the soluble negative photoresist 62" overlies the first portion 58 of the substrate 10B. The remainder of the negative photoresist 62 is exposed to the light and thus becomes insoluble. Thus, the insoluble negative photoresist 62' overlies the second portion 60 of the substrate 10B.

FIG. 3C depicts when the soluble negative photoresist 62" is removed. The soluble negative photoresist 62" may be removed using any suitable developer. Examples of suitable developers for the negative photoresist include aqueous-alkaline solutions, such as diluted sodium hydroxide, diluted potassium hydroxide, or an aqueous solution of the metal ion free organic TMAH (tetramethylammoniumhydroxide). The removal of the soluble negative photoresist 62" exposes the predetermined region 38 of the grafted layer 32 where the primers 34, 36 are to be altered.

In this example method, primer 34, 36 alteration involves removing some of the cleavable first primers 34 and the some of the uncleavable second primers 36 and replacing these primers 34, 36 with primers 40, 42 having orthogonal cleaving chemistry. In this example method, the predetermined region 38 of the grafted layer 32 is exposed to a nuclease to digest at least some of the cleavable first primers 34 and at least some of the uncleavable second primers 36 at this region 38. The nuclease is an enzyme, such as an exonuclease or an endonuclease. The nuclease enzyme has 3'-5' activity. In an example, the nuclease enzyme is selected from the group consisting of Nuclease P1, Nuclease BAL-31, DNase I, and Micrococcal Nuclease, Exonuclease I, Thermolabile Exonuclease I, Exonuclease T, Exonuclease VII, Mung Bean Nuclease, and Exonuclease V. As shown in FIG. 3C, the nuclease enzyme digests some or all of the primers 34, 36 from the predetermined region 38. This generates the primer depleted portion 64 of the grafted layer 32, as shown in FIG. 3D. It is to be understood that the primer depleted portion 64 of the grafted layer 32 is the polymeric hydrogel 28, as the primers 34, 36 have been removed. The primers 34, 36 that are covered by the insoluble negative photoresist 62' remain intact as they are not exposed to the nuclease enzyme. Heating may be used to deactivate some of the nuclease enzymes.

A washing process may be performed to remove the nuclease enzyme and any digested primers 34, 36 from the surface. The washing process may involve water with a surfactant (e.g., TWEEN® 20 (polyethylene glycol sorbitan monolaurate) from Croda).

The cleavable second primers 40 and the uncleavable first primers 42 are then grafted to the primer depleted portion 64 of the previously grafted layer 32 (i.e., the polymeric hydrogel 28 where primers 34, 36 were removed). This is shown in FIG. 3E. While the cleavable second primers 40 and the uncleavable first primers 42 are shown in FIG. 3E, it is to be understood that the cleavable second primers 40' and the uncleavable first primers 42' may be used. The primers 40, 42 may be grafted using any of the grafting techniques set forth herein. The primers 40, 42 attach to residual functional groups (e.g., azides) of the polymeric hydrogel 28 at the primer depleted portion 64 (which corresponds with the predetermined region 38).

Because the primers 40, 42 attach to the residual functional groups (e.g., azides) of the polymeric hydrogel 28 at the primer depleted portion 64, capping molecules are not introduced to any portions of the grafted layer 32. Capping molecules have previously been used to inactivate residual functional groups of a polymeric hydrogel 28 so the subsequently grafted primers do not attach to the polymeric hydrogel 28. However, these capping molecule have been found to diffuse under photoresists that may be in place to protect other regions of the polymeric hydrogel 28, and thus can inactivate residual functional groups where subsequent primer grafting may have been desirable. By not utilizing capping molecules, this example method avoids the potential challenge associated with such molecules. Additionally, the nuclease used in this example method is bulky and is less readily capable of diffusing under the insoluble negative photoresist 62'. As such, because the primers 34, 36 and residual functional groups of the polymeric hydrogel 28 overlying the region 60 of the substrate 10B are covered by the insoluble negative photoresist 62', they are substantially shielded from digestion and primer 40, 42 grafting.

In some examples, both exposing the predetermined region 38 of the grafted layer 32 to the nuclease to generate the primer depleted portion 64, and grafting the cleavable second primers 40 and the uncleavable first primers 42 to the primer depleted portion 64 are performed in a salt solution having from about 0.5 M salt to about 5 M salt. Examples of suitable aqueous salt solutions include from about 0.5 M sodium chloride to about 5 M sodium chloride, from about 0.5 M sodium sulfate to about 2 M sodium sulfate, from about 0.5 M potassium chloride to about 3 M potassium chloride, from about 0.5 M $Na_3C_6H_5O_7$ sodium citrate to about 2 M sodium citrate, from about 0.5 M sodium carbonate to about 2 M sodium carbonate, or from about 0.5 M sodium phosphate to about 2 M sodium phosphate. The salt solution helps to de-swell the polymeric hydrogel 28, and thus further reduces the likelihood of the nuclease diffusing underneath the insoluble negative photoresist 62'. When using high salt conditions, it may be desirable to use salt tolerant nucleases, such as the Salt Active Nuclease (SAN) from ArcticZymes.

Referring now to FIG. 3F and FIG. 3G, the method may further include removing the insoluble negative photoresist 62', thereby exposing the grafted layer 32 at the second region 60; and removing the cleavable first primers 34, the uncleavable second primers 36, the cleavable second primers 40, and the uncleavable first primers 42 from the interstitial regions 14.

The insoluble negative photoresist 62' may be removed via a lift-off process. The lift-off process may involve a suitable remover for the type of negative photoresist 62 used. As examples, the cured, insoluble negative photoresist 62' may be lifted off with removers such as dimethylsulfoxide (DMSO) with sonication, an acetone wash, or an NMP (N-methyl-2-pyrrolidone) based stripper wash. This removal process leaves the underlying grafted layer 32 (i.e., polymeric hydrogel 28 having primers 34, 36 grafted thereto) intact.

In some examples of the method, prior to removing the cleavable first primers 34, the uncleavable second primers 36, the cleavable second primers 40, and the uncleavable first primers 42 from the interstitial regions 14 (as described in reference to FIG. 3G), the method further comprises removing the ultraviolet light blocking layer 16, whereby at least 50% the cleavable second primers 40 and the uncleavable first primers 42 remain intact. The removal of the ultraviolet light blocking layer 16 may involve processes to remove the ultraviolet light blocking layer 16 and increase the adhesion between the remaining polymeric hydrogel 28 and the underlying substrate 10B.

The ultraviolet light blocking layer 16 may be removed by a wet etching process, which depends upon the material of the ultraviolet light blocking layer 16. In an example, the ultraviolet light blocking layer 16 (e.g., aluminum having about 30 nm thickness) can be etched by exposure to a 1-2% KOH solution or a sodium carbonate buffer (pH~10) for about 3 to 5 minutes, without mechanical stress including agitation or sonication. The etching process can be slowed by diluting the etchant and increasing the duration of the process, which may improve the retention of the polymeric hydrogel 28. The removal of the ultraviolet light blocking layer 16 does not remove the polymeric hydrogel 28 (or the primers 40, 42 attached thereto), but does expose the surface of the substrate 10B at the region 58. The underlying substrate 10B may also be inert to the wet etching process.

The removal of the ultraviolet light blocking layer 16 creates a gap between the surface of the substrate 10B and the polymeric hydrogel 28 at the region 58. A variety of methods may be performed for increasing adhesion between the polymeric hydrogel 28 and the substrate surface at the region 58.

The following are examples of methods that may be used to increase adhesion between the polymeric hydrogel 28 and the substrate surface at the region 58.

In one example, increasing the adhesion between the polymeric hydrogel 28 and the substrate surface at the region 58 involves heating the polymeric hydrogel 28 and the substrate surface at the region 58. Heating can speed up covalent bonding between the polymeric hydrogel 28 and the substrate surface at the region 58. In an example, heating may be performed at a temperature ranging from about 55°

C. to about 65° C. for a time ranging from about 25 minutes to about 35 minutes. In another example, heating may be performed at a temperature of about 60° C. for a time of about 30 minutes.

In another example, increasing the adhesion between the polymeric hydrogel 28 and the substrate surface at the region 58 involves applying a protective coating (not shown) over the polymeric hydrogel 28 (with the primers 40, 42 and 34, 36 attached); heating the polymeric hydrogel 28 and the substrate surface at the region 58; and removing the protective coating. The protective coating may be generated using an aqueous solution that includes up to about 15% (mass to volume) of a water soluble material selected from the group consisting of a polyvinyl alcohol/polyethylene glycol graft copolymer (one example of which includes KOLLICOAT® IR, available from BASF Corp.), sucrose, polyacrylamide, dextran (e.g., molecular weight of 200,000 Da), polyacrylamide (e.g., molecular weight of 40,000 Da, 200,000 Da, etc.), polyethylene glycol, ethylenediaminetetraacetic acid sodium salt (i.e., EDTA), tris(hydroxymethyl)aminomethane with ethylenediaminetetraacetic acid, (tris(2-carboxyethyl) phosphine), tris(3-hydroxypropyltriazolylmethyl) amine, bathophenanthrolinedisulfonic acid disodium salt, hydroxyl functional polymers, glycerol, or saline sodium citrate. Any suitable deposition technique may be used to apply the aqueous solution. After the aqueous solution is applied, it may be heated to evaporate the water and form the protective coating. The heating process described for increasing the adhesion between the polymeric hydrogel 28 and the substrate surface at the region 58 may be performed with the protective coating in place. The protective coating may then be removed by exposure to water at a desirable time.

In still another example, increasing the adhesion between the polymeric hydrogel 28 and the substrate surface at the region 58 involves selectively silanizing the substrate surface at the region 58. For selective silanization, a silane may be used that includes functional groups that can attach to functional groups of the polymeric hydrogel 28 and functional groups that can attach to the substrate surface. Examples of suitable silanes include an alkynyl silane, and a norbornene silane. The amino silane or the alkynyl silane can attach to an azide functional group of the polymeric hydrogel 28. The norbornene silane can respectively attach to an azide functional group or a tetrazine of the functionalized layer. The alkynyl silane may include a cycloalkyne unsaturated moiety, such as O-propargyl-N-(triethoxysilylpropyl) carbamate, cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0] non-3-yne). The norbornene silane may be a norbornene derivative, e.g., a (hetero) norbornene including an oxygen or nitrogen in place of one of the carbon atoms. An example of the norbornene silane includes [(5-bicyclo[2.2.1]hept-2-enyl)ethyl]trimethoxysilane.

The silane is introduced into an aqueous or other solvent based solution that the polymeric hydrogel 28 can take up (e.g., absorb), and the appropriate reactions take place between the silane and the respective functional groups. The aqueous or solvent based silane solution may be applied using any suitable technique, e.g., spin coating, or other deposition method disclosed herein. Alternatively, vapor deposition (e.g., a YES method) may be used for a pure silane (i.e., not in solution).

As shown in FIG. 3G, the cleavable first primers 34, the uncleavable second primers 36, the cleavable second primers 40, and the uncleavable first primers 42 may then be removed from the interstitial regions 14. The primers 34, 36, 40, 42 and the underlying polymeric hydrogel 28 may be removed from the interstitial regions 14 using a polishing process as described herein. It is to be understood that the polishing process may be performed at this point in the method if it had not been performed after polymeric hydrogel 28 application and prior to primer 34, 36 grafting, or immediately after the pre-grafted polymeric hydrogel 28 was applied.

The resulting structure is shown in FIG. 3G, which includes the polymeric hydrogel 28 with two different primers sets 50A, 52A at spatially separated regions of the depression 12.

In some examples, the ultraviolet light blocking layer 16 is also transparent to visible light that is to be used in a sequencing operation. In these examples, the ultraviolet light blocking layer 16 may not be removed as described herein in reference to FIG. 3F. In these examples, it may be desirable that the UV light blocking layer 16 be conformally coated to the region 58 of the substrate 10B so that it does not fill the portion of the depression 12 as shown in FIG. 3A, but rather aligns with the surfaces at the portion of the depression 12, as shown in FIG. 1B. Thus, when polishing is performed, the primers 40, 42 and polymeric hydrogel 28 are removed from the interstitial regions 14, but remain over the ultraviolet light blocking layer 16 in the portion of the depression 12. Alternatively, it may be desirable to use the substrate 10A when the ultraviolet light blocking layer 16 is to remain in the depression 12.

In still other examples, a modified version of the method shown in FIG. 3A through FIG. 3G may be performed with the substrate 10C shown in FIG. 1C. In this example (as described in reference to FIG. 1C), the substrate 10C is an ultraviolet light transparent substrate that includes an ultraviolet light blocking and visible light transparent layer (one example of UV light blocking layer 16') embedded in a first region 58 of the substrate 10C that corresponds with the predetermined region 38, whereby a second region 60 of the substrate 10C, including a second portion of the at least some of the depressions 12, is free of the embedded ultraviolet light blocking and visible light transparent layer 16'. The UV light blocking layer 16' may be fully embedded in the substrate material, or may have additional material layer(s) applied over the UV light blocking layer 16'.

In this example method, altering the some of the cleavable first primers 34 and the some of the uncleavable second primers 36 to introduce the cleavable second primers 40 and the uncleavable first primers 42 involves depositing a negative photoresist 62 over the grafted layer 32 (as described in reference to FIG. 3B); directing ultraviolet light through the substrate 10C (from the side 18C), whereby a portion of the negative photoresist 62 overlying the second region 60 becomes an insoluble negative photoresist 62' that overlies the grafted layer 32 at the second region 60, and another portion, e.g., 62", of the negative photoresist 62 overlying the first region 58 remains soluble (as described in reference to FIG. 3B); removing the soluble portion 62" of the negative photoresist, thereby exposing the predetermined region 38 of the grafted layer 32 (as described in reference to FIG. 3C); exposing the predetermined region 38 of the grafted layer 32 to a nuclease to digest the some of the cleavable first primers 34 and the some of the uncleavable second primers 36 and generate a primer depleted portion 64 of the grafted layer 32 (as described in reference to FIG. 3D); and grafting the cleavable second primers 40 and the uncleavable first primers 42 to the primer depleted portion 64 (as described in reference to FIG. 3E).

When the substrate 10C including a UV light blocking and visible light transparent layer 16' is used, the modified version of the method shown in FIG. 3A through FIG. 3G does not include the removal of the layer 16'. Rather, layer 16' remains in the flow cell positioned between the substrate 10C and the altered portion of the polymeric hydrogel 28 attached to the primers 40, 42.

The modified version of the method shown in FIG. 3A through FIG. 3G further includes removing the insoluble negative photoresist 62', thereby exposing the grafted layer 32 at the second region 60 (as described in reference to FIG. 3F); and removing the cleavable first primers 34, the uncleavable second primers 36, the cleavable second primers 40, and the uncleavable first primers 42 (along with the polymeric hydrogel 28) from the interstitial regions 14.

Figure 4A:
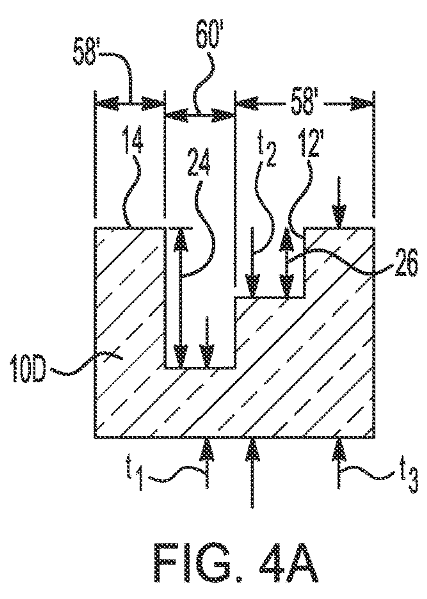
FIG. 4A through FIG. 4H are schematic views that together illustrate another example of a method to alter at least some of the primers in a single primer set, where

FIG. 4A through FIG. 4H depicts another example of the method. This example utilizes the substrate 10D. As such, as described in reference to FIG. 1D, the substrate 10D is transparent to visible light; each depression is a multi-depth depression 12' including a deep portion 24 adjacent to a shallow portion 26; the deep portion 24 of each multi-depth depression 12' overlies an ultraviolet light transparent portion 60' of the substrate 10D (having thickness $t_1$); and the interstitial regions 14 and the shallow portion 26 of each multi-depth depression 12' overlie ultraviolet light blocking portions 58' of the substrate 10D (having thicknesses $t_3$ and $t_2$). A portion of the substrate 10D including the single multi-depth depression 12' is shown in FIG. 4A.

Figure 4B:
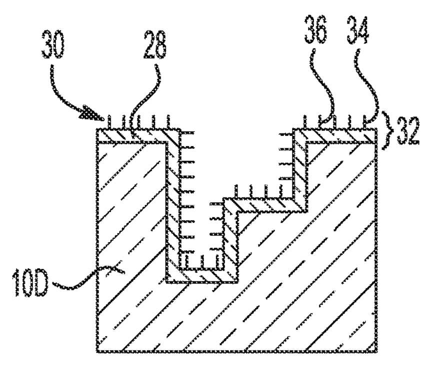

As shown in FIG. 4B, the polymeric hydrogel 28 is applied over the substrate 10D, and before or after the polymeric hydrogel 28 is applied, the initial primer set 30 is grafted to the polymeric hydrogel 28. Any example of the polymeric hydrogel 28 disclosed herein may be used, and the initial primer set 30 includes the cleavable first primers 34 or 34' and the uncleavable second primers 36 or 36'. Primers 34, 36 are shown in FIG. 4B through FIG. 4H.

In one example, the polymeric hydrogel 28 is applied, and then the initial primer set 30 is grafted thereto. These processes may be performed as described in reference to FIG. 3A. In another example, the primers 34, 36 are grafted to the polymeric hydrogel 28, and then the pre-grafted polymeric hydrogel is applied to the substrate 10D and cured.

Figure 4C:
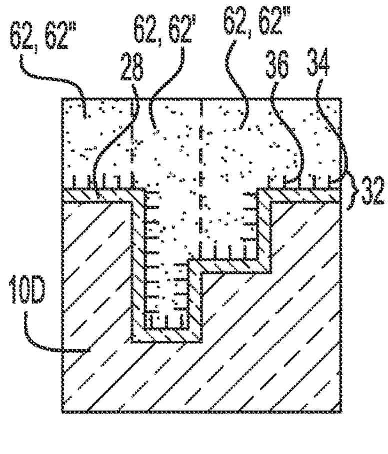
Figure 4D:
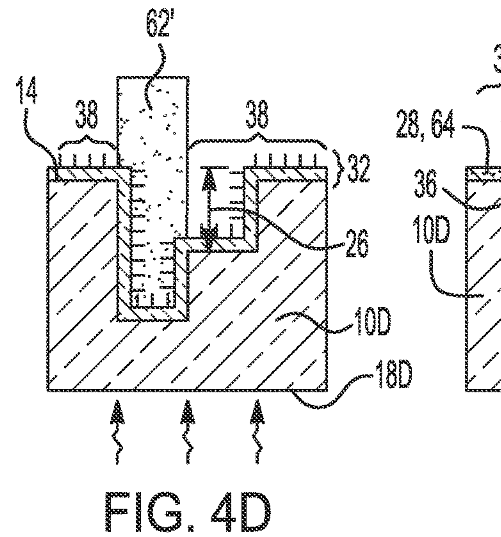
Figure 4E:
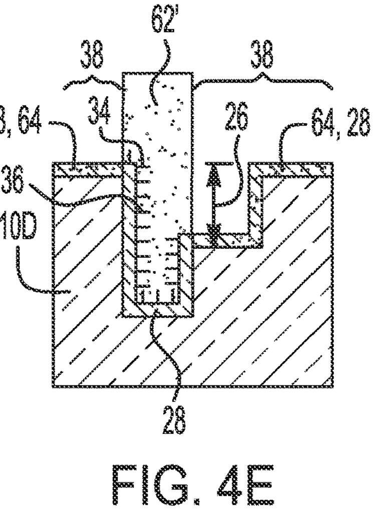
Figure 4F:
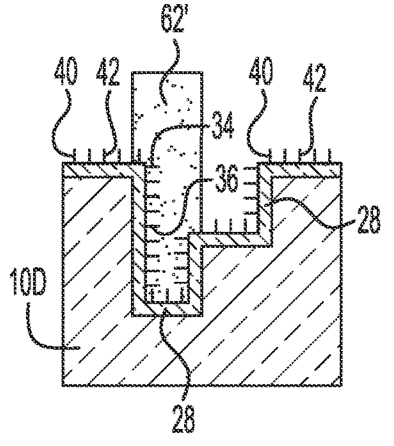
Figure 4G:
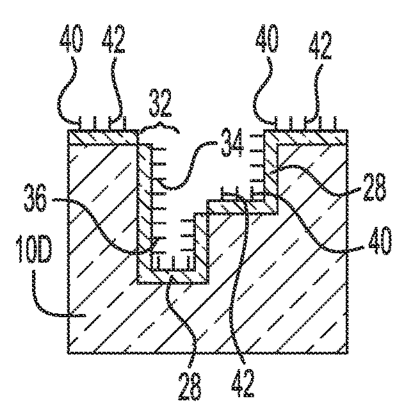

In this example method, altering some of the cleavable first primers 34 and the some of the uncleavable second primers 36 to introduce the cleavable second primers 40 and the uncleavable first primers 42 involves: depositing a negative photoresist 62 over the grafted layer 32 (FIG. 4C); directing ultraviolet light through the substrate 10D (from the side 18D), whereby portions of the negative photoresist 62 in the deep portions 24 become an insoluble negative photoresist 62' that overlies the grafted layer 32 at the deep portions 24, and portions (e.g., 62") of the negative photoresist 62 overlying the interstitial regions 14 and in the shallow portions 26 remain soluble (FIG. 4C and FIG. 4D); removing the soluble portions 62" of the negative photoresist, thereby exposing the predetermined region 38 of the grafted layer 32 (FIG. 4D); exposing the predetermined region 38 of the grafted layer 32 to a nuclease to digest the some of the cleavable first primers 34 and the some of the uncleavable second primers 36 and generate a primer depleted portion 64 of the (previously) grafted layer 32 (FIG. 4E); and grafting the cleavable second primers 40 and the uncleavable first primers 42 to the primer depleted portion 64 (FIG. 4F).

The negative photoresist 62 shown in FIG. 4C may be any of the examples set forth herein, and may be applied using any of the techniques disclosed herein. The ultraviolet light may be introduced through the side 18D and directed through the substrate 10D, as shown in FIG. 4D. The portions 58' of the substrate 10D having thicknesses $t_2$ and $t_3$ absorb the light, and thus block the light from reaching the negative photoresist 62 in the shallow portion 26 and the interstitial regions 14. Thus, the soluble negative photoresist 62" overlies the shallow portion 26 and the interstitial regions 14. The remainder of the negative photoresist 62, i.e., that overlies the portion 60' of the substrate 10D having thickness $t_1$, is exposed to the light and thus becomes insoluble. Thus, the insoluble negative photoresist 62' is present in the deep portion 24 and overlies the portion 60' of the substrate 10D.

The soluble negative photoresist 62" is then removed, as shown at FIG. 4D, using any of the developers set forth herein. The removal of the soluble negative photoresist 62" exposes the predetermined region 38 of the grafted layer 32 where the primers 34, 36 are to be altered.

In this example method, primer 34, 36 alteration involves removing some of the cleavable first primers 34 and the some of the uncleavable second primers 36 and replacing these primers 34, 36 with primers 40, 42 having orthogonal cleaving chemistry. The primer 34, 36 removal may be performed as described in reference to FIG. 3D, where the nuclease is used to digest some of the cleavable first primers 34 and some of the uncleavable second primers 36. This generates the primer depleted portion 64 of the grafted layer 32. It is to be understood that the primer depleted portion 64 of the grafted layer 32 is the polymeric hydrogel 28, as the primers 34, 36 have been removed. In this example, the primer depleted portion 64 is in the shallow portion 26 and over the interstitial regions 14, as shown in FIG. 4E. Also in this example, the primers 34, 36 that are covered by the insoluble negative photoresist 62' remain intact as they are not exposed to the nuclease enzyme.

The cleavable second primers 40 and the uncleavable first primers 42 are then grafted to the primer depleted portion 64, as shown in FIG. 4F. Primer 40, 42 grafting may be performed as defined in reference to FIG. 3E.

In this example method, both exposing the predetermined region 38 of the grafted layer 32 to the nuclease to generate the primer depleted portion 64, and grafting the cleavable second primers 40 and the uncleavable first primers 42 to the primer depleted portion 64 may be performed in any of the salt solutions described herein having from about 0.5 M salt to about 5 M salt. It may be desirable to use a salt tolerant nuclease with the high salt conditions.

Figure 4H:
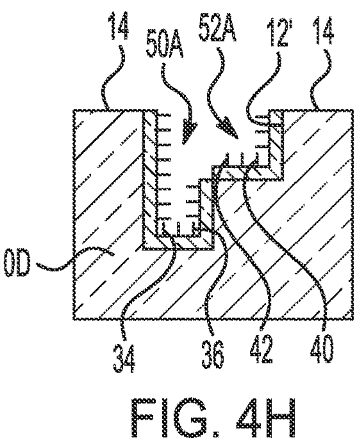

The method shown in FIG. 4A through FIG. 4H also includes removing the insoluble negative photoresist 62', thereby exposing the grafted layer 32 at the deep portions 24 (FIG. 4G); and removing the cleavable second primers 40 and the uncleavable first primers 42 from the interstitial regions 14 (FIG. 4H). The insoluble negative photoresist 62' may be removed via a lift-off process using any suitable remover, e.g., as described in reference to FIG. 3F. The primers 40, 42 and the underling polymeric hydrogel 28 may be removed from the interstitial regions 14 using a polishing process, e.g., as described in reference to FIG. 3G.

The resulting structure is shown in FIG. 4H, which includes the polymeric hydrogel 28 with two different primers sets 50A, 52A at spatially separated regions within the multi-depth depression 12'.

FIG. 5A through FIG. 5H depicts yet another example of the method. This example utilizes the substrate 10D and is similar to the method described in FIG. 4A through FIG. 4H, except that a positive photoresist 66 is used instead of the negative photoresist 62.

Figures 5A, 5B, 5C, 5D, 5E, 5F, 5G, 5H:
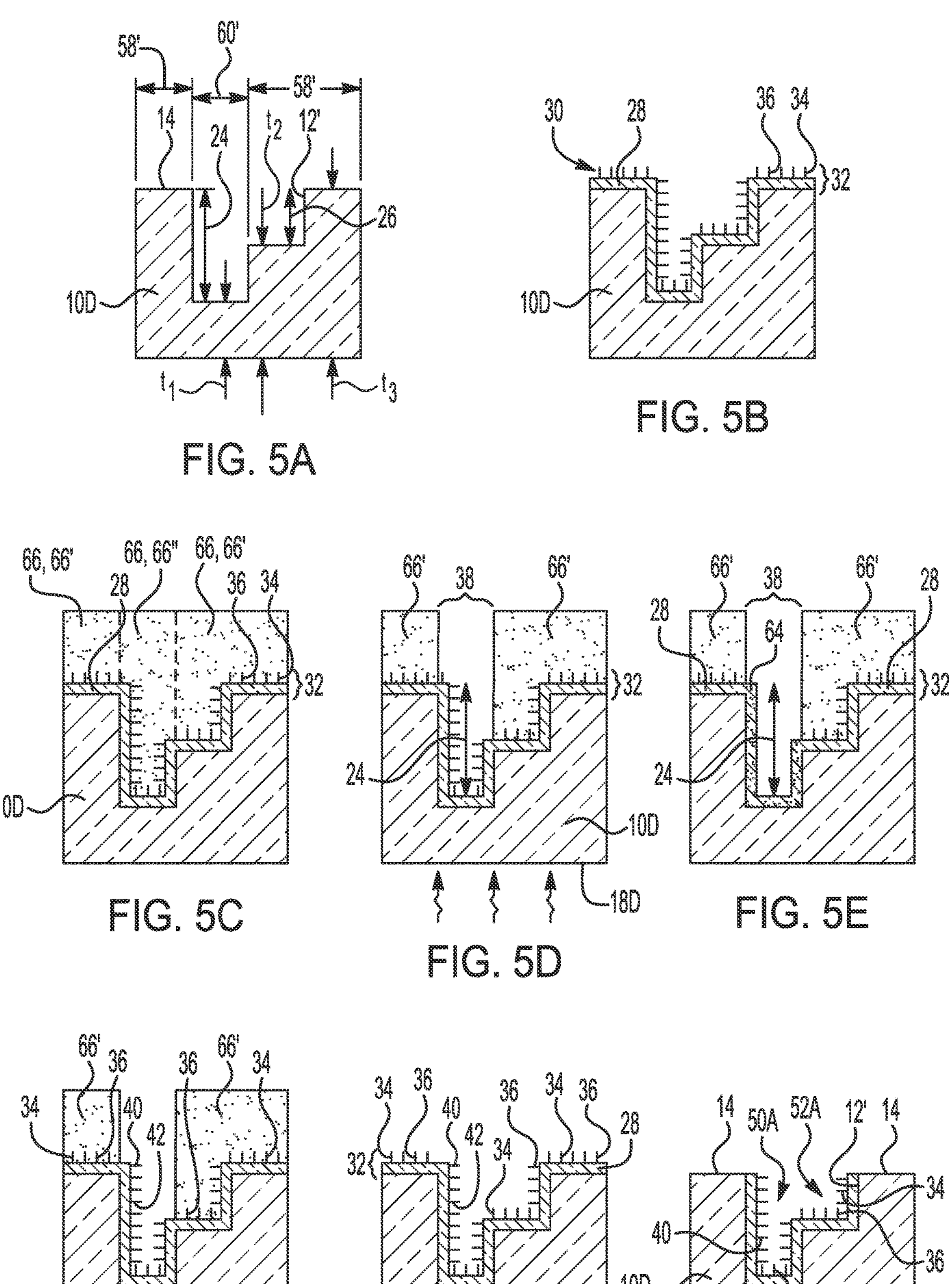
FIG. 5A through FIG. 5H are schematic views that together illustrate yet another example of a method to alter at least some of the primers in a single primer set, where

The substrate 10D shown in FIG. 5A is the same as that shown and described in FIG. 4A.

As shown in FIG. 5B, the polymeric hydrogel 28 is applied over the substrate 10D, and before or after the polymeric hydrogel 28 is applied, the initial primer set 30 is grafted to the polymeric hydrogel 28. Any example of the polymeric hydrogel 28 disclosed herein may be used, and the initial primer set 30 includes the cleavable first primers 34 or 34' and the uncleavable second primers 36 or 36'. Primers 34, 36 are shown in FIG. 5B through FIG. 5H.

In one example, the polymeric hydrogel 28 is applied, and then the initial primer set 30 is grafted thereto. These processes may be performed as described in reference to FIG. 3A. In another example, the primers 34, 36 are grafted to the polymeric hydrogel 28, and then the pre-grafted polymeric hydrogel is applied to the substrate 10D and cured.

In this example method, altering some of the cleavable first primers 34 and the some of the uncleavable second primers 36 to introduce the cleavable second primers 40 and the uncleavable first primers 42 involves: depositing the positive photoresist 66 over the grafted layer 32 (FIG. 5C); directing ultraviolet light through the substrate 10D (from the side 18D), whereby portions of the positive photoresist 66 overlying the interstitial regions 14 and in the shallow portions 26 become an insoluble positive photoresist 66' that overlies the grafted layer 32 at the interstitial regions 14 and the shallow portions 26, and portions (e.g., 66") of the positive photoresist 66 in the deep portions 24 become soluble (FIG. 5C and FIG. 5D); removing the soluble portions 66" of the positive photoresist, thereby exposing the predetermined region 38 of the grafted layer 32 (FIG. 5D); exposing the predetermined region 38 of the grafted layer 32 to a nuclease to digest the some of the cleavable first primers 34 and the some of the uncleavable second primers 36 and generate a primer depleted portion 64 of the grafted layer 32 (FIG. 5E); and grafting the cleavable second primers 40 and the uncleavable first primers 42 to the primer depleted portion 64 (FIG. 5F).

The applied positive photoresist 66 is shown in FIG. 5C. Examples of suitable positive photoresists include the MICROPOSIT® S1800 series or the AZ® 1500 series, both of which are available from Kayaku Advanced Materials, Inc. Another example of a suitable positive photoresist is SPR™-220 (from DuPont). The positive photoresist 66 may be applied using any of the techniques disclosed herein.

As shown in FIG. 5D, the ultraviolet light may be introduced through the side 18D and directed through the substrate 10D. The portions 58' of the substrate 10D having thicknesses $t_2$ and $t_3$ absorb the light, and thus block the light from reaching the positive photoresist 66 in the shallow portion 26 and overlying the interstitial regions 14. These portions become insoluble, and thus the insoluble positive photoresist 66' overlies the shallow portion 26 and the interstitial regions 14. The remainder of the positive photoresist 66, i.e., which overlies the portion 60' of the substrate 10D having thicknesses $t_1$, is exposed to the light and thus becomes soluble. Thus, the soluble positive photoresist 66" is present in the deep portion 24 and overlies the portion 60' of the substrate 10D.

The soluble positive photoresist 66" is then removed, as shown at FIG. 5D, using a suitable developer for the positive photoresist 66 being used. Examples of suitable developers for the positive photoresist 66 include aqueous-alkaline solutions, such as diluted sodium hydroxide, diluted potassium hydroxide, or an aqueous solution of the metal ion free organic TMAH (tetramethylammoniumhydroxide). The removal of the soluble positive photoresist 66" exposes the predetermined region 38 of the grafted layer 32 where the primers 34, 36 are to be altered.

In this example method, primer 34, 36 alteration involves removing some of the cleavable first primers 34 and the some of the uncleavable second primers 36 and replacing these primers 34, 36 with primers 40, 42 having orthogonal cleaving chemistry. The primer 34, 36 removal may be performed as described in reference to FIG. 3D, where the nuclease is used to digest some of the cleavable first primers 34 and some of the uncleavable second primers 36. This generates the primer depleted portion 64 of the grafted layer 32. It is to be understood that the primer depleted portion 64 of the grafted layer 32 is the polymeric hydrogel 28, as the primers 34, 36 have been removed. In this example, the primer depleted portion 64 is in the deep portion 24, as shown in FIG. 5E. Also in this example, the primers 34, 36 that are covered by the insoluble positive photoresist 66' remain intact as they are not exposed to the nuclease enzyme.

The cleavable second primers 40 and the uncleavable first primers 42 are then grafted to the primer depleted portion 64, as shown in FIG. 5F. Primer 40, 42 grafting may be performed as defined in reference to FIG. 3E.

In this example method, both exposing the predetermined region 38 of the grafted layer 32 to the nuclease to generate the primer depleted portion 64, and grafting the cleavable second primers 40 and the uncleavable first primers 42 to the primer depleted portion 64 may be performed in any of the salt solutions described herein having from about 0.5 M salt to about 5 M salt.

The method shown in FIG. 5A through FIG. 5H also includes removing the insoluble positive photoresist 66', thereby exposing the grafted layer 32 at the interstitial regions 14 and the shallow portions 26 (FIG. 5G); and removing the cleavable first primers 34 and the uncleavable second primers 36 from the interstitial regions 14 (FIG. 5H). The insoluble positive photoresist 66' may be removed via a lift-off process using any suitable remover for the insoluble positive photoresist 66'. Examples of suitable removers include dimethylsulfoxide (DMSO) with sonication, an acetone wash, a propylene glycol monomethyl ether acetate wash, or an NMP (N-methyl-2-pyrrolidone) based stripper wash. The primers 34, 36 and the underling polymeric hydrogel 28 may be removed from the interstitial regions 14 using a polishing process, e.g., as described in reference to FIG. 3G.

The resulting structure is shown in FIG. 5H, which includes the polymeric hydrogel 28 with two different primers sets 50A, 52A at spatially separated regions within the multi-depth depression 12'.

The patterned structures (e.g., a portion of which is shown in FIG. 3G, FIG. 4H and FIG. 5H) resulting from the methods shown in the FIG. 3 series through the FIG. 5 series can be bonded to another patterned structure or to a lid to form an example of the flow cell. The substrate 10A, 10B, 10C, 10D may have a bonding region at its perimeter and/or between lanes (each of which includes a plurality of the depressions 12, 12') that can be used to attach two patterned structures or a patterned structure and a lid. Details of the bonding process and the flow cell are described in further detail below in the section entitled "Flow Cell."

The methods shown in the FIG. 6 series and the FIG. 7 series use different initial primer sets 30' and 30" than the methods shown in the FIG. 3 series through the FIG. 5 series. The methods shown in the FIG. 6 series and the FIG. 7 series can be performed after two patterned structures (e.g., the substrate with the polymeric hydrogel 28 and primer set 30' or 30" in each depression 12) have been bonded together or after one patterned structure has been bonded to a lid. As such, flow through methods may be used to perform the primer alterations shown in the FIG. 6 series and the FIG. 7 series. This is due, in part, to the fact that materials do not need to be removed from the interstitial regions 14 after primer alteration and because photoresists are not used in these methods. An example of a flow cell 72 with two bonded patterned structures 74, 74' and prior to alteration of the initial primer set 30', 30" is generally shown in FIG. 8. FIG. 8 will be referenced throughout the description of the FIG. 6 series and the FIG. 7 series; however, as noted above, the details of the bonding process and the flow cell 72 are described in further detail below in the section entitled "Flow Cell."

The method shown in FIG. 6A through FIG. 6I utilizes the primer set 30'. As described herein, each of the cleavable first primers 34" in the primer set 30' includes 3' photocleavable blocking group 70 and a nuclease resistant modification 68 positioned 5' of and a predetermined distance from a cleavage site 54, and each of the uncleavable second primers 36" includes 3' photocleavable blocking group 70 and the nuclease resistant modification 68 without the cleavage site 54. These primers 34", 36" are shown in FIG. 6A. In FIG. 6A, each depression 12 includes an ultraviolet light blocking layer 16' (or 16 if the substrate 10A or 10B is used) positioned at a first region 58", and a second region 60" of each depression 12 is transparent to ultraviolet light, wherein the second region 60" corresponds with the predetermined region 38 (where at least some primer alteration is to take place).

While not shown in FIG. 6A through FIG. 6I, this example of the method involves generating the patterned structure(s) 74, 74' (FIG. 8), bonding the patterned structures 74, 74' together or bonding one patterned structure 74 and a lid (not shown) together, and then performing the primer 34", 36" alteration in the flow cell 72.

To generate each patterned structure 74, 74', the depressions 12 are defined in the substrate 10A, 10B, or 10C and the UV light blocking layer 16 or 16' is incorporated (e.g., applied, embedded, etc.) into the first region 58, 58" of the substrate 10A, 10B, 10C as described in reference to FIG. 1A, FIG. 1B, or FIG. 1C. Then, the grafted layer 32' is applied. In this example method, applying the grafted layer 32' involves introducing the grafted layer 32' to the depressions 12 and the interstitial regions 14; and removing the grafted layer 32' from the interstitial regions 14. Any example of the polymeric hydrogel 28 disclosed herein is applied over the substrate 10A, 10B, or 10C using any suitable deposition technique, and before or after the polymeric hydrogel 28 is applied, the initial primer set 30' is grafted to the polymeric hydrogel 28 using any suitable grafting technique. The grafted layer 32' may then be removed from the interstitial regions 14 using the polishing process disclosed herein. The resulting patterned structure 74, 74' includes the grafted layer 32' within each depression 12, and the interstitial regions 14, which are free of the grafted layer 32'. One depression 12 of the patterned structure 74 is shown in FIG. 6A.

In the example shown in FIG. 6A through FIG. 6I, altering some of the cleavable first primers 34" and the some of the uncleavable second primers 36" to introduce the cleavable second primers 40" and the uncleavable first primers 42" involves sequentially altering some of the cleavable first primers 34" to introduce the uncleavable first primers 42" and altering some of the uncleavable second primers 36" to introduce the cleavable second primers 40".

Figures 6F, 6G, 6H, 6I:
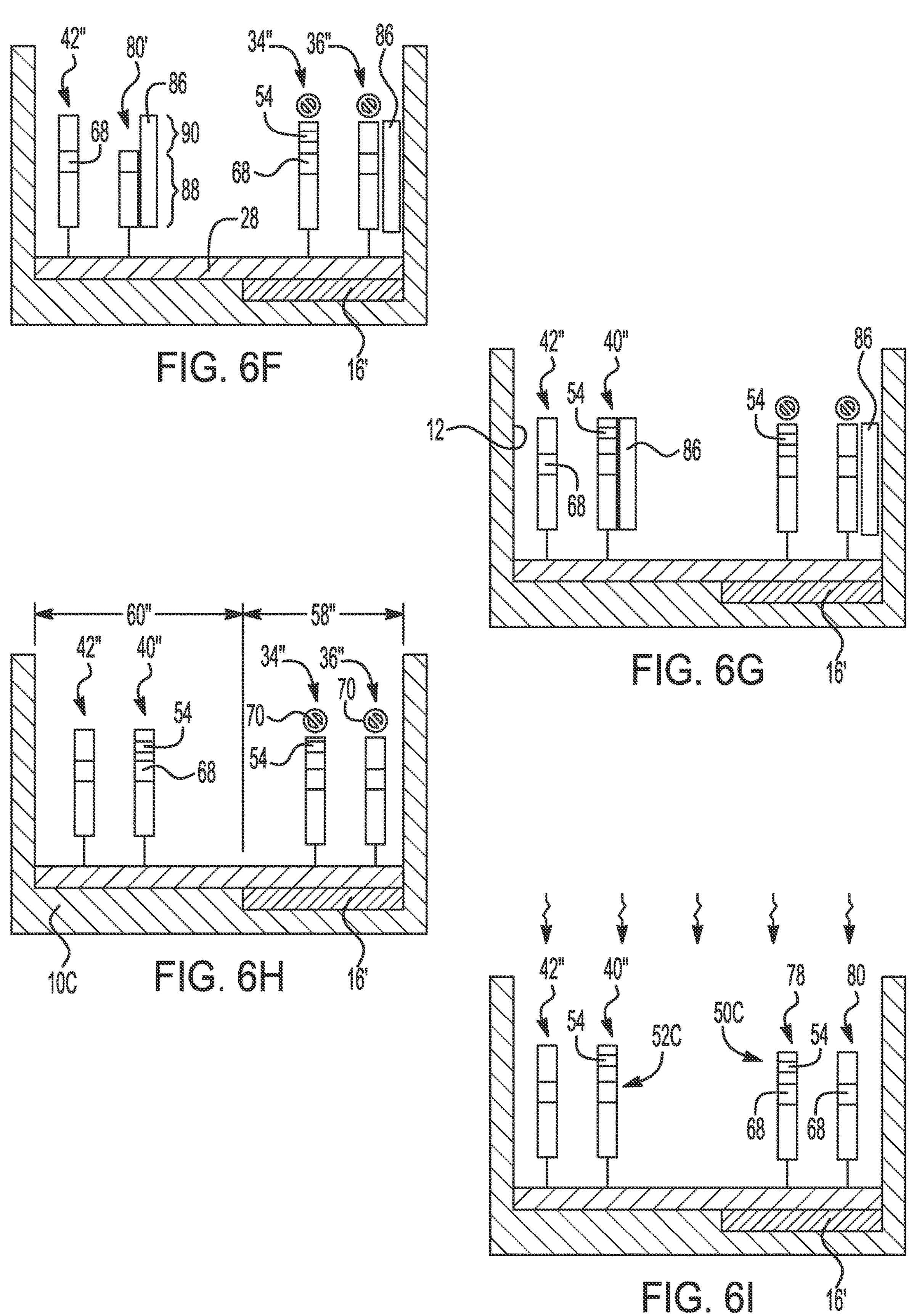
Figure 7G:
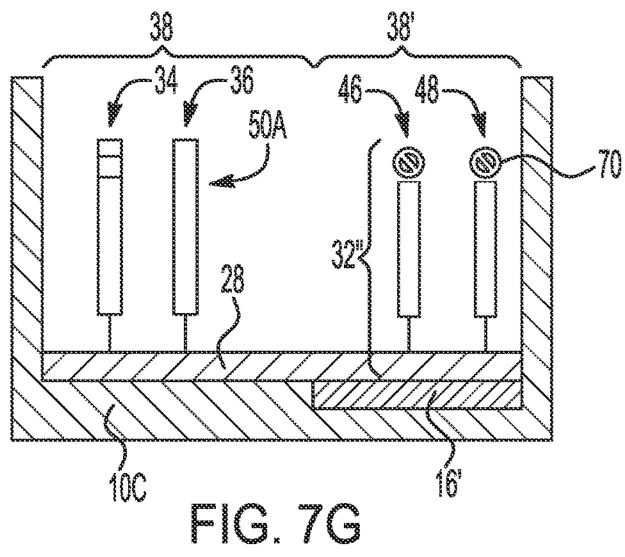

The alteration of the cleavable first nuclease resistant primers 34" is shown in FIG. 6B through FIG. 6E and the alteration of uncleavable second nuclease resistant primers 36" is shown in FIG. 6F through FIG. 6H.

The alteration of some of the cleavable first nuclease resistant primers 34" (FIG. 6B) to introduce the uncleavable first primers 42" (FIG. 6E) involves: directing ultraviolet light through the substrate 10C (from the side 18C), thereby removing 3' photocleavable blocking groups 70 from the cleavable first primers 34" and the uncleavable second primers 36" that overlie the second region 60", whereby the cleavable first primers 34" and the uncleavable second primers 36" that overlie the first region 58" remain blocked (FIG. 6B); exposing the grafted layer 32' to an exonuclease enzyme, thereby digesting portions of the cleavable first primers 34" and of the uncleavable second primers 36" that overlie the second region 60", wherein the digested portions include from respective 3' ends to the nuclease resistant modifications 68 (FIG. 6C); respectively hybridizing first primer regeneration templates 76 to remaining portions 78' of the cleavable first nuclease resistant primers 34" that overlie the second region 60" and to the cleavable first nuclease resistant primers 34" that overlie the first region 58" (FIG. 6D); using a nucleotide mixture including a thymine base, initiating polymerase extension along the first primer regeneration templates 76 at the remaining portions 78' of the cleavable first nuclease resistant primers 34" to generate the uncleavable first nuclease resistant primers 42" (FIG. 6E); and dehybridizing the first primer regeneration templates 76.

FIG. 6B depicts the introduction of ultraviolet light through the side 18C of the substrate 10C. The wavelength (s) of the UV light are sufficient to remove 3' photocleavable blocking groups 70 from the cleavable first primers 34" and the uncleavable second primers 36" that are exposed to the light. In this example, the UV light is transmitted through the substrate 10C at the second region 60". Thus, the cleavable first primers 34" and the uncleavable second primers 36" at the second region 60" are exposed to the UV light, which triggers the removal of 3' photocleavable blocking groups 70. The unblocked primers are shown at reference numerals 78 and 80, respectively. In contrast, the UV light blocking layer 16' blocks the light from reaching the cleavable first primers 34" and the uncleavable second primers 36" at the first region 58", and thus these primers 34", 36" remain 3' blocked. It is to be understood that the UV light may also transmit through the substrate 10C at the interstitial regions 14, as no UV light blocking layer 16' is present.

After the primers 34", 36" in the second region 60" are 3' unblocked, the grafted layer 32' is exposed to an exonuclease enzyme. As noted, in this example, the nuclease enzyme is as exonuclease; examples of which include Exonuclease I, Thermolabile Exonuclease I, Exonuclease T, Exonuclease VII, Mung Bean Nuclease, and Exonuclease V. As the nuclease enzyme has 3'-5' activity, it is capable of digesting a portion of the unblocked cleavable first nuclease resistant primers 78 and a portion of the unblocked uncleavable second nuclease resistant primers 80 that overlie the second region 60". The portions that are digested extend from the respective 3' ends of the unblocked primers 78, 80 to the nuclease resistant modifications 68. The nuclease resistant modifications 68 are not susceptible to nuclease digestion/cleavage. As such, those portions of the unblocked cleavable first primers 78 and of the unblocked uncleavable second primers 80 that are positioned 5' relative to the nuclease resistant modifications 68 are protected against nuclease digestion/cleavage. The portions of the primers remaining after digestion are shown at reference numerals 78' and 80' in FIG. 6C. The 3' photocleavable blocking group 70 of the primers 34", 36" that overlie the first region 58" blocks 3'→5' activity of the exonuclease enzyme, and thus these primers 34", 36" remain intact, as shown in FIG. 6C.

A wash solution may be introduced into the flow cell 72 to remove the exonuclease enzyme and the digested portions.

First primer regeneration templates 76 are then introduced into the flow cell 72. Each first primer regeneration template 76 is a complement of the sequence of the cleavable first nuclease resistant primer 34". Thus, each first primer regeneration template 76 includes a first portion 82 that is complementary to the remaining primer 78' and a second portion 84 that is complementary to the portion that was digested. The first primer regeneration templates 76 are introduced at conditions that enable the first primer regeneration template 76 to hybridize to the remaining primer 78' and the cleavable first nuclease resistant primers 34" that remain intact at the first region 58". The hybridized primer regeneration templates 76 are shown in FIG. 6D.

A nucleotide mixture containing non-cleavable nucleotides and a polymerase are then introduced into the flow cell 72. The non-cleavable nucleotides include the following bases: adenine, cytosine, guanine and thymine. Any polymerase that can accept the non-cleavable nucleotide, and that can successfully incorporate the base of the non-cleavable nucleotide at 3' end of the primers 78' may be used. Example polymerases include those polymerases from family A, such as Bsu Polymerase, Bst Polymerase, Taq Polymerase, T7 Polymerase, and many others; polymerases from families B and B2, such as Phi29 polymerase and other highly processive polymerases (family B2), Pfu Polymerase (family B), KOD Polymerase (family B), 9oN (family B), and many others; polymerases from family C, such as *Escherichia coli* DNA Pol III, and many others, polymerases from family D, such as *Pyrococcus furiosus* DNA Pol II, and many others; polymerases from family X, such as DNA Pol μ, DNA Pol β, DNA Pol σ, and many others. The nucleotide mixture may also include a liquid carrier, such as water and/or an ionic salt buffer fluid, e.g., saline citrate at millimolar to molar concentrations, sodium chloride, potassium chloride, phosphate buffered saline, etc., and other buffers, such as tris(hydroxymethyl)aminomethane (TRIS) or (4-(2-hydroxyethyl)-1-piperazineethanesulfonic acid) (HEPES). The liquid carrier may also include catalytic metal(s) intended for the extension reaction, such as $Mg^{2+}$, $Mn^{2+}$, etc. A single catalytic metal or a combination of catalytic metals may be used, and the total amount may range from about 0.01 mM to about 100 mM.

The temperature of the flow cell 72 may be adjusted to initiate a template extension reaction. The polymerase enables the extension of 3' end of the primer 78' using the second portion 84 of the first primer regeneration template 76 as a template. Because i) the extension reaction is guided by the second portion 84 of the first primer regeneration template 76, ii) the second portion 84 is complementary to the portion of the unblocked cleavable first nuclease resistant primer 78 that was digested, and iii) non-cleavable nucleotides are used, the polymerase extension along the second portion 84 generates the first nuclease resistant primer without the cleavage site 54. As such, the polymerase extension generates the uncleavable first nuclease resistant primer 42", which includes the nuclease resistant modification 68 but does not include the cleavage site 54.

While some of the first primer regeneration template 76 may hybridize to the intact cleavable first nuclease resistant primers 34" at the first region 58", polymerase extension does not occur at these primers 34".

Once the uncleavable first nuclease resistant primers 42" are generated (FIG. 6E), the first primer regeneration templates 76 are dehybridized (i.e., denatured) and are removed from the flow cell 72 (e.g., using a wash solution).

The uncleavable second nuclease resistant primers 36" at the second region 60" are then altered to introduce the cleavable second nuclease resistant primers 42". More specifically, the primers 80' that remain after unblocking and digestion of the uncleavable second nuclease resistant primers 36" in the second region 60" are then altered to introduce the cleavable second nuclease resistant primers 42". This alteration involves: respectively hybridizing second primer regeneration templates 86 to remaining portions of the uncleavable second nuclease resistant primers (i.e., primers 80') that overlie the second region 60" and to the uncleavable second nuclease resistant primers 36" that overlie the first region 58" (FIG. 6F); using a nucleotide mixture including a cleavable base, initiating polymerase extension along the second primer regeneration templates 86 at the remaining portions of the uncleavable second nuclease resistant primers (i.e., primers 80') to generate the cleavable second nuclease resistant primers 40" (FIG. 6G); and dehybridizing the second primer regeneration templates 86 (FIG. 6H).

Each second primer regeneration template 86 is a complement of the sequence of the uncleavable second nuclease resistant primer 36". Thus, each second primer regeneration template 86 includes a first portion 88 that is complementary to the remaining primer 80' and a second portion 90 that is complementary to the portion that was digested. The second primer regeneration templates 86 are introduced at conditions that enable the second primer regeneration template 86 to hybridize to the remaining primers 80' at the second region 60" and to the uncleavable second nuclease resistant primers 36" that remain intact at the first region 58". The hybridized primer regeneration templates 86 are shown in FIG. 6F.

Another nucleotide mixture, containing a cleavable nucleotide, other non-cleavable nucleotides, and a polymerase, is then introduced into the flow cell 72. The cleavable nucleotide includes a uracil base or 8-oxoguanine or any other cleavable nucleotide that can be incorporated by a polymerase. Other non-cleavable nucleotides in this mixture include the following bases: adenine, cytosine, and guanine. Any polymerase that can accept these nucleotides, and that can successfully incorporate the base of these nucleotides at the 3' end of the primers 80' may be used. This example of the nucleotide mixture may also include any example of the liquid carrier set forth herein.

The temperature of the flow cell 72 may be adjusted to initiate a template extension reaction. The polymerase enables the extension of 3' end of the remaining primer 80' using the second portion 90 of the second primer regeneration template 86 as a template. Because i) the extension reaction is guided by the second portion 90 of the second primer regeneration template 86, ii) the second portion 90 is complementary to the portion of the unblocked cleavable second nuclease resistant primer 80 that was digested, and iii) a cleavable nucleotide is used, the polymerase extension along the second portion 90 generates the second nuclease resistant primer with the cleavage site 54. As such, this polymerase extension generates the cleavable second nuclease resistant primer 40", which includes the cleavage site 54 and the nuclease resistant modification 68. The cleavable second nuclease resistant primer 40" is shown in FIG. 6G.

While some of the second primer regeneration templates 86 may hybridize to the intact second uncleavable nuclease resistant primers 36" at the first region 58", polymerase extension does not occur at these primers 36".

Once the cleavable second nuclease resistant primers 40" are generated (FIG. 6G), the second primer regeneration templates 86 are dehybridized (i.e., denatured) and are removed from the flow cell 72, as shown in FIG. 6H.

After the primer alterations described in reference to FIG. 6A through FIG. 6G are performed, the first region 58" includes the cleavable first nuclease resistant primers 34" and the uncleavable second nuclease resistant primers 36", and the second region 60" includes the uncleavable first nuclease resistant primers 42" and the cleavable second nuclease resistant primers 40".

As shown in FIG. 6H, the cleavable first nuclease resistant primers 34" and the uncleavable second nuclease resistant primers 36" still include 3' photocleavable blocking groups 70. These groups 70 may be removed by exposure to ultraviolet light (see FIG. 6I). As such, some examples of the method involve directing ultraviolet light at the surface of the substrate 10C (part of the patterned structure 74 or 74'), thereby removing 3' photocleavable blocking groups 70 from the cleavable first primers 34" and the uncleavable second primers 36" that overlie the first region 58". UV light exposure removes the remaining 3' photocleavable blocking groups 70, as depicted in FIG. 6I.

When the flow cell 72 includes a UV transparent lid, the UV light may be directed through the lid toward the cleavable first nuclease resistant primers 34" and the uncleavable second nuclease resistant primers 36" at the surface of the substrate 10C.

Alternatively, the flow cell 72 may include two patterned structures 74, 74' (as shown in FIG. 8). In one example, the final unblocking process may be performed by directing the ultraviolet light through both of the sides 18C, 18$C_2$, because the UV light that transmits through the substrate 10C at region 60" could reach the primer set 30'$_2$ of the opposed patterned structure 74', and the UV light that transmits through the second substrate 10$C_2$ at region 60"$_2$ could reach the primer set 30' of the opposed patterned structure 74. In another example, the UV light absorbing layers 16', 16'$_2$ (or layer 16 if the substrates 10A or 10B are used) may be removed before directing the ultraviolet light through one side 18C or 18$C_2$. The UV light blocking layers 16', 16'$_2$ may be removed as described in reference to the FIG. 3 series, where the wet etching is performed in a flow through manner and is followed one of the adhesion promoting processes described herein. The etchant may be introduced via an input port 94 (FIG. 8), and then the removed UV light blocking layers 16', 16'$_2$ may be removed from the flow cell 72 via an output port 96 (FIG. 8). After the UV light blocking layers 16', 16'$_2$ are removed, the ultraviolet light may be directed through one side 18C or 18$C_2$, where it transmits through the substrate 10C or 10$C_2$ to expose the primers 34", 36" at both surfaces.

Removal of 3' photocleavable blocking groups 70 generates the unblocked cleavable first nuclease resistant primers 78 and the unblocked uncleavable second nuclease resistant primers 80. The unblocked cleavable first nuclease resistant primers 78 are similar to the cleavable first primers 34 described in reference to FIG. 2A, except that they also include the nuclease resistant modification 68. Similarly, the unblocked uncleavable second nuclease resistant primers 80 are similar to the uncleavable second primers 36 described in reference to FIG. 2A, except that they also include the nuclease resistant modification 68. Thus, the final flow cell includes two different primers sets 50C, 52C at the different regions 58", 60".

When the method shown and described in reference to FIG. 6A through FIG. 6I is performed with two bonded patterned structures 74, 74', as shown in FIG. 8, additional processes may be involved when performing the unblocking described in FIG. 6B.

As shown in FIG. 8, the patterned structure 74 (and thus its substrate 10C) is part of the flow cell 72 including a second patterned structure 74' opposed to the patterned structure 74 (and thus a second substrate 10$C_2$ opposed to the substrate 10C). As shown in FIG. 8, the second substrate 10$C_2$ includes second depressions 12$_2$ separated by second interstitial regions 14$_2$, wherein each second depression 12$_2$ includes a second ultraviolet light blocking layer 16'$_2$, and a second grafted layer 32'$_2$ or 32"$_2$ applied to a surface of the second substrate 10$C_2$, the second grafted layer 32'$_2$ or 32"$_2$ including a second polymeric hydrogel 28$_2$ and a second primer set 30'$_2$ or 30"$_2$ attached thereto. In the example involving the method of FIG. 6A through FIG. 6H, the second primer set 30'$_2$ includes the cleavable first nuclease resistant primers 34" and the uncleavable second nuclease resistant primers 36".

When the flow cell 72 of FIG. 8 is used in the method of FIG. 6A through FIG. 6I, prior to directing the ultraviolet light through the substrates 10C, 10$C_2$ (for unblocking as described in reference to FIG. 6B), the method further comprises introducing an ultraviolet light absorbing material into the flow cell 72; and after directing the ultraviolet light through the substrate 10C, 10$C_2$ (for unblocking as described in reference to FIG. 6B), the method further comprises removing the ultraviolet light absorbing material from the flow cell 72. An example of the ultraviolet light absorbing material is a colloidal dispersion of carbon black, other UV absorbing pigments, or paramagnetic beads.

The ultraviolet light absorbing material (and any other fluids) may be directed into a flow channel 92 of the flow cell 72 through an input port (or inlet) 94 and may be removed from the flow channel 92 through an output port (or outlet) 96.

As described in reference to FIG. 6B, during unblocking, ultraviolet light is introduced through the side 18C of the substrate 10C. When two patterned structures 74, 74' are used, ultraviolet light should be directed through both sides 18C and 18$C_2$ of the respective substrates 10C, 10$C_2$. The UV light will be able to transmit through the substrate 10C, 10$C_2$ and will be blocked by the respective UV light blocking layers 16', 16'$_2$. If the ultraviolet light absorbing material were not present in the flow channel 92, the UV light that transmits through the substrate 10C at region 60" could reach the primer set 30'$_2$ of the other substrate 10$C_2$, and the UV light that transmits through the second substrate 10$C_2$ at region 60"$_2$ could reach the primer set 30' of the substrate 10C. This is undesirable, as the primers 34", 36" and the primers 34"$_2$, 36"$_2$ positioned, respectively, in the regions 58" and 58"$_2$ should not be unblocked at this point in the method and thus should not be exposed to the ultraviolet light. The ultraviolet light absorbing material can block the light transmitted through the substrate 10C and 10$C_2$ from reaching the opposed substrate 10$C_2$ and 10C.

Referring now to FIG. 7A through FIG. 7M, this example of the method utilizes the primer set 30". The primer set 30" includes 3' blocked uncleavable first pre-primers 46 and 3' blocked uncleavable second pre-primers 48. In one example, 3' blocked uncleavable first pre-primers 46 includes a truncated sequence of the cleavable first primer 34 that does not include the cleavage site 54 or 3' end nucleotide(s), and also includes 3' photocleavable blocking group 70 at 3' end of the truncated sequence. In this example, 3' blocked uncleavable second pre-primers 48 includes a truncated sequence of the cleavable second primer 40 that does not include the cleavage site 54 or 3' end nucleotide(s), and also includes 3' photocleavable blocking group 70 at 3' end of the truncated sequence. In one example, the primer set 30" includes a truncated P5 sequence and a truncated P7 sequence and neither of these sequences includes the cleavage site 54. These pre-primers 46, 48 are shown in FIG. 7A. In another example, the pre-primers 46, 48 may be the full uncleavable primer sequence (e.g., P5 and P7) with the respective photocleavable blocking groups 70 positioned 5 bases to 10 bases from 3' end so that a truncated primer is generated during processing and is subsequently used to generate the full cleavable or uncleavable primer.

In FIG. 7A, each depression 12 includes an ultraviolet light blocking layer 16' (or 16 if the substrate 10A or 10B is used) positioned at a first region 58", and a second region 60" of each depression 12 is transparent to ultraviolet light, wherein the second region 60" corresponds with the predetermined region 38 (where at least some primer alteration is to take place).

While not shown in FIG. 7A through FIG. 7M, this example of the method involves generating the patterned structure(s) 74, 74' (FIG. 8), bonding the patterned structures 74, 74' together or bonding one patterned structure 74 and a lid (not shown) together, and then performing the pre-primer 46, 48 alteration in the flow cell 72.

To generate each patterned structure 74, 74', the depressions 12 are defined in the substrate 10A, 10B, or 10C and the UV light blocking layer 16 or 16' is incorporated (e.g., applied, embedded, etc.) into the first region 58, 58" of the substrate 10A, 10B, 10C as described in reference to FIG. 1A, FIG. 1B, or FIG. 1C. Then, the grafted layer 32" is applied. In this example method, applying the grafted layer 32" involves introducing the grafted layer 32" to the depressions 12 and the interstitial regions 14; and removing the grafted layer 32" from the interstitial regions 14. Any example of the polymeric hydrogel 28 disclosed herein is applied over the substrate 10A, 10B, or 10C using any suitable deposition technique, and before or after the polymeric hydrogel 28 is applied, the initial primer set 30" (including pre-primers 46, 48) is grafted to the polymeric hydrogel 28 using any suitable grafting technique. In one example, prior to grafting the pre-primers 46, 48 and after the polymeric hydrogel 28 is applied, the method includes removing the polymeric hydrogel 28 from the interstitial regions 14 using the polishing process disclosed herein. The pre-primers 46, 48 are then grafted to the polymeric hydrogel 28 in the depressions 12. In another example, the pre-primers 46, 48 are grafted to the polymeric hydrogel 28 (either before or after it is applied to the substrate 10C), and the method includes removing the grafted layer 32" from the interstitial regions 14 using the polishing process disclosed herein. The resulting patterned structure 74, 74' includes the grafted layer 32" within each depression 12, and the interstitial regions 14, which are free of the grafted layer 32". One depression 12 of the patterned structure 74 is shown in FIG. 7A.

In the example shown in FIG. 7A through FIG. 7M, at a first predetermined region 38 of the grafted layer 32" within the second region 60" of at least some of the depressions 12: 3' blocked uncleavable first pre-primers 46 are altered to introduce cleavable first primers 34; and 3' blocked uncleavable second pre-primers 48 are altered to introduce uncleavable second primers 36. Also in the example shown in FIG. 7A through FIG. 7M, at a second predetermined region 38' of the grafted layer 32" within the first region 58" of at least some of the depressions 12: 3' blocked uncleavable first pre-primers 46 are altered to introduce uncleavable first primers 42; and 3' blocked uncleavable second pre-primers 48 are altered to introduce cleavable second primers 40. The alteration of the pre-primers 46, 48 at the first predetermined region 38 is shown in FIG. 7B through FIG. 7G and the alteration of the pre-primers 46, 48 at the second predetermined region 38' is shown in FIG. 7H through FIG. 7M.

The alteration of 3' blocked uncleavable first pre-primers 46 to introduce cleavable first primers 34 at the first predetermined region 38 of the grafted layer 32" within the second region 60" of at least some of the depressions 12 involves: directing ultraviolet light through the substrate 10C, thereby removing 3' photocleavable blocking groups 70 i) from 3' blocked uncleavable first pre-primers 46 to generate unblocked uncleavable first pre-primers 98 that overlie the second region 60" and ii) from 3' blocked uncleavable second pre-primers 48 to generate unblocked uncleavable second pre-primers 100 that overlie the second region 60", whereby 3' blocked uncleavable first pre-primers 46 and 3' blocked uncleavable second pre-primers 48 that overlie the first region 58" remain blocked (FIG. 7B); respectively hybridizing first primer generation templates 76' to the unblocked uncleavable first pre-primers 98 that overlie the second region 60" and to 3' blocked uncleavable first pre-primers 46 that overlie the first region 58" (FIG. 7C); using a nucleotide mixture including a cleavable base (e.g., a uracil base or 8-oxoguanine or any other cleavable nucleotide that can be incorporated by a polymerase), initiating polymerase extension along the first primer generation templates 76' at 3' ends of the unblocked uncleavable first pre-primers 98 to generate the cleavable first primers 34 (FIG. 7D); and dehybridizing the first primer generation templates 76' (FIG. 7E).

FIG. 7B depicts the introduction of ultraviolet light through the side 18C of the substrate 10C. The wavelength (s) of the UV light are sufficient to remove 3' photocleavable blocking groups 70 from the uncleavable first pre-primers 46 and the uncleavable second pre-primers 48 that are exposed to the light. In this example, the UV light is introduced at the side 18C and is transmitted through the substrate 10C at the second region 60". Thus, the uncleavable first pre-primers 46 and the uncleavable second pre-primers 48 at the second region 60" are exposed to the UV light, which triggers the removal of 3' photocleavable blocking groups 70. The unblocked uncleavable first pre-primers and the unblocked uncleavable second pre-primers are shown at reference numerals 98 and 100, respectively. In contrast, the UV light blocking layer 16' blocks the light from reaching the uncleavable first pre-primers 46 and the uncleavable second pre-primers 48 at the first region 58", and thus these pre-primers 46, 48 remain 3' blocked.

The method may further include dephosphorylating the unblocked uncleavable first pre-primers and the unblocked uncleavable second pre-primers 98, 100 at 3' ends. The phosphate terminated 3' ends may be dephosphorylated by introducing an enzyme with 3'-phosphatase activity (e.g., T4 phage polynucleotide kinase (PNK) or alkaline phosphatase (AP or ALP)). These enzymes process the phosphate ends, converting them into 3'-hydroxyls and render them ready for primer alteration.

First primer regeneration templates 76' are then introduced into the flow cell 72. Each first primer regeneration template 76' is a complement of the sequence of the cleavable first primer 34 and of the uncleavable first primer 42. The nucleotide mixture used during extension of the unblocked uncleavable first pre-primers 98 will dictate whether the generated primer is cleavable or uncleavable. Thus, each first primer regeneration template 76' includes a first portion 82' that is complementary to the sequence of the unblocked uncleavable first pre-primers 98 (which is a truncated version of the cleavable first primer 34 and of the uncleavable first primer 42) and a second portion 84' that is complementary to the remainder of the cleavable first primer 34 and to the remainder of the uncleavable first primer 42. The first primer regeneration templates 76' are introduced at conditions that enable the first primer regeneration templates 76' to hybridize to the unblocked uncleavable first pre-primers 98 and to the uncleavable first pre-primers 46 that remain intact at the first region 58". The hybridized primer regeneration templates 76' are shown in FIG. 7C.

A nucleotide mixture, containing a cleavable nucleotide, other non-cleavable nucleotides, and a polymerase, is then introduced into the flow cell 72. The cleavable nucleotide includes a uracil base or 8-oxoguanine or any other cleavable nucleotide that can be incorporated by a polymerase. Other non-cleavable nucleotides in this mixture include the following bases: adenine, cytosine, and guanine. Any polymerase that can accept these nucleotides, and that can successfully incorporate the base of these nucleotides at the 3' end of the unblocked uncleavable first pre-primers 98 may be used. This example of the nucleotide mixture may also include any example of the liquid carrier and the catalytic metal(s) set forth herein.

The temperature of the flow cell 72 may be adjusted to initiate a template extension reaction. The polymerase enables the extension of 3' end of the unblocked uncleavable first pre-primers 98 using the second portion 84' of the first primer regeneration template 76' as a template. Because i) the extension reaction is guided by the second portion 84' of the first primer regeneration template 76', ii) the second portion 84' is complementary to the missing portion of the cleavable first primer 34, and iii) a cleavable nucleotide is used in the nucleotide mixture, the polymerase extension along the second portion 84' generates the cleavable first primer 34 with the cleavage site 54. The cleavable first primer 34 is shown in FIG. 7D.

While some of the first primer regeneration templates 76' may hybridize to the intact first pre-primers 46 at the first region 58", polymerase extension does not occur at these pre-primers 46.

Once the cleavable first primers 34 are generated (FIG. 7D), the first primer regeneration templates 76' are dehybridized (i.e., denatured) and are removed from the flow cell 72 (e.g., using a wash solution).

The 3' blocked uncleavable second pre-primers 48, which have already been unblocked as shown and described in reference to FIG. 7B, and then altered. The alteration of 3' blocked uncleavable second pre-primers 48 to introduce uncleavable second primers 36 at the first predetermined region 38 of the grafted layer 32" within the second region 60" of at least some of the depressions 12 involves: respectively hybridizing second primer generation templates 86' to the unblocked uncleavable second pre-primers 100 that overlie the second region 60" and to 3' blocked uncleavable second pre-primers 48 that overlie the first region 58" (FIG. 7E); using a nucleotide mixture including a thymine base, initiating polymerase extension along the second primer generation templates 86' at 3' ends of the unblocked uncleavable second pre-primers 100 to generate the uncleavable second primers 36 (FIG. 7F); and dehybridizing the second primer generation templates 86' (FIG. 7G).

Each second primer regeneration template 86' is a complement of the sequence of the uncleavable second primer 36 and of the cleavable second primer 40. The nucleotide mixture used during extension of the unblocked uncleavable second pre-primers 100 will dictate whether the generated primer is cleavable or uncleavable. Thus, each second primer regeneration template 86' includes a first portion 88' that is complementary to the sequence of the unblocked uncleavable second pre-primers 100 (which is a truncated version of the uncleavable second primer 36 and of the cleavable second primer 40) and a second portion 90' that is complementary to the remainder of the uncleavable second primer 36 and to the remainder of the cleavable second primer 40. The second primer regeneration templates 86' are introduced at conditions that enable the second primer regeneration template 86' to hybridize to the unblocked uncleavable second pre-primers 100 at the second region 60" and to the second pre-primers 48 that remain intact at the first region 58". The hybridized primer regeneration templates 86' are shown in FIG. 7E.

A nucleotide mixture containing non-cleavable nucleotides and a polymerase are introduced into the flow cell 72. The non-cleavable nucleotides include the following bases: adenine, cytosine, guanine and thymine. Any polymerase that can accept the non-cleavable nucleotide, and that can successfully incorporate the base of the non-cleavable nucleotide at 3' end of the unblocked uncleavable second pre-primers 100 may be used. This example of the nucleotide mixture may also include any example of the liquid carrier and the catalytic metal(s) set forth herein.

The temperature of the flow cell 72 may be adjusted to initiate a template extension reaction. The polymerase enables the extension of 3' end of the unblocked uncleavable second pre-primers 100 using the second portion 90' of the second primer regeneration template 86' as a template. Because i) the extension reaction is guided by the second portion 90' of the second primer regeneration template 86', ii) the second portion 90' is complementary to the missing portion of the uncleavable second primer 36, and iii) non-cleavable nucleotides are used, the polymerase extension along the second portion 90' generates the uncleavable second primer 36 without any cleavage site 54. The uncleavable second primer 36 is shown in FIG. 7F.

While some of the second primer regeneration templates 86' may hybridize to the intact second pre-primers 48 at the first region 58", polymerase extension does not occur at these pre-primers 48.

Once the uncleavable second primers 36 are generated (FIG. 7F), the second primer regeneration templates 86' are dehybridized (i.e., denatured) and are removed from the flow cell 72 (e.g., using a wash solution).

As shown in FIG. 7G, both of the pre-primers 46, 48 at the predetermined region 38 of the grafted layer 32" have been altered to introduce the cleavable first primer 34 and the uncleavable second primer 36. This introduces the primer set 50A within one region of the depressions 12.

Also as shown in FIG. 7G, both of the pre-primers 46, 48 at the predetermined region 38' of the grafted layer 32" remain unaltered, and thus remain blocked with 3' photocleavable blocking group 70. These pre-primers 46, 48 may be exposed to an unblocking treatment so that they can be altered to introduce the cleavable second primer 40 and the uncleavable first primer 42 to the predetermined region 38'.

Figure 7H:
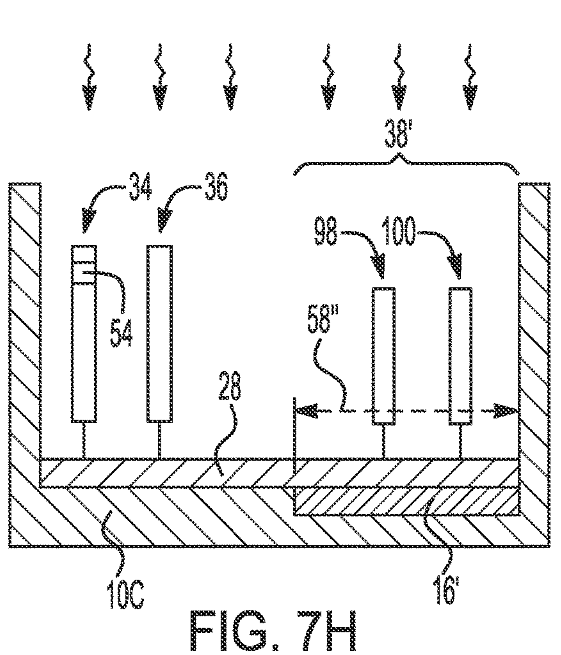
Figure 8:
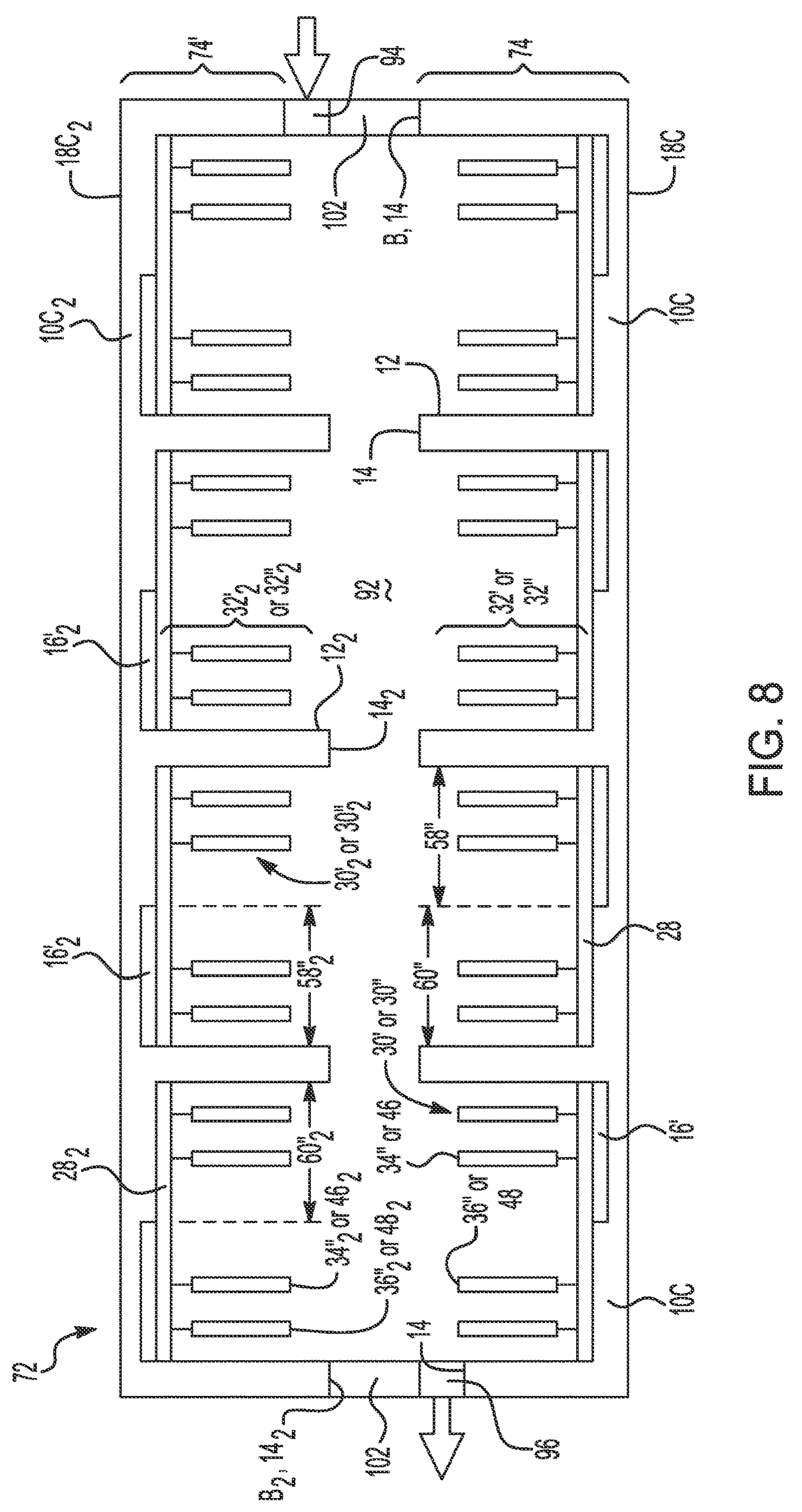
FIG. 8 is a cross sectional view of an example of a flow cell including two patterned structures bonded together and before primer set alteration has taken place.

As such, the method further includes directing ultraviolet light at the surface of the substrate 10C (as shown in FIG. 7H), thereby removing 3' photocleavable blocking groups 70 i) from 3' blocked uncleavable first pre-primers 46 to generate unblocked uncleavable first pre-primers 98 that overlie the first region 58" and ii) from 3' blocked uncleavable second pre-primers 48 to generate unblocked uncleavable second pre-primers 100 that overlie the first region 58". The ultraviolet light may be selected with a suitable wavelength to initiate unblocking/deblocking.

When the flow cell 72 includes a UV transparent lid, the UV light may be directed through the lid toward the first and second pre-primers 46, 48 at the surface of the substrate 10C.

Alternatively, the flow cell 72 may include two patterned structures 74, 74' (as shown in FIG. 8). In one example, the unblocking process may be performed by directing the ultraviolet light through both of the sides 18C, 18$C_2$, because the UV light that transmits through the substrate 10C at region 60" could reach the primer set 30"$_2$ of the opposed patterned structure 74', and the UV light that transmits through the second substrate 10$C_2$ at region 60"$_2$ could reach the primer set 30" of the opposed patterned structure 74. In another example, the UV light absorbing layers 16', 16'$_2$ (or layer 16 if the substrates 10A or 10B are used) may be removed before directing the ultraviolet light through one side 18C or 18$C_2$. The UV light blocking layers 16', 16'$_2$ may be removed as described in reference to the FIG. 3 series, where the wet etching is performed in a flow through manner and is followed one of the adhesion promoting processes described herein. The etchant may be introduced via an input port 94 (FIG. 8), and then the removed UV light blocking layers 16', 16'$_2$ may be removed from the flow cell 72 via an output port 96 (FIG. 8). After the UV light blocking layers 16', 16'$_2$ are removed, the ultraviolet light may be directed through one side 18C or 18$C_2$, where it transmits through the substrate 10C or 10$C_2$ to expose the first and second pre-primers 46, 48 at both surfaces.

Removal of 3' photocleavable blocking groups 70 generates the unblocked first pre-primers 98 and the unblocked second pre-primers 100 at the first region 58", as shown in FIG. 7H. The method may further include dephosphorylating the unblocked uncleavable first pre-primers and the unblocked uncleavable second pre-primers 98, 100 at 3' ends. The phosphate terminated 3' ends may be dephosphorylated by introducing an enzyme with 3'-phosphatase activity (e.g., T4 phage polynucleotide kinase (PNK) or alkaline phosphatase (AP or ALP)). These enzymes process the phosphate ends, converting them into 3'-hydroxyls and render them ready for primer alteration.

The unblocked first pre-primers 98 and the unblocked second pre-primers 100 are ready for alteration at the second predetermined region 38' of the grafted layer 32".

Figure 7I:
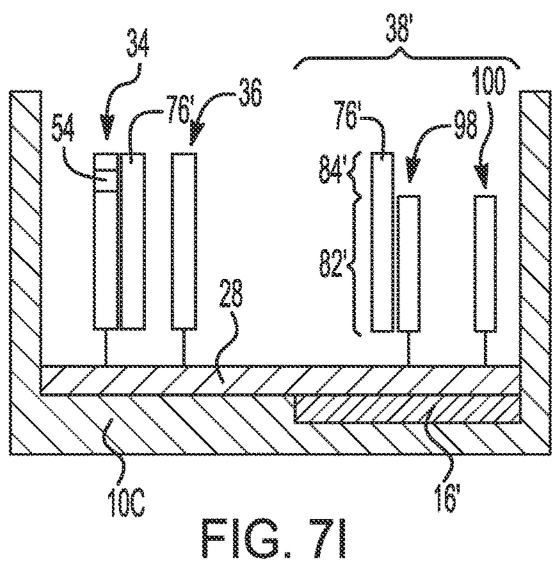
Figure 7J:
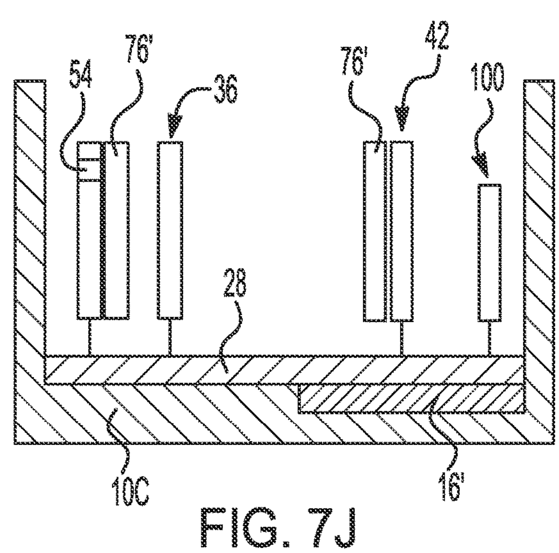
Figure 7K:
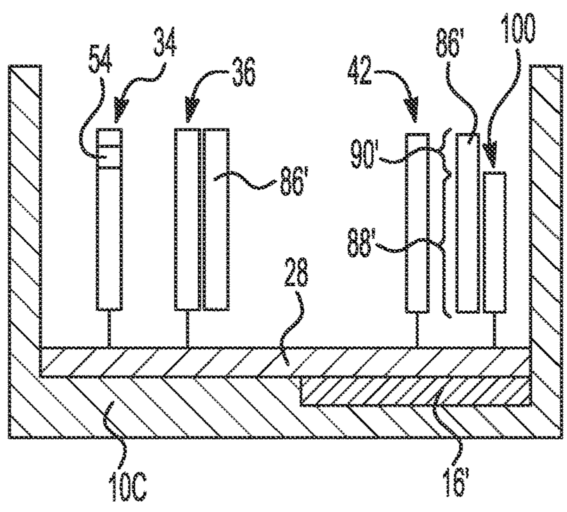

The 3' blocked uncleavable second pre-primers 48 at the second predetermined region 38', which have already been unblocked as shown and described in reference to FIG. 7H, are then altered. At the second predetermined region 38' of the grafted layer 32" within the first region 58" of at least some of the depressions 12, altering 3' blocked uncleavable first pre-primers to introduce uncleavable first primers 42 involves: respectively hybridizing first primer generation templates 76' to the unblocked uncleavable first pre-primers 98 that overlie the first region 58" and to the cleavable first primers 34 that overlie the second region 60" (FIG. 7I); initiating polymerase extension along the first primer generation templates 76' at 3' ends of the unblocked uncleavable first pre-primers 98 to generate the uncleavable first primers 42 (FIG. 7J); and dehybridizing the first primer generation templates 76' (FIG. 7K).

The first primer regeneration templates 76' are again introduced into the flow cell 72. As mentioned above, each first primer regeneration template 76' is a complement of the sequence of the cleavable first primer 34 and of the uncleavable first primer 42, and the nucleotide mixture used during extension of the unblocked uncleavable first pre-primers 98 will dictate whether the generated primer is cleavable or uncleavable. The first primer regeneration templates 76' are introduced at conditions that enable the first primer regeneration templates 76' to hybridize to the unblocked uncleavable first pre-primers 98 at the first region 58" and to the cleavable first primers 34 generated at the second region 60". The hybridized primer regeneration templates 76' are shown in FIG. 7I.

In this example, the nucleotide mixture introduced into the flow cell 72 includes non-cleavable nucleotides and a polymerase. The non-cleavable nucleotides include the following bases: adenine, cytosine, guanine and thymine. Any polymerase that can accept these nucleotides, and that can successfully incorporate the base of these nucleotides at the 3' end of the unblocked uncleavable first pre-primers 98 at the first region 58" may be used. This example of the nucleotide mixture may also include any example of the liquid carrier and the catalytic metal(s) set forth herein.

The temperature of the flow cell 72 may be adjusted to initiate a template extension reaction. The polymerase enables the extension of 3' end of the unblocked uncleavable first pre-primers 98 using the second portion 84' of the first primer regeneration template 76' as a template. Because i) the extension reaction is guided by the second portion 84' of the first primer regeneration template 76', ii) the second portion 84' is complementary to the missing portion of the uncleavable first primer 42, and iii) non-cleavable nucleotides are used, the polymerase extension along the second portion 84' generates the uncleavable first primer 42 without the cleavage site 54. The uncleavable first primer 42 is shown in FIG. 7J.

While some of the first primer regeneration templates 76' may hybridize to the intact cleavable first primers 34 at the second region 60", polymerase extension does not occur at these cleavable first primers 34.

Once the uncleavable first primers 42 are generated (FIG. 7J) in the first region 58", the first primer regeneration templates 76' are dehybridized (i.e., denatured) and are removed from the flow cell 72 (e.g., using a wash solution).

Figure 7L:
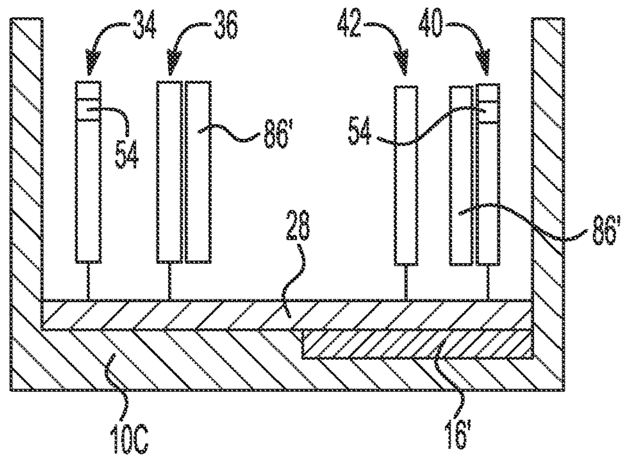
Figure 7M:
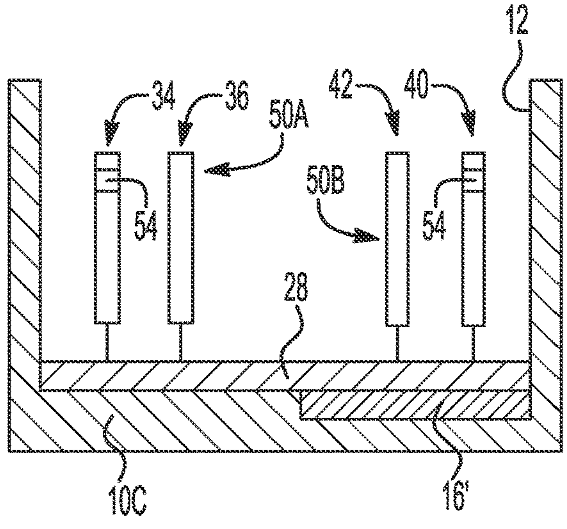

The 3' blocked uncleavable second pre-primers 48 at the first region 58", which have already been unblocked as shown and described in reference to FIG. 7H, are then altered. At the second predetermined region 38' of the grafted layer 32" within the first region 58" of at least some of the depressions 12, altering 3' blocked uncleavable second pre-primers 48 to introduce cleavable second primers 40 involves: respectively hybridizing second primer generation templates 86' to the unblocked uncleavable second pre-primers 100 that overlie the first region 58" and to the uncleavable second primers 36 that overlie the second region 60" (FIG. 7K); using a nucleotide mixture including a cleavable base, initiating polymerase extension along the second primer generation templates 86' at 3' ends of the unblocked uncleavable second pre-primers 100 to generate the cleavable second primers 40 (FIG. 7L); and dehybridizing the second primer generation templates 86' (FIG. 7M).

The second primer regeneration templates 86' are again introduced into the flow cell 72, as shown at FIG. 7K. As mentioned above, each second primer regeneration template 86' is a complement of the sequence of the uncleavable second primer 36 and of the cleavable second primer 40, and the nucleotide mixture used during extension of the unblocked uncleavable second pre-primers 100 will dictate whether the generated primer is cleavable or uncleavable. The second primer regeneration templates 86' are introduced at conditions that enable the second primer regeneration templates 86' to hybridize to the unblocked uncleavable second pre-primers 100 at the first region 58" and to the uncleavable second primers 36 generated at the second region 60". The hybridized primer regeneration templates 86' are shown in FIG. 7K.

In this example, the nucleotide mixture introduced into the flow cell 72 includes a cleavable nucleotide, other non-cleavable nucleotides, and a polymerase. The cleavable nucleotide includes a uracil base or any other cleavable nucleotide that can be incorporated by a polymerase. The other non-cleavable nucleotides include the following bases: adenine, cytosine, and guanine. Any polymerase that can accept these nucleotides, and that can successfully incorporate the base of these nucleotides at 3' end of the unblocked uncleavable second pre-primers 100 at the first region 58" may be used. This example of the nucleotide mixture may also include any example of the liquid carrier and the catalytic metal(s) set forth herein.

The temperature of the flow cell 72 may be adjusted to initiate a template extension reaction. The polymerase enables the extension of 3' end of the unblocked uncleavable second pre-primers 100 using the second portion 90' of the second primer regeneration template 86' as a template. Because i) the extension reaction is guided by the second portion 90' of the second primer regeneration template 86', ii) the second portion 90' is complementary to the missing portion of the cleavable second primer 40, and iii) a cleavable nucleotide is used, the polymerase extension along the second portion 90' generates the cleavable second primer 40 with the cleavage site 54. The cleavable second primer 40 is shown in FIG. 7L.

While some of the second primer regeneration templates 86' may hybridize to the intact uncleavable second primers 36 at the second region 60", polymerase extension does not occur at these uncleavable second primers 36.

Once the cleavable second primers 40 are generated (FIG. 7L) in the first region 58", the second primer regeneration templates 86' are dehybridized (i.e., denatured) and are removed from the flow cell 72 (e.g., using a wash solution).

As shown in FIG. 7M, both of the pre-primers 46, 48 at the second predetermined region 38' of the grafted layer 32" have been altered to introduce the uncleavable first primer 42 and the cleavable second primer 40. This introduces the primer set 50B within another region of the depressions 12.

When the flow cell 72 of FIG. 8 is used in the method of FIG. 7A through FIG. 7M, prior to directing the ultraviolet light through the substrates 10C, 10$C_2$ (for unblocking the pre-primers 46, 48 in the region 60" as described in reference to FIG. 7B), the method further comprises introducing an ultraviolet light absorbing material into the flow cell 72; and after directing the ultraviolet light through the substrate 10C, 10$C_2$, the method further comprises removing the ultraviolet light absorbing material from the flow cell 72. Any example of the ultraviolet light absorbing material disclosed herein may be used.

The ultraviolet light absorbing material (and any other fluids) may be directed into a flow channel 92 of the flow cell 72 through an input port (or inlet) 94 and may be removed from the flow channel 92 through an output port (or outlet) 96.

As described in reference to FIG. 7B, during unblocking, ultraviolet light is introduced through the side 18C of the substrate 10C. When two patterned structures 74, 74' are used, ultraviolet light should be directed through both sides 18C and 18$C_2$ of the respective substrates 10C, 10$C_2$. The UV light will be able to transmit through the substrate 10C, 10$C_2$ and will be blocked by the respective UV light blocking layers 16', 16'$_2$. If the ultraviolet light absorbing material were not present in the flow channel 92, the UV light that transmits through the substrate 10C at region 60" could reach the primer set 30"$_2$ of the other substrate 10$C_2$, and the UV light that transmits through the second substrate 10$C_2$ at region 60"$_2$ could reach the primer set 30" of the substrate 10C. This is undesirable, as the pre-primers 46, 48 and the primers 46$_2$, 48$_2$ positioned, respectively, in the regions 58" and 58"$_2$ should not be unblocked at this point in the method and thus should not be exposed to the ultraviolet light. The ultraviolet light absorbing material in the flow channel 92 can block the light transmitted through the substrate 10C and 10$C_2$ from reaching the opposed substrate 10$C_2$ and 10C.

In any of the example methods disclosed herein, the predetermined region 38 of the grafted layer 32, 32', 32" (where at least some primer alteration is to take place) may make up about one half (½) of each of at least some of the depressions 12, 12'.

Flow Cells

As mentioned, FIG. 8 illustrates an example flow cell 72 including two patterned structures 74, 74' bonded together. While not shown, it is to be understood that the patterned structure 74 may be bonded to a UV transparent lid to generate another example of the flow cell.

The flow channel 92 defined between the patterned structures 74, 74' is in fluid communication with an inlet/input port 94 and an outlet/output port 96. The inlet 94 allows fluids to be introduced into the flow channel 92, and the outlet 96 allows fluid to be extracted from the flow channel 92. Each of the inlets 94 and outlets 96 is fluidly connected to a fluidic control system (including, e.g., reservoirs, pumps, valves, waste containers, and the like) which controls fluid introduction and expulsion.

The inlet 94 and outlet 96 of each flow channel 12 may be positioned at opposed sides of the flow cell 72 (as shown in FIG. 8), at opposed ends of the flow cell 72, or anywhere along the length and width of the flow channel 92 that enables desirable fluid flow.

The patterned structures 74, 74' may be bonded together at a bonding region B, $B_2$. In the example shown in FIG. 8, the bonding region B, $B_2$ corresponds with the interstitial regions 14, 14$_2$ that are located at the perimeter of the patterned structures 74, 74'. A separate material 102 may be applied to the bonding regions B, $B_2$ to secure the patterned structures 74, 74' together. This separate material 102 material 36 defines at least a portion of the walls of the flow channel 92. Any suitable separate material 102, such as an adhesive, a radiation-absorbing material that aids in bonding, etc., may be used to bond the patterned structures 74, 74' together.

The architecture of the patterned structures 74, 74' shown in FIG. 8 includes the depressions 12, 12$_2$ defined in the substrates 10C, 10$C_2$, and the grafted layers 32' or 32" and 32'$_2$ or 32"$_2$ positioned in the depressions 12, 12$_2$. In the final flow cell 72, the initial primer sets 30' or 30" may be altered in accordance with the methods described in reference to the FIG. 6 series or the FIG. 7 series. Alternatively, the architecture of each depression 12 or 12' in the flow cell 72 may be similar to that shown in FIG. 3G, or in FIG. 4H, or in FIG. 5H.

The flow cell 72 shown in FIG. 8 includes a single flow channel 92 defined between the two bonded patterned structures 74, 74'. Other flow cells may be generated with several flow channels 92. An example of a flow cell 72' with eight different flow channels 92 is shown, from a top view, in FIG. 9. While eight flow channels 92 are shown, it is to be understood that any number of flow channels 92 may be included in the flow cell 72' (e.g., four flow channels 92, etc.).

Figures 9, 10A, 10B:
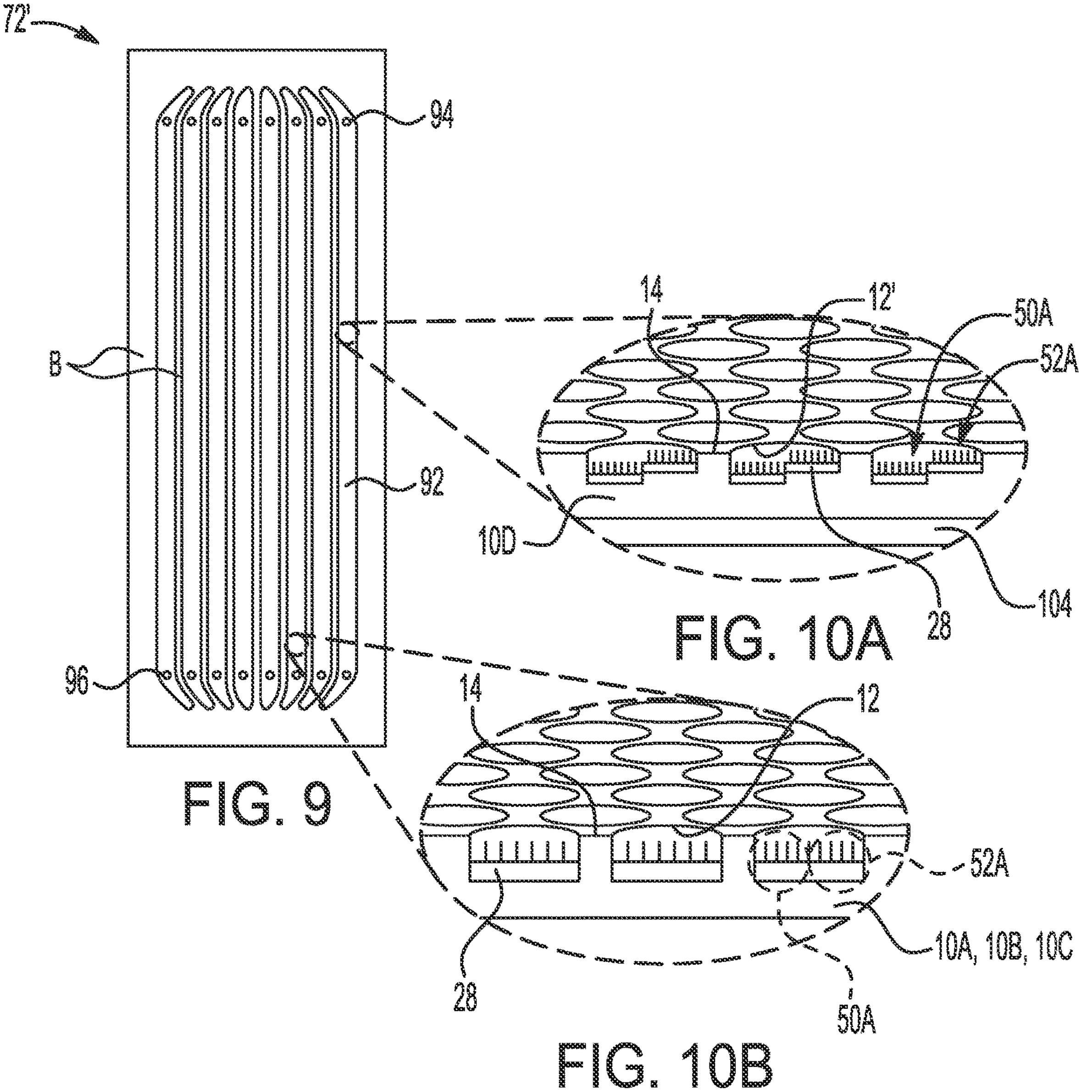
FIG. 9 is a top view of an example of a flow cell.
FIG. 10A is an enlarged, and partially cutaway view of an example of a flow channel of the flow cell.
FIG. 10B is an enlarged, and partially cutaway view of a different example of a flow channel of the flow cell.

When multiple flow channels 92 are included, each includes its own inlet 94 and outlet 96. The inlet 94 and outlet 96 of each flow channel 92 may be positioned at opposed ends of the flow cell 72' as shown in FIG. 9. The inlets 94 and outlets 96 of the respective flow channels 92 may alternatively be positioned anywhere along the length and width of the flow channel 92 that enables desirable fluid flow.

In the example shown in FIG. 9, each flow channel 92 may be isolated from each other flow channel 92 so that fluid introduced into a flow channel 92 does not flow into adjacent flow channel(s) 92. In this example, the bonding region B may include the perimeter of the substrate 10A, 10B, 10C, 10D and non-patterned areas of the substrate 10A, 10B, 10C, 10D that separate the flow channels 92.

Examples of the architecture within the flow channels 92 are depicted in FIG. 10A and FIG. 10B.

The architecture in FIG. 10A includes the substrate 10D positioned over a UV transparent base support 104. Each multi-depth depression 12' includes the polymeric hydrogel 28 with different primer sets 50A, 52A (or 50B, 52B) respectively attached within the deep and shallow portions 24, 26 of the multi-depth depressions 12'. This architecture may be formed as described in reference to the FIG. 4 series or the FIG. 5 series. In the example of FIG. 10A, a similar patterned structure or a lid may be bonded to the substrate 10D.

The architecture in FIG. 10B includes the substrate 10A, 10B, 10C, with the UV light blocking layer 16, 16' removed. Each depression 12 includes the polymeric hydrogel 28 with different primer sets 50A, 52A (or 50B, 52B or 50C, 52C) respectively attached at spatially separated regions. The depressions 12 are separated by interstitial regions 14. This architecture may be formed as described in reference to the FIG. 3 series, or the FIG. 6 series, or the FIG. 7 series. In the example of FIG. 10B, a similar patterned structure or a lid may be bonded to the substrate 10A, 10B, 10C.

Methods for Using the Flow Cells

Examples of the flow cell 72, 72' disclosed herein including the different primer sets 50A, 52A or 50B, 52B or 50C, 52C attached to different regions of the polymeric hydrogel 28 may be used in a simultaneously paired-end read sequencing method. In this method, a library template is seeded within a depression 12, 12' and is amplified across the 50A, 52A or 50B, 52B or 50C, 52C. Forward and reverse strands are generated within the depression 12, 12'. The orthogonal cleaving chemistry of the sets 50A, 52A or 50B, 52B or 50C, 52C enables reverse strands to be cleaved from one region, e.g., region 38, while forward strands are cleaved from the other, adjacent region, e.g., region 38'. Thus, a cluster of forward strands can be generated in one region (e.g., region 38) and a cluster of reverse strands can be generated in another region (e.g., at region 38'). The clusters can be sequenced simultaneously (e.g., using sequencing-by-synthesis methods), and the spatial separation enables simultaneous paired-end reads to be obtained.

Kits

Any example of the flow cell 72, 72' may be included in a kit.

One example of the kit includes a flow cell 72, 72', which includes: a substrate 10A, 10B, 10C, 10D including depressions 12, 12' separated by interstitial regions 14; a polymeric hydrogel 28 applied within each of the depressions 12, 12'; and a primer set 30, 30' grafted to the polymeric hydrogel 28, the primer set 30, 30' including cleavable first primers 34, 34' and uncleavable second primers 36, 36'; and a nuclease to digest the some of the cleavable first primers 34, 34' and the some of the uncleavable second primers 36, 36' and generate a primer depleted portion 64 of the grafted layer 32, 32'; and one of: a primer mixture including cleavable second primers 40, 40' and uncleavable first primers 42, 42'; or first primer regeneration templates 76; and second primer regeneration templates 86.

Another example of the kit includes a flow cell 72, 72', which includes: a substrate 10A, 10B, 10C, 10D including depressions 12, 12' separated by interstitial regions 14; a polymeric hydrogel 28 applied within each of the depressions 12, 12'; and a primer set 30" grafted to the polymeric hydrogel 28, the primer set 30" including 3' blocked uncleavable first pre-primers 46 and 3' blocked uncleavable second pre-primers 48; first primer generation templates 76; second primer generation templates 86; a first nucleotide mixture including a cleavable base and uncleavable bases; and a second nucleotide mixture including uncleavable bases.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A method, comprising:

applying a polymeric hydrogel to a surface of a substrate including:

a first region that is covered by an ultraviolet light blocking layer;

a second region that is adjacent to the first region and that is free of the ultraviolet light blocking layer; and depressions separated by interstitial regions, each depression defined within at least a portion of the first region and within at least a portion of the second region;

before or after applying the polymeric hydrogel, grafting a primer set to the polymeric hydrogel to form a grafted layer, the primer set including 3' blocked uncleavable first pre-primers and 3' blocked uncleavable second pre-primers;

removing the polymeric hydrogel or the grafted layer from the interstitial regions;

at a first predetermined region of the grafted layer within the depression and within the second region:

altering 3' blocked uncleavable first pre-primers to introduce cleavable first primers; and altering 3' blocked uncleavable second pre-primers to introduce uncleavable second primers; and at a second predetermined region of the grafted layer within the depression and within the first region:

altering 3' blocked uncleavable first pre-primers to introduce uncleavable first primers; and altering 3' blocked uncleavable second pre-primers to introduce cleavable second primers.

2. The method as defined in claim 1, wherein:

at the first predetermined region of the grafted layer, altering 3' blocked uncleavable first pre-primers to introduce cleavable first primers involves:

directing ultraviolet light through the substrate, thereby removing 3' photocleavable blocking groups i) from 3' blocked uncleavable first pre-primers to generate unblocked uncleavable first pre-primers that overlie the second region and ii) from 3' blocked uncleavable second pre-primers to generate unblocked uncleavable second pre-primers that overlie the second region, whereby 3' blocked uncleavable first pre-primers and 3' blocked uncleavable second pre-primers that overlie the first region remain blocked;

respectively hybridizing first primer generation templates to the unblocked uncleavable first pre-primers that overlie the second region and to 3' blocked uncleavable first pre-primers that overlie the first region;

using a nucleotide mixture including a cleavable base, initiating polymerase extension along the first primer generation templates at 3' ends of the unblocked uncleavable first pre-primers to generate the cleavable first primers; and dehybridizing the first primer generation templates; and at the first predetermined region of the grafted, altering the unblocked uncleavable second pre-primers to introduce uncleavable second primers involves:

respectively hybridizing second primer generation templates to the unblocked uncleavable second pre-primers that overlie the second region and to 3' blocked uncleavable second pre-primers that overlie the first region;

using a nucleotide mixture including a thymine base, initiating polymerase extension along the second primer generation templates at 3' ends of the unblocked uncleavable second pre-primers to generate the uncleavable second primers; and dehybridizing the second primer generation templates.

3. The method as defined in claim 2, wherein:

the substrate is part of a flow cell including a second substrate opposed to the substrate, the second substrate including second depressions separated by second interstitial regions and a second ultraviolet light blocking layer positioned to block ultraviolet light directed through the second substrate from reaching the second region of the substrate and to allow ultraviolet light directed through the second substrate to reach the first region of the substrate, wherein each second depression further includes a second grafted layer applied to the second depressions, the second grafted layer including a second polymeric hydrogel and a second primer set attached thereto, the second primer set including 3' blocked uncleavable first pre-primers and 3' blocked uncleavable second pre-primers;

directing ultraviolet light through the substrate involves directing ultraviolet light through each of the substrate and the second substrate;

prior to directing the ultraviolet light through the substrates, the method further comprises introducing an ultraviolet light absorbing material into the flow cell; and after directing the ultraviolet light through the substrates, the method further comprises removing the ultraviolet light absorbing material from the flow cell.

4. The method as defined in claim 2, further comprising directing ultraviolet light at the surface of the substrate, thereby removing 3' photocleavable blocking groups i) from 3' blocked uncleavable first pre-primers to generate unblocked uncleavable first pre-primers that overlie the first region and ii) from 3' blocked uncleavable second pre-primers to generate unblocked uncleavable second pre-primers that overlie the first region.

5. The method as defined in claim 4, wherein:

at the second predetermined region of the grafted layer, altering 3' blocked uncleavable first pre-primers to introduce uncleavable first primers involves:

respectively hybridizing first primer generation templates to the unblocked uncleavable first pre-primers that overlie the first region and to the cleavable first primers that overlie the second region;

initiating polymerase extension along the first primer generation templates at 3' ends of the unblocked uncleavable first pre-primers to generate the uncleavable first primers; and dehybridizing the first primer generation templates; and at the second predetermined region of the grafted layer within the first region of at least some of the depressions, altering 3' blocked uncleavable second pre-primers to introduce cleavable second primers involves:

respectively hybridizing second primer generation templates to the unblocked uncleavable second pre-primers that overlie the first region and to the uncleavable second primers that overlie the second region;

using a nucleotide mixture including a cleavable base, initiating polymerase extension along the second primer generation templates at 3' ends of the unblocked uncleavable second pre-primers to generate the cleavable second primers; and dehybridizing the second primer generation templates.

6. The method as defined in claim 4, wherein:

the substrate is part of a flow cell including a second substrate opposed to the substrate, the second substrate including second depressions separated by second interstitial regions and a second ultraviolet light blocking layer positioned to block ultraviolet light directed through the second substrate from reaching the second region of the substrate and to allow ultraviolet light directed through the second substrate to reach the first region of the substrate, wherein each second depression further includes a second grafted layer applied to the second depressions, the second grafted layer including a second polymeric hydrogel and a second primer set attached thereto, the second primer set including 3' blocked uncleavable first pre-primers and 3' blocked uncleavable second pre-primers; and prior to directing the ultraviolet light at the surface of the substrate, the method further comprises removing the ultraviolet light blocking layer and the second ultraviolet light blocking layer.

7. A kit, comprising:

a flow cell including:

a substrate including depressions separated by interstitial regions;

a polymeric hydrogel applied within each of the depressions; and a primer set grafted to the polymeric hydrogel, the primer set including 3' blocked uncleavable first pre-primers and 3' blocked uncleavable second pre-primers;

first primer generation templates;

second primer generation templates;

a first nucleotide mixture including a cleavable base and uncleavable bases; and a second nucleotide mixture including uncleavable bases.

8. The kit as defined in claim 7, wherein the flow cell includes an ultraviolet light blocking layer in a region of the substrate that corresponds with a predetermined region wherein 3' blocked uncleavable first pre-primers and 3' blocked uncleavable second pre-primers are to be altered.

9. The method as defined in claim 6, wherein removing the ultraviolet light blocking layer and the second ultraviolet light blocking layer involves:

wet etching the ultraviolet light blocking layer and the second ultraviolet light blocking layer, thereby creating respective gaps between the substrate and the grafted layer and between the second substrate and the second grafted layer; and increasing adhesion between the substrate and the grafted layer and between the second substrate and the second grafted layer.

10. The method as defined in claim 9, where wet etching involves exposure to a 1%-2% KOH solution or a sodium carbonate buffer for about 3 to 5 minutes, without mechanical stress.

* * * * *

SEQUENCE LISTING

```
Sequence total quantity: 18
SEQ ID NO: 1            moltype = DNA  length = 28
FEATURE                 Location/Qualifiers
source                  1..28
                        mol_type = other DNA
                        organism = synthetic construct
SEQUENCE: 1
aatgatacgg cgaccaccga gactacac                                     28

SEQ ID NO: 2            moltype = DNA  length = 23
FEATURE                 Location/Qualifiers
source                  1..23
                        mol_type = other DNA
                        organism = synthetic construct
SEQUENCE: 2
caagcagaag acggcatacg aat                                          23

SEQ ID NO: 3            moltype = DNA  length = 23
FEATURE                 Location/Qualifiers
source                  1..23
                        mol_type = other DNA
                        organism = synthetic construct
SEQUENCE: 3
caagcagaag acggcataca gat                                          23

SEQ ID NO: 4            moltype = DNA  length = 35
FEATURE                 Location/Qualifiers
source                  1..35
                        mol_type = other DNA
                        organism = synthetic construct
SEQUENCE: 4
gctggcacgt ccgaacgctt cgttaatccg ttgag                             35

SEQ ID NO: 5            moltype = DNA  length = 35
FEATURE                 Location/Qualifiers
source                  1..35
                        mol_type = other DNA
                        organism = synthetic construct
SEQUENCE: 5
ctcaacggat taacgaagcg ttcggacgtg ccagc                             35

SEQ ID NO: 6            moltype = DNA  length = 35
FEATURE                 Location/Qualifiers
source                  1..35
                        mol_type = other DNA
                        organism = synthetic construct
SEQUENCE: 6
cgtcgtctgc catggcgctt cggtggatat gaact                             35

SEQ ID NO: 7            moltype = DNA  length = 35
FEATURE                 Location/Qualifiers
source                  1..35
                        mol_type = other DNA
                        organism = synthetic construct
SEQUENCE: 7
agttcatatc caccgaagcg ccatggcaga cgacg                             35

SEQ ID NO: 8            moltype = DNA  length = 35
FEATURE                 Location/Qualifiers
source                  1..35
                        mol_type = other DNA
                        organism = synthetic construct
SEQUENCE: 8
acggccgcta atatcaacgc gtcgaatccg caact                             35

SEQ ID NO: 9            moltype = DNA  length = 35
FEATURE                 Location/Qualifiers
source                  1..35
                        mol_type = other DNA
                        organism = synthetic construct
SEQUENCE: 9
agttgcggat tcgacgcgtt gatattagcg gccgt                             35

SEQ ID NO: 10           moltype = DNA  length = 34
FEATURE                 Location/Qualifiers
source                  1..34
                        mol_type = other DNA
                        organism = synthetic construct
```

-continued

```
SEQUENCE: 10
gccgcgttac gttagccgga ctattcgatg cagc                              34

SEQ ID NO: 11           moltype = DNA  length = 34
FEATURE                 Location/Qualifiers
source                  1..34
                        mol_type = other DNA
                        organism = synthetic construct
SEQUENCE: 11
gctgcatcga atagtccggc taacgtaacg cggc                              34

SEQ ID NO: 12           moltype = DNA  length = 29
FEATURE                 Location/Qualifiers
source                  1..29
                        mol_type = other DNA
                        organism = synthetic construct
misc_difference         23
                        note = allyl T
SEQUENCE: 12
aatgatacgg cgaccaccga ganctacac                                    29

SEQ ID NO: 13           moltype = DNA  length = 24
FEATURE                 Location/Qualifiers
source                  1..24
                        mol_type = other DNA
                        organism = synthetic construct
modified_base           22
                        mod_base = OTHER
                        note = 8-oxoguanine
SEQUENCE: 13
caagcagaag acggcatacg anat                                         24

SEQ ID NO: 14           moltype = DNA  length = 24
FEATURE                 Location/Qualifiers
source                  1..24
                        mol_type = other DNA
                        organism = synthetic construct
modified_base           20
                        mod_base = OTHER
                        note = 8-oxoguanine
SEQUENCE: 14
caagcagaag acggcatacn agat                                         24

SEQ ID NO: 15           moltype = DNA  length = 24
FEATURE                 Location/Qualifiers
source                  1..24
                        mol_type = other DNA
                        organism = synthetic construct
modified_base           20
                        mod_base = OTHER
                        note = 8-oxoguanine
modified_base           22
                        mod_base = OTHER
                        note = 8-oxoguanine
SEQUENCE: 15
caagcagaag acggcatacn anat                                         24

SEQ ID NO: 16           moltype = DNA  length = 29
FEATURE                 Location/Qualifiers
source                  1..29
                        mol_type = other DNA
                        organism = synthetic construct
modified_base           23
                        mod_base = OTHER
                        note = URACIL
SEQUENCE: 16
aatgatacgg cgaccaccga gatctacac                                    29

SEQ ID NO: 17           moltype = DNA  length = 24
FEATURE                 Location/Qualifiers
source                  1..24
                        mol_type = other DNA
                        organism = synthetic construct
SEQUENCE: 17
aggaggagga ggaggaggag gagg                                         24

SEQ ID NO: 18           moltype = DNA  length = 24
FEATURE                 Location/Qualifiers
source                  1..24
```

-continued

```
                         mol_type = other DNA
                         organism = synthetic construct
SEQUENCE: 18
cctcctcctc ctcctcctcc tcct                                             24
```